(12) United States Patent
Sommer

(10) Patent No.: US 11,372,008 B2
(45) Date of Patent: Jun. 28, 2022

(54) BLOOD FACTOR MONITORING ASSAY AND USES THEREOF

(71) Applicant: Bioverativ Therapeutics Inc., Waltham, MA (US)

(72) Inventor: Jurg Sommer, Wayland, MA (US)

(73) Assignee: Bioverativ Therapeutics Inc., Waltham, MA (US)

(*) Notice: Subject to any disclaimer, the term of this patent is extended or adjusted under 35 U.S.C. 154(b) by 499 days.

(21) Appl. No.: 15/979,349

(22) Filed: May 14, 2018

(65) Prior Publication Data

US 2018/0364263 A1 Dec. 20, 2018

Related U.S. Application Data

(63) Continuation of application No. 14/416,214, filed as application No. PCT/US2013/052101 on Jul. 25, 2013, now Pat. No. 10,001,495.

(60) Provisional application No. 61/675,713, filed on Jul. 25, 2012.

(51) Int. Cl.
*G01N 33/86* (2006.01)
*G01N 33/92* (2006.01)
*A61K 38/48* (2006.01)

(52) U.S. Cl.
CPC ......... *G01N 33/86* (2013.01); *A61K 38/4846* (2013.01); *C12Y 304/21022* (2013.01); *G01N 33/92* (2013.01); *G01N 2333/755* (2013.01); *G01N 2333/9645* (2013.01); *G01N 2500/00* (2013.01); *G01N 2800/224* (2013.01)

(58) Field of Classification Search
None
See application file for complete search history.

(56) References Cited

U.S. PATENT DOCUMENTS

| | | | |
|---|---|---|---|
| 3,486,859 A | 12/1969 | Rudolf et al. | |
| 3,695,842 A | 10/1972 | Mintz | |
| 3,836,333 A | 9/1974 | Mintz | |
| 3,890,098 A | 6/1975 | Moreno | |
| 3,951,606 A | 4/1976 | Moyer et al. | |
| 4,197,734 A | 4/1980 | Rosenberg | |
| 4,659,550 A | 4/1987 | Schildknecht | |
| 4,725,554 A | 2/1988 | Schildknecht | |
| 4,757,006 A | 7/1988 | Toole, Jr. et al. | |
| 4,797,369 A | 1/1989 | Mintz | |
| 4,868,112 A | 9/1989 | Toole, Jr. | |
| 4,965,199 A | 10/1990 | Capon et al. | |
| 4,994,371 A | 2/1991 | Davie et al. | |
| 5,004,803 A | 4/1991 | Kaufman et al. | |
| 5,039,617 A | 8/1991 | McDonald et al. | |
| 5,059,525 A * | 10/1991 | Bartl ............... | C12Q 1/56 435/177 |
| 5,112,950 A | 5/1992 | Meulien et al. | |
| 5,171,844 A | 12/1992 | Van Ooyen et al. | |
| 5,284,624 A | 2/1994 | Behnk | |
| 5,302,348 A | 4/1994 | Cusack et al. | |
| 5,364,771 A | 11/1994 | Lollar et al. | |
| 5,418,143 A | 5/1995 | Zweig | |
| 5,506,112 A | 4/1996 | Lang et al. | |
| 5,506,146 A | 4/1996 | Josef | |
| 5,534,226 A | 7/1996 | Gavin et al. | |
| 5,543,502 A | 8/1996 | Nordfang et al. | |
| 5,595,886 A | 1/1997 | Chapman et al. | |
| 5,610,278 A | 3/1997 | Nordfang et al. | |
| 5,627,038 A * | 5/1997 | Hemker ............... | C12Q 1/56 435/23 |
| 5,789,203 A | 8/1998 | Chapman et al. | |
| 5,859,204 A | 1/1999 | Lollar | |
| 5,866,122 A * | 2/1999 | Turecek ............... | C07K 14/745 424/94.64 |
| 5,908,786 A | 6/1999 | Moreno et al. | |
| 5,972,885 A | 10/1999 | Spira et al. | |
| 6,048,720 A | 4/2000 | Dalborg et al. | |
| 6,060,447 A | 5/2000 | Chapman et al. | |
| 6,100,050 A | 8/2000 | Hemker et al. | |
| 6,114,135 A | 9/2000 | Goldstein | |
| 6,228,620 B1 | 5/2001 | Chapman et al. | |
| 6,251,632 B1 | 6/2001 | Lillicrap et al. | |
| 6,316,226 B1 | 11/2001 | Van Ooyen et al. | |
| 6,346,513 B1 | 2/2002 | Van Ooyen et al. | |

(Continued)

FOREIGN PATENT DOCUMENTS

EP 0295597 A2 12/1988
WO WO-8704187 A1 7/1987

(Continued)

OTHER PUBLICATIONS

Carlsson et al., Haemophilia. Mar. 1998;4(2):83-8.*
Van Dijk et al., Haematologica. Apr. 2005;90(4):494-8.*
Over, J., Scand J Haematol Suppl. 1984;41:13-24.*
Collins et al,, Haemophilia. Jan. 2011;17(1 ):2-10. doi: 10.1111/j. 1365-2516.2010.02370.x. Epub Aug. 22, 2010.*
Andersson, L.O., et al., "Purification and Characterization of Human Factor IX," Thrombosis Research 7(3):451-459, Pergamon Press, Inc., United States (1975).
Cameron, C., et al., "The Canine Factor VIII cDNA and 5' Flanking Sequence," Thrombosis and Haemostasis 79(2):317-322, Schattauer Verlag, Germany (1998).

(Continued)

*Primary Examiner* — Michael Szperka
(74) *Attorney, Agent, or Firm* — Lathrop GPM LLP; James H. Velema, Esq.

(57) ABSTRACT

The present disclosure provides methods and compositions for diagnosing and treating subject having a bleeding disorder. The disclosed methods comprise contacting a sample, e.g., a blood or plasma sample obtained from the patient, with an activation mixture comprising an activated coagulation factor and a phospholipid mixture, wherein the activation mixture is dried onto a solid substrate. Also provided is a global hemostasis test based on the integration of clotting time (Ct) and pharmacokinetics data. The methods and compositions presented can be applied to point-of-care diagnostic systems.

9 Claims, 23 Drawing Sheets

Specification includes a Sequence Listing.

(56) References Cited

U.S. PATENT DOCUMENTS

| | | | |
|---|---|---|---|
| 6,376,463 B1 | 4/2002 | Lollar | |
| 6,451,610 B1 | 9/2002 | Gorman et al. | |
| 6,458,563 B1 | 10/2002 | Lollar | |
| 6,673,622 B1 | 1/2004 | Jina | |
| 6,750,053 B1 | 6/2004 | Widrig et al. | |
| 6,994,984 B2 | 2/2006 | Gempeler et al. | |
| 7,005,857 B2 | 2/2006 | Stiene et al. | |
| 7,041,635 B2 | 5/2006 | Kim et al. | |
| 7,235,213 B2 | 6/2007 | Mpock et al. | |
| 7,348,004 B2 | 3/2008 | Peters et al. | |
| 7,404,956 B2 | 7/2008 | Peters et al. | |
| 7,775,976 B2 | 8/2010 | Fuller et al. | |
| 8,476,234 B2 * | 7/2013 | Fima | C07K 14/505 530/398 |
| 10,001,495 B2 * | 6/2018 | Sommer | G01N 33/86 |
| 2005/0032174 A1 | 2/2005 | Peters et al. | |
| 2005/0100990 A1 | 5/2005 | Saenko et al. | |
| 2009/0053297 A1 | 2/2009 | Balu-Iyer et al. | |
| 2015/0079072 A1 | 3/2015 | Sommer et al. | |

FOREIGN PATENT DOCUMENTS

| | | | |
|---|---|---|---|
| WO | WO-8800831 A1 | 2/1988 | |
| WO | WO-8803558 A1 | 5/1988 | |
| WO | WO-8808035 A1 | 10/1988 | |
| WO | WO-9109122 A1 | 6/1991 | |
| WO | WO-9320093 A1 | 10/1993 | |
| WO | WO-9411503 A2 | 5/1994 | |
| WO | WO-0240544 A2 | 5/2002 | |
| WO | WO-03020764 A2 | 3/2003 | |
| WO | WO-2004101740 A2 | 11/2004 | |
| WO | WO-2004102202 A1 | 11/2004 | |
| WO | WO-2005001025 A2 | 1/2005 | |
| WO | WO-2006074199 A1 | 7/2006 | |
| WO | WO-2007149406 A2 | 12/2007 | |
| WO | WO-2008118507 A2 | 10/2008 | |
| WO | WO-2009051717 A2 | 4/2009 | |
| WO | WO-2009130198 A2 | 10/2009 | |
| WO | WO-2009137254 A2 | 11/2009 | |
| WO | WO-2009140015 A2 | 11/2009 | |
| WO | WO-2011069164 A2 | 6/2011 | |
| WO | WO-2012006624 A2 | 1/2012 | |
| WO | WO-2013016454 A1 | 1/2013 | |
| WO | WO-2014008480 A2 | 1/2014 | |
| WO | WO-2014018777 A2 | 1/2014 | |
| WO | WO-2014063108 A1 * | 4/2014 | A61K 38/36 |

OTHER PUBLICATIONS

Cutler, J.A., et al., "The Identification and Classification of 41 novel Mutations in the Factor VIII Gene (F8C)," Human Mutation 19(3):274-278, Wiley-Liss, Inc., England (2002).
Eaton, D.L., et al., "Construction and Characterization of an Active Factor VIII Variant Lacking the Central One-Third of the Molecule," Biochemistry 25(26):8343-8347, American Chemical Society, United States (1986).
Gitschier, J., et al., "Characterization of the Human Factor VIII Gene," Nature 312(5992):326-330, Nature Publishing Group, England (1984).
Healey, J.F., et al., "The cDNA and Derived Amino Acid Sequence of Porcine Factor VIII," Blood 88(11):4209-4214, The American Society of Hematology, United States (1996).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).

International Preliminary Report on Patentability for International Application No. PCT/US2013/052101, International Bureau of WIPO, Switzerland, dated Jan. 27, 2015, 7 pages.
International Search Report for International Application No. PCT/US2013/052101, International Searching Authority, United States, dated Feb. 10, 2014, 5 pages.
Kasuda, S., et al., "Establishment of embryonic stem cells secreting human factor VIII for cell-based treatment of hemophilia A," Journal of Thrombosis and Haemostasis 6(8):1352-1359, International Society on Thrombosis and Haemostasis, England (2008).
Langner, K-D., et al., "Synthesis of Biologically Active Deletion Mutants of Human Factor VIII:C," Behring Institute Mitteilungen 82:16-25, Behringwerke AG, Germany (1988).
Mannucci, P.M. and Tuddenham, E.G.D., "The Hemophilias—from Royal Genes to Gene Therapy," New England Journal of Medicine 344(23):1773-1779, Massachusetts Medical Society, United States (2001).
Meulien, P., et al., "A new Recombinant Procoagulant Protein Derived from the cDNA Encoding Human Factor VIII," Protein Engineering 2(4):301-306, IRL Press Ltd., England (1988).
Miao, H.Z., et al., "Bioengineering of coagulation factor VIII for improved secretion," Blood 103(9):3412-3419, The American Society of Hematology, United States (2004).
Pipe, S.W., et al., "Functional factor VIII made with von Willebrand factor at high levels in transgenic milk," Journal of Thrombosis and Haemostasis 9(11):2235-2242, International Society on Thrombosis and Haemostasis, England (Nov. 2011).
Rodriguez-Merchan, E.C. "Management of Musculoskeletal Complications of Hemophilia," Seminars in Thrombosis and Hemostasis 29(1):87-95, Thieme, United States (2003).
Sarver, N., et al., "Stable Expression of Recombinant Factor VIII Molecules Using a Bovine Papillomavirus Vector," DNA 6(6):553-564, Mary Ann Liebert, Inc., United States (1987).
Toole, J.J., et al., "A large region (95 kDa) of human factor VIII is dispensable for in vitro procoagulant activity," Proceedings of the National Academy of Sciences USA 83(16):5939-5942, National Academy of Sciences, United States (1986).
Toole, J.J., et al., "Molecular Cloning of a cDNA Encoding Human Antihaemophilic Factor," Nature 312(5992):342-347, Nature Publishing Group, England (1984).
Vehar, G.A., et al., "Structure of Human Factor VIII," Nature 312(5992):337-342, Nature Publishing Group, England (1984).
Wood, W.I., et al., "Expression of Active Human Factor VIII from Recombinant DNA Clones," Nature 312(5992):330-337, Nature Publishing Group, England (1984).
Written Opinion for International Application No. PCT/US2013/052101, International Searching Authority, United States, dated Feb. 10, 2014, 6 pages.
Ahnström, J., et al., "A 6-year Follow-Up of Dosing, Coagulation Factor Levels and Bleedings in Relation to Joint Status in the Prophylactic Treatment of Haemophilia," Haemophilia 10(6):689-697, Blackwell Publishing Ltd., England (2004).
Collins, P.W., et al., "Implications of Coagulation Factor VIII and IX Pharmacokinetics in the Prophylactic Treatment of Haemophilia," Haemophilia 17(1):2-10, Blackwell Publishing Ltd., England (2011).
Extended European Search Report for EP Application No. 13823087. 5, European Patent Office, Germany, dated May 3, 2016, 9 pages.
Carlsson et al . . . , "Multidose pharmacokinetics of factor IX: implications for dosing in prophylaxis," Haemophilia 4(2):83-88 (Mar. 1998).
Van Dijk et al., "Factor VIII half-life and clinical phenotype of severe hemophilia A," Haematologica 90(4):494-498 (Apr. 2005).
Over, J., "Methodology of the One-Stage Assay of Factor VIII (VIII:C)," Scand J Haematol Suppl 41:13-24 (1984).
Barrowcliffe, T.W., "Methodology of the Two-Stage Assay of Factor VIII (VIII:C)," Scand J Haematol Suppl 41:25-38 (1984).

* cited by examiner

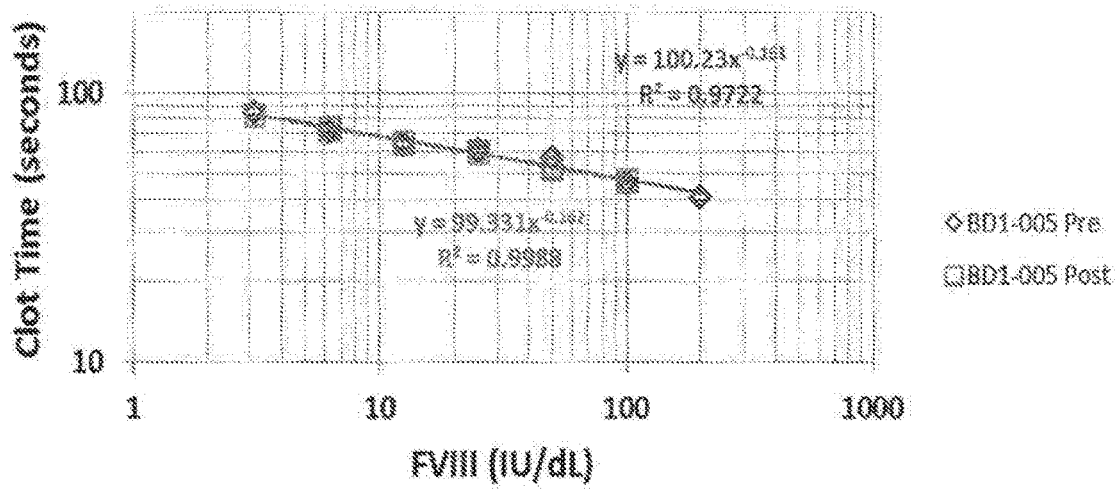
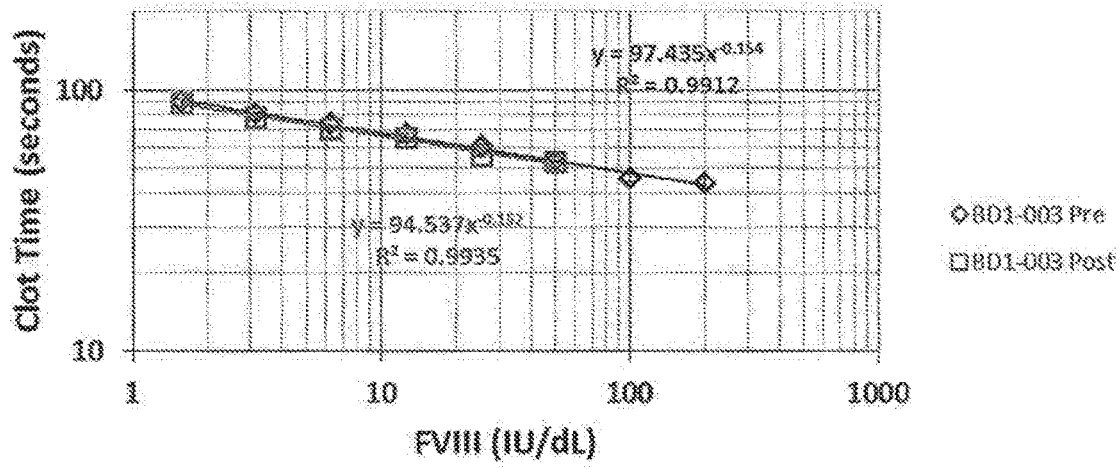

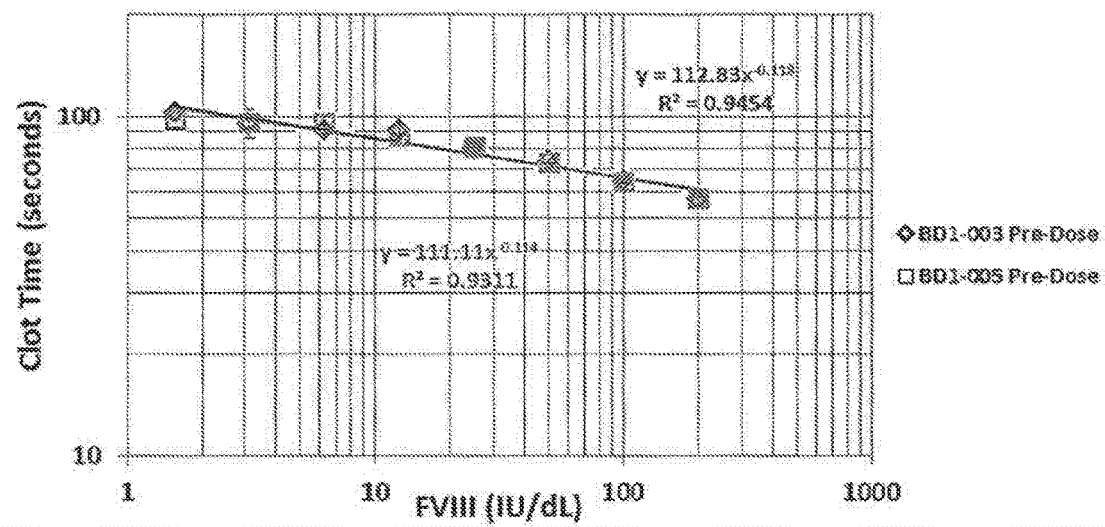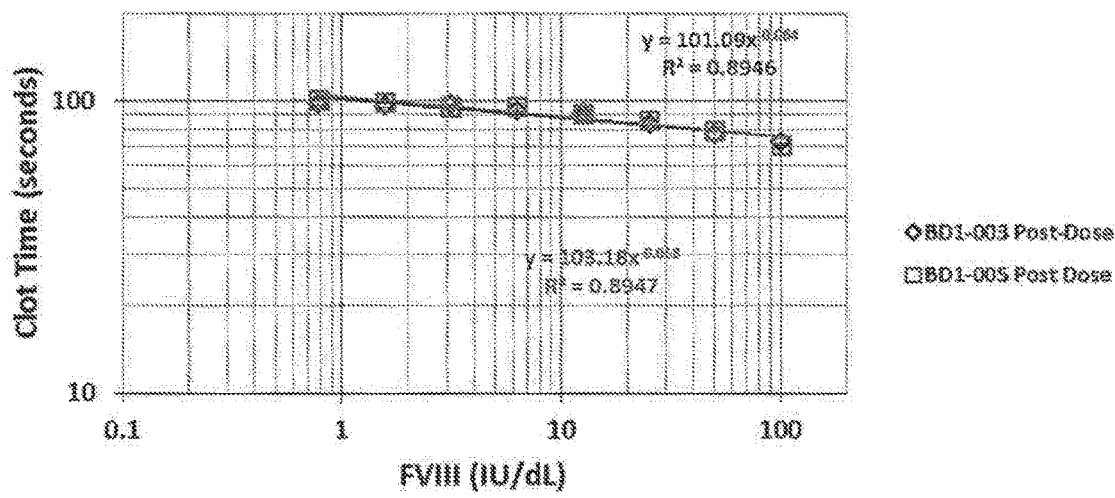

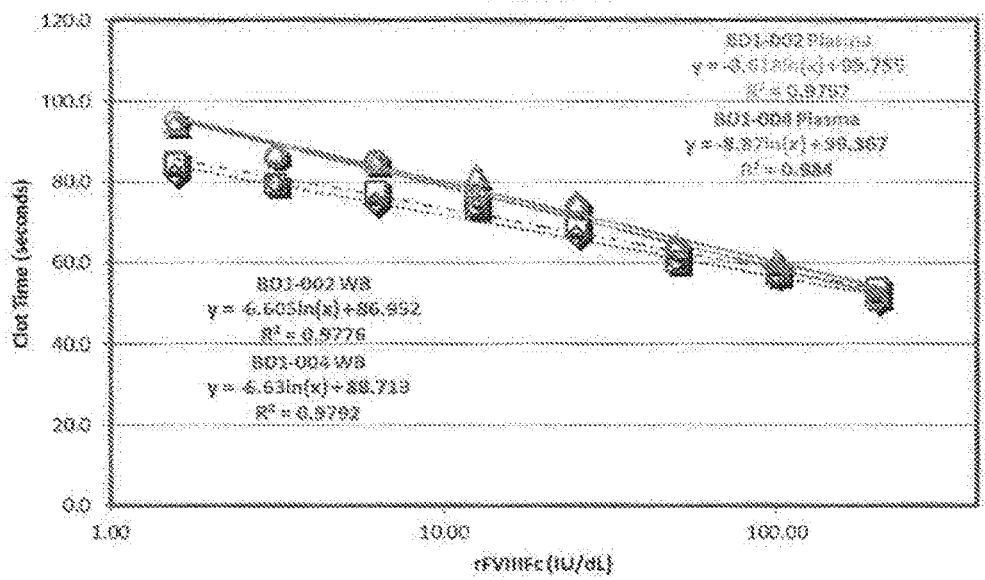
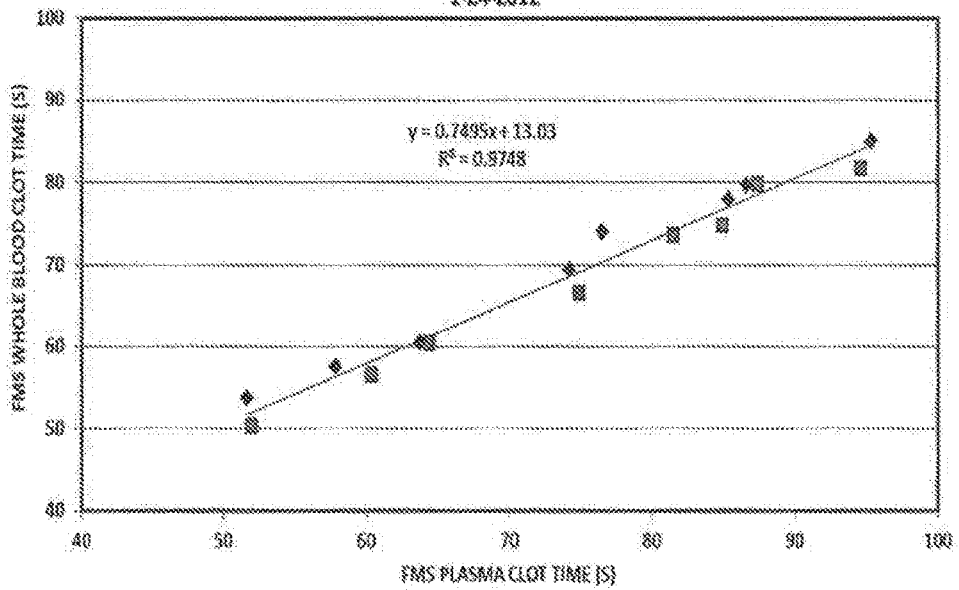

BLOOD FACTOR MONITORING ASSAY AND USES THEREOF

CROSS-REFERENCE TO RELATED APPLICATIONS

This application is a continuation application of U.S. application Ser. No. 14/416,214, filed Jan. 21, 2015 under 35 U.S.C. § 371, now U.S. Pat. No. 10,001,495, and which is based on International Application No. PCT/US2013/052101, filed Jul. 25, 2013, which claims the benefit of U.S. Provisional Application No. 61/675,713, filed Jul. 25, 2012, all of which are incorporated herein by reference in their entireties.

REFERENCE TO SEQUENCE LISTING SUBMITTED ELECTRONICALLY

The content of the electronically submitted sequence listing (Name: 4159.3840002_SequenceListing.txt; Size: 112,899 bytes; and Date of Creation: May 14, 2018) is herein incorporated by reference in its entirety.

BACKGROUND

Field of the Invention

The present invention relates generally to the field of therapeutics for hemostatic disorders.

Background Art

Hemophilia is a bleeding disorder in which blood clotting is disturbed by a lack of certain plasma clotting factors in the coagulation cascade (FIG. 1). Hemophilia A and Hemophilia B are two different types of hemophilia that are caused by deficiencies in Factor VIII (FVIII) and Factor IX, respectively.

Hemophilia A is characterized by spontaneous hemorrhage and excessive bleeding after trauma. Over time, the repeated bleeding into muscles and joints, which often begins in early childhood, results in hemophilic arthropathy and irreversible joint damage. This damage is progressive and can lead to severely limited mobility of joints, muscle atrophy and chronic pain (Rodriguez-Merchan, E. C., Semin. Thromb. Hemost. 29:87-96 (2003), which is herein incorporated by reference in its entirety).

Hemophilia B (also known as Christmas disease) is one of the most common inherited bleeding disorders in the world. It results in decreased in vivo and in vitro blood clotting activity and requires extensive medical monitoring throughout the life of the affected individual. In the absence of intervention, the afflicted individual will suffer from spontaneous bleeding in the joints, which produces severe pain and debilitating immobility; bleeding into muscles results in the accumulation of blood in those tissues; spontaneous bleeding in the throat and neck can cause asphyxiation if not immediately treated; renal bleeding; and severe bleeding following surgery, minor accidental injuries, or dental extractions also are prevalent.

Treatment of hemophilia is by replacement therapy targeting restoration of Factor VIII and Factor IX activity. Treatment of hemophilia A is by replacement therapy targeting restoration of FVIII activity to 1 to 5% of normal levels to prevent spontaneous bleeding (Mannucci, P. M., et al., N. Engl. J. Med. 344:1773-1779 (2001), which is herein incorporated by reference in its entirety). There are plasma-derived and recombinant FVIII products available to treat bleeding episodes on-demand or to prevent bleeding episodes from occurring by treating prophylactically. Based on the half-life of these products treatment regimens require frequent intravenous administration. Such frequent administration is painful and inconvenient.

Treatment of hemophilia B occurs by replacement of the missing clotting factor by exogenous factor concentrates highly enriched in Factor IX, but is also problematic. Generating such a concentrate from blood is fraught with technical difficulties. Purification of Factor IX from plasma (plasma derived Factor IX; pdFIX) almost exclusively yields active Factor IX. However, such purification of factor IX from plasma is very difficult because Factor IX is only present in low concentration in plasma (5 ug/mL. Andersson, Thrombosis Research 7: 451 459 (1975). Further, purification from blood requires the removal or inactivation of infectious agents such as HIV and HCV. In addition, pdFIX has a short half-life and therefore requires frequent dosing. Recombinant factor IX (rFIX) is also available, but suffers from the same short half-life and need for frequent dosing (e.g., 2-3 times per week for prophylaxis) as pdFIX. rFIX also has a lower incremental recovery (K value) compared to pdFIX, which necessitates the use of higher doses of rFIX than those for pdFIX.

Reduced mortality, prevention of joint damage and improved quality of life have been important achievements due to the development of plasma-derived and recombinant Factor VIII and Factor IX products. Prolonged protection from bleeding would represent another key advancement in the treatment of hemophilia patients. In order to address this need, recombinant Factor VIII and Factor IX proteins expressed as Fc fusions are in development. However, methods of determining appropriate dosage of these products, which have unique pharmacokinetic properties in humans have not yet been developed. Therefore, there remains a need for improved methods of treating hemophilia due to Factor VIII and Factor IX deficiencies that are more tolerable and more effective than current therapies.

Coagulation assays have gained acceptance as an important tool for management of patients being treated for coagulation disorders. These treatments are also applicable to patients on anticoagulation therapy for the prevention of clots in their blood vessels. In these assays, a sample of the patient's blood or plasma is tested for coagulation time or "clotting time" which time is related to the amount of coagulation factors in the patient's blood (or to the patient's dosage of anticoagulant in the case of patients undergoing antocoagulation therapy). Coagulation assays are also required prior to surgical procedures even for patients not suffering from bleeding disorders or on anticoagulation therapy. This is because the medical professionals need to clearly know the bleeding susceptibility before they are operated on.

A variety of coagulation test are presently in use and among the most popular is the "Activated Partial Thromboplastin Time" (aPTT) test (see FIG. 2). Blood coagulation tests have tended to be complex, and the bulk of them are performed generally in centralized clinical laboratories. Clinical or a doctor's office visits or a regular basis to monitor coagulation factor levels can be very inconvenient and expensive. Most of apparatus and methods known for measuring coagulation time in blood samples cannot be used for home testing (see, e.g., U.S. Pat. Nos. 3,695,842; 3,836,333; 4,197,734; 3,486,859; 4,797,369; 3,890,098; 4,725,554; 5,284,624; 3,951,606; 4,659,550; and 5,302,348). The disadvantages of these methods, beside cost and the challenge of operation, include the fact that most do not measure coagulation directly. The large blood volume requirements of some of these methods made them impractical for home use. Many of these methods are also limited by what kinds of coagulation tests they can perform due to the reagent chemistry requirements and the detectable signal generated.

BRIEF SUMMARY

The present disclosure provides a composition for the measurement of coagulation factor activity in a sample comprising an activated coagulation factor and a phospholipid mixture, wherein the composition is dried onto a solid substrate. The present disclose also provides a composition for the measurement of coagulation time in a sample comprising an activated coagulation factor and a phospholipid mixture, wherein the composition is dried onto a solid substrate. In some aspects, the solid substrate is selected from the group consisting of paper, plastic, glass, ceramic material, metal, and combinations thereof. In other aspects, the solid substrate is a surface on a test strip, test stick, reaction chamber, cartridge, chip, well plate, or array used in an apparatus to measure coagulation factor activity or coagulation time.

In some aspects, the coagulation factor is selected from the group consisting of FVII, FVIII, and FIX. In other aspects, the coagulation factor is a Factor VIII protein or a fragment, variant, or derivative thereof. In some aspects, the coagulation factor is a Factor IX protein or a fragment, variant, or derivative thereof. In other aspects, the activated coagulation factor is a Factor IXa protein or a fragment, variant, or derivative thereof. In some aspects, Factor IXa is present in the composition prior to drying within a range of 0.01 to 0.05 U/mL. In other aspects, the activated coagulation factor is a Factor XIa protein or a fragment, variant, or derivative thereof. In some aspects, Factor XIa is present in the composition prior to drying within a range of 0.01 to 0.05 U/mL.

In some aspects, the phospholipid mixture comprises 2 phospholipids. In other aspects, the phospholipid mixture comprises 3 phospholipids. In some aspects, the phospholipids are selected from the group consisting of phosphatidylcholine, phosphatidylserine, phosphatidylglycerol, and combinations thereof. In other aspects, the phospholipids are natural phospholipids, synthetic phospholipids, or combinations thereof. In some aspects, the phospholipid mixture comprises 70 mole-% of phosphatidylcholine and 30 mole-% of phosphatidylserine. In other aspects, the phospholipid mixture comprises 80 mole-% of phosphatidylcholine, 10 mole-% of phosphatidylserine, and 10 mole-% of phosphatidylglycerol. In some aspects, the phospholipid mixture comprises 75 mole-% of phosphatidylcholine, 20 mole-% of phosphatidylserine, and 5 mole-% of phosphatidylglycerol. In other aspects, the phospholipid mixture further comprises cholesterol. In some aspects, the cholesterol content in the phospholipid mixture is from about 1 to about 20 mole-% of cholesterol.

In some aspects, the phospholipid mixture is in vesicle form. In other aspects, the vesicles are small unilamellar vesicles. In some aspects, the composition further comprises divalent cations. In other aspects, the divalent cations are calcium ions. In some aspects, the sample is selected from the group consisting of whole blood, citrated or equivalently stabilized blood, plasma, or other fluid sample containing or suspected of containing a coagulation factor. In other cases, the sample is decalcified.

In some aspects, the measurement is carried in a point of care test system. In some aspects, the measurement is carried out in a mechanical or optical analytical system.

The present disclosure provides a composition for the measurement of the Factor VIII activity of a Factor VIII protein or a fragment, variant, or derivative thereof in a sample comprising 80% of 0.1 mg/mL Factor IXa and 20% of a phospholipid mixture comprising 75 mole-% of phosphatidylcholine, 20 mole-% of phosphatidylserine, and 5 mole-% of phosphatidylglycerol, wherein said composition is dried onto a solid substrate. Also provided is a composition for the measurement of the Factor IX activity of a Factor IX protein or a fragment, variant, or derivative thereof in a sample comprising 80% Factor XIa suspension and 20% of a phospholipid mixture comprising 75 mole-% of phosphatidylcholine, 20 mole-% of phosphatidylserine, and 5 mole-% of phosphatidylglycerol, wherein said composition is dried onto a solid substrate. The exact amount of FXIa needed varies depending on the specific activity of this reagent and is titrated for optimal amount and can include approximately 0.1 mg/mL.

The present disclosure also provides a kit for performing a measurement of coagulation factor activity or coagulation time in a sample comprising a composition disclosed herein in one or more vials. Also provided is a kit for performing a measurement of coagulation factor activity or coagulation time in a sample comprising a composition disclosed herein in a non-dry form in one or more vials and instructions for drying said composition onto a solid substrate. The instant disclosure also provides a sample holder for performing a blood coagulation assay, comprising a surface coated with any of the activation mixtures disclosed herein. In some aspects, the sample holder is selected from the group consisting of a test strip, a test stick, a reaction chamber, a cartridge, a chip, a well plate, and an array.

The present disclosure provides a method for determining clotting time in a patient having a bleeding disorder, comprising (a) contacting a sample obtained from the patient with an activation mixture comprising an activated coagulation factor and a phospholipid mixture, wherein the activation mixture is dried onto a solid substrate; and, (b) measuring the time between the contacting of the activation mixture with the blood sample and the onset of clotting, thereby calculating the clotting time (Ct).

Also provided is a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient will benefit from administration of a treatment; and, (c) administering the treatment to the patient if Ct indicates that the patient will benefit from administration of the treatment. The present disclosure also provides a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient will benefit from administration of a treatment; and, (c) instructing a healthcare provider to administer the treatment to the patient if Ct indicates that the patient will benefit from administration of the treatment.

The present disclosure provides a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct correlates with a therapeutically efficacious treatment; and, (c) administering an optimized treatment to the patient, wherein the treatment is maintained or adjusted. Also provides is a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct correlates with a therapeutically efficacious treatment; and, (c) instructing a healthcare provider to optimize the treatment administered, wherein the treatment is maintained or adjusted.

The present disclosure also provides a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient has a bleeding disorder; and, (c) providing a treatment for the bleeding disorder if the patient is in need thereof. Also provided is a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient has a bleeding disorder; and, (c) instructing a healthcare provider to provide treatment for the bleeding disorder if the patient is in need thereof.

The present disclosure also provides a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) comparing the measured Ct with the Ct obtained from a corresponding standard, wherein the standard is representative of a therapeutically efficacious treatment, and wherein a similarity between the patient's results and the standard is indicative of efficacy of the patient's current treatment; and, (d) maintaining or adjusting the patient's treatment based on the relative difference between the patient's results and the corresponding standard. Also provided is a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) comparing the measured Ct with the Ct obtained from a corresponding standard, wherein the standard is representative of a therapeutically efficacious treatment, and wherein a similarity between the patient's results and the standard is indicative of efficacy of the patient's current treatment; and, (d) instructing a healthcare provider to maintain or adjusting the patient's treatment based on the relative difference between the patient's results and the corresponding standard.

The present disclosure also provides a method for determining a coagulation factor level in a bleeding disorder patient, comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) correlating the Ct value with the level of coagulation factor in the sample. In some aspects, the correlation between Ct and coagulation factor level (% Factor) is calculated according to the formula:

$$Ct = A \times \mathrm{Ln}(\% \text{ Factor}) + B \quad \quad \text{[Formula I]}$$

wherein, for each coagulation factor, A is a constant value corresponding to the slope of a Ct versus coagulation factor concentration dose-response, and B is patient-specific off-set value.

The present disclosure also provides a method for determining a pharmacokinetic (PK) parameter in a bleeding disorder patient, comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) correlating a PK with the calculated Ct value, thereby determining the value of the PK parameter.

The present disclosure provides a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter indicates that the patient will benefit from administration of the treatment; and, (d) administering the treatment to the patient if the PK parameter indicates that the patient will benefit from administration of the treatment. Also provides is a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter indicates that the patient will benefit from administration of the treatment; and, (d) instructing a healthcare provider to administer the treatment to the patient if the PK parameter indicates that the patient will benefit from administration of the treatment. Also provided is method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter correlates with a therapeutically efficacious treatment; and, (d) administering an optimized treatment to the patient, wherein the treatment is maintained or adjusted. The present disclosure also provides a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter correlates with a therapeutically efficacious treatment; and, (d) instructing a healthcare provider to administer an optimized treatment to the patient, wherein the therapy is maintained or adjusted.

Also provided is a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) determining a PK parameter based on Ct, wherein the PK parameter indicates whether the patient has a bleeding disorder; and, (d) providing treatment for the bleeding disorder if the patient is in need thereof. Also provides is a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) determining a PK parameter based on Ct, wherein the PK parameter indicates whether the patient has a bleeding disorder; and, (d) instructing a healthcare provider to provide therapy to treat the bleeding disorder if the patient is in need thereof.

The present disclosure also provides a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) determining a PK parameter based on Ct; (d) comparing the PK parameter with the PK obtained from a corresponding standard, wherein the standard is representative of a therapeutically efficacious treatment, and wherein a similarity between the patient's results and the standard is indicative of efficacy of the patient's current treatment; and, (e) maintaining or adjusting the patient's treatment based on the relative difference between the patient's results and the corresponding standard. Also provided is a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct; (d) comparing the PK parameter with the PK obtained from a corresponding standard, wherein the standard is representative of a therapeutically efficacious treatment, and wherein a similarity between the patient's results and the standard is indicative of efficacy of the patient's current treatment; and, (e) instructing a healthcare provider to maintain or adjust the patient's treatment based on the relative difference between the patient's results and the corresponding standard.

In some aspects, the PK is terminal half-life (HL). In other aspects, the PK is time to through (T). In some aspects, HL is calculated according to the formula:

$$HL = -0.693 \times (T_2 - T_1) \times A / (Ct_1 - Ct_2) \quad \text{[Formula II]}$$

wherein, for each coagulation factor, A is a constant value corresponding to the slope of a Ct versus coagulation factor concentration dose-response, $T_1$ and $T_2$ are times at which Ct is measured, and $Ct_1$ and $Ct_2$ are Ct values measured at $T_1$ and $T_2$, respectively.

In some aspects, T is calculated according to the formula:

$$T = -1.44 \times HL / (A \times (Ct_{measured} - Ct_{trough})) \quad \text{[Formula III]}$$

wherein for each coagulation factor A is a constant value corresponding to the slope of a Ct versus coagulation factor concentration dose-response, and HL is the terminal half-life, $Ct_{measured}$ is Ct measured at certain time point, and $Ct_{trough}$ is patient-specific clot time at trough. In some aspects, the patient is administered a new dose of coagulation factor every T interval.

In some aspects, the sample is selected from the group consisting of whole blood, citrated or equivalently stabilized blood, plasma, or other fluid sample containing or suspected of containing a coagulation factor. In some aspects, the sample is whole blood. In other aspects, the blood is venous blood. In some aspects, the blood is fingerstick blood. In some aspects, the sample is plasma. In some aspects, the sample is frozen and thawed prior to contacting the sample with the activation mixture. In other aspects, the sample is has not been frozen and thawed prior to contacting the sample with the activation mixture. In some aspects, the sample is decalcified. In some aspects, the decalcified sample is recalcified prior to contacting the sample with the activation mixture. In other aspects, the decalcified sample is recalcified after contacting the sample with the activation mixture.

In some aspects, the sample further comprises an added purified coagulation factor. In other aspects, the sample further comprises an added inhibitor. In some aspects, the purified coagulation factor is selected from the group consisting of Factors II, Factor VII, Factor VIII, Factor IX, Factor X, Factor XI, Factor XII, Factor XIII, Fibrinogen, vWF, Tissue Factor, and combinations thereof. In some aspects, the inhibitor is selected from the group consisting of CTI, aprotinin, ε-aminocaproic acid (EACA), D-Phenylalanyl-l-prolyl-l-arginine chloromethyl ketone-Factor VIIa (FPRCK-FVIIa), anti-coagulation factor monoclonal antibodies, and combinations thereof. In some aspects, the sample is diluted with substrate sample. In specific aspects, one part of sample is diluted with three parts of substrate sample.

In some aspects, the activated coagulation factor is a Factor IXa protein or a fragment, variant, or derivative thereof. In some aspects, Factor IXa is present in the composition prior to drying within a range of 0.01 to 0.05 U/mL. In other aspects, the activated coagulation factor is a Factor XIa protein or a fragment, variant, or derivative thereof. In some aspects, Factor XIa is present in the composition prior to drying within a range of 0.01 to 0.05 U/mL. In some aspects, the phospholipid mixture comprises 2 phospholipids. In some aspects, the phospholipid mixture comprises 3 phospholipids. In other aspects, the phospholipids in the phospholipid mixture are selected from the group consisting of phosphatidylcholine, phosphatidylserine, phosphatidylglycerol, and combinations thereof. In some aspects, the phospholipids are natural phospholipids, synthetic phospholipids, or combinations thereof. In some aspects, the phospholipid mixture comprises 70 mole-% of phosphatidylcholine and 30 mole-% of phosphatidylserine. In other aspects, the phospholipid mixture comprises 80 mole-% of phosphatidylcholine, 10 mole-% of phosphatidylserine, and 10 mole-% of phosphatidylglycerol. In other aspects, the phospholipid mixture comprises 75 mole-% of phosphatidylcholine, 20 mole-% of phosphatidylserine, and 5 mole-% of phosphatidylglycerol. In some aspects, the phospholipid mixture further comprises cholesterol. In some aspects, the cholesterol content in the phospholipid mixture is from about 1 to about 20 mole-% of cholesterol. In some aspects, the phospholipid mixture is in lipid vesicle form. In some aspects, the lipid vesicles are small unilamellar vesicles. In some aspects, the activation mixture further comprises divalent cations. In other aspects, the divalent cations are calcium ions.

In some aspects, the activation mixture reacts with a coagulation factor selected from the group consisting of Factor VII, Factor VIII, and Factor IX. In other aspects, the Factor VIII coagulation factor is a Factor VIII protein or a fragment, variant, or derivative thereof. In some aspects, the Factor IX coagulation factor is a Factor IX protein or a fragment, variant, or derivative thereof. In other aspects, the Factor VIII coagulation factor is a chimeric Factor VIII-Fc fusion protein. In some aspects, the Factor IX coagulation factor is a chimeric Factor IX-Fc fusion protein. In other aspects, the Fc portion of the chimeric Factor VIII or Factor IX protein comprises a human Fc domain. In some aspects, the chimeric Factor VIII protein comprises a B-domain deleted Factor VIII. In specific aspects, the chimeric Factor VIII protein comprises SEQ ID NO:6. In other aspects, the chimeric Factor VIII protein comprises SEQ ID NO:2. In some aspects, the chimeric Factor IX protein comprises SEQ ID NO: 13.

In some aspects, the solid substrate is selected from the group consisting of paper, plastic, glass, ceramic material, metal, and combinations thereof. In other aspects, the solid substrate is a surface on a test strip, test stick, reaction chamber, cartridge, chip, well plate, or array used in an apparatus to measure coagulation factor activity or coagulation time. In some aspects, the patient has not yet been treated with a coagulation factor. In some aspects, the patient has received prior coagulation factor treatment, but the treatment has been discontinued for a time period sufficient to deplete the coagulation factor treatment from the patient's blood. In some aspects, the measurement is carried in a point of care test system. In another aspect, the measurement is carried out in a mechanical or optical analytical system.

BRIEF DESCRIPTION OF THE DRAWINGS/FIGURES

Figure 3:
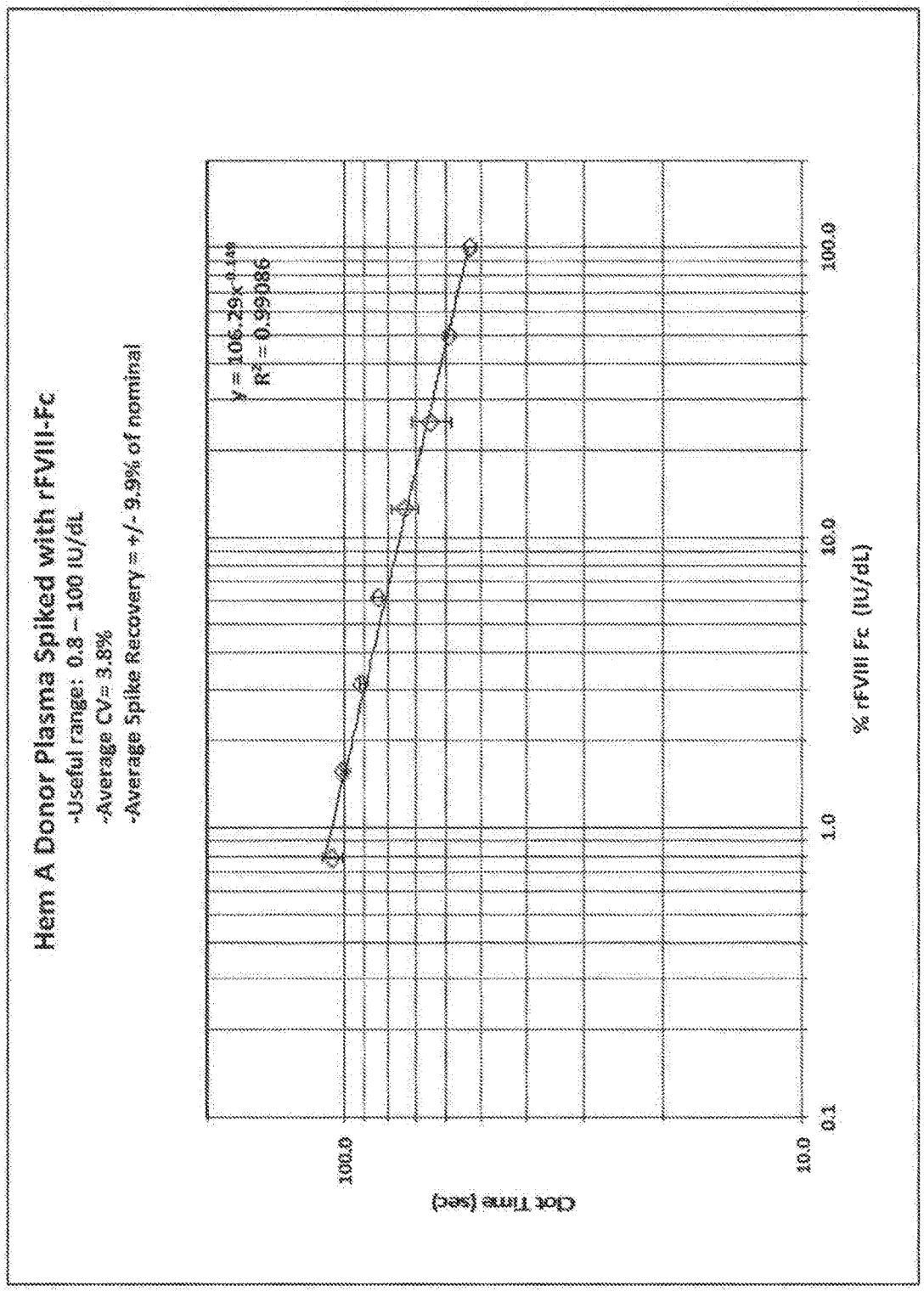

FIG. 3 shows clotting time for hemophilia A donor plasma spiked with rFVIIIFc measured using the Standard FMS Factor VIII assay. FIXa/phospholipid was used as activator mixture. Samples consisted of 12 μL of re-calcified plasma applied directly (without preincubation) to the test bed.

Figure 4:
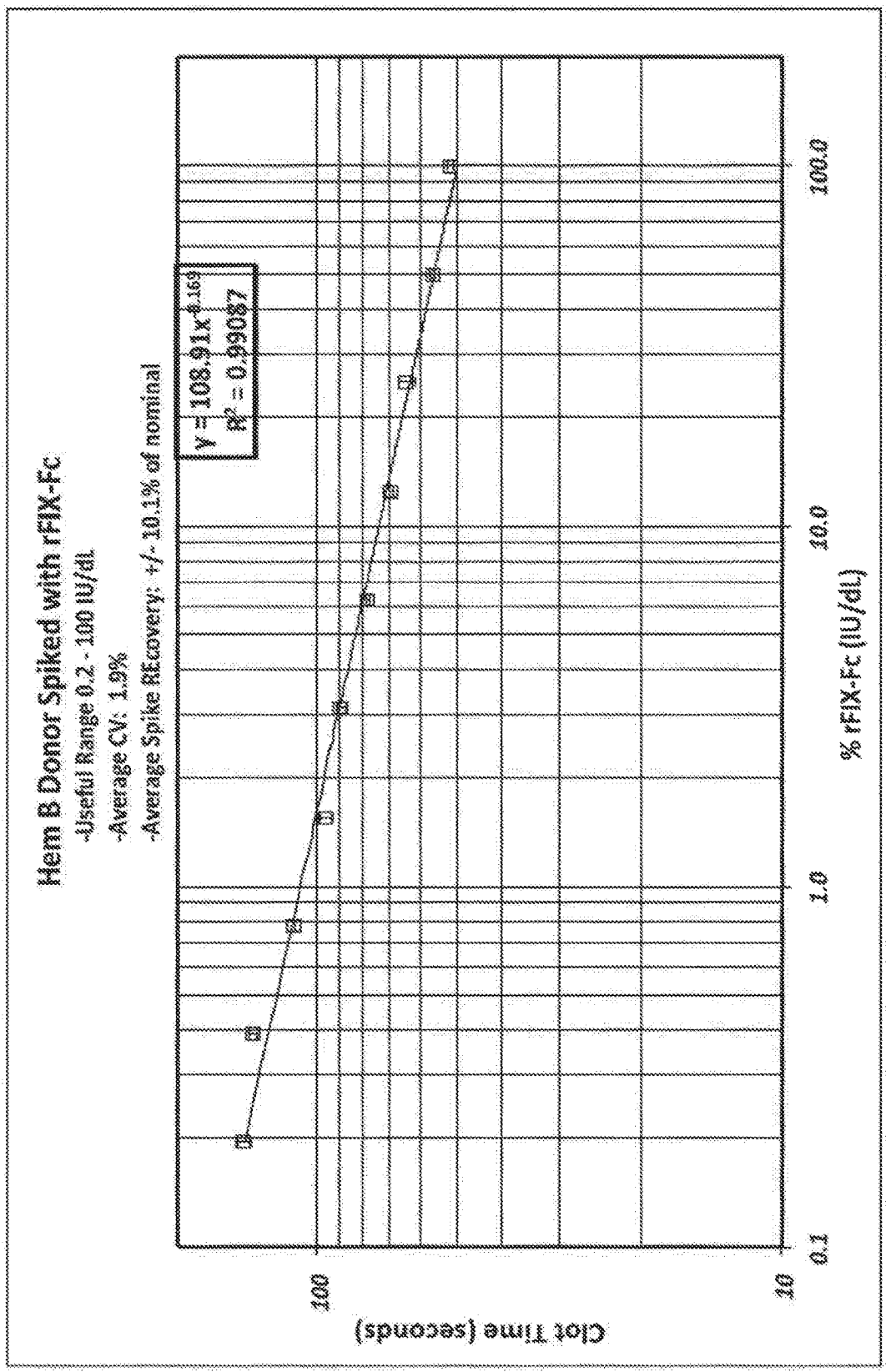

FIG. 4 shows clotting time for hemophilia B donor plasma spiked with rFIXFc measured using the Standard FMS Factor IX assay. FXIa/phospholipid was used as activator mixture. Samples consisted of 12 μL of re-calcified plasma applied directly (without preincubation) to the test bed.

Figure 5A:
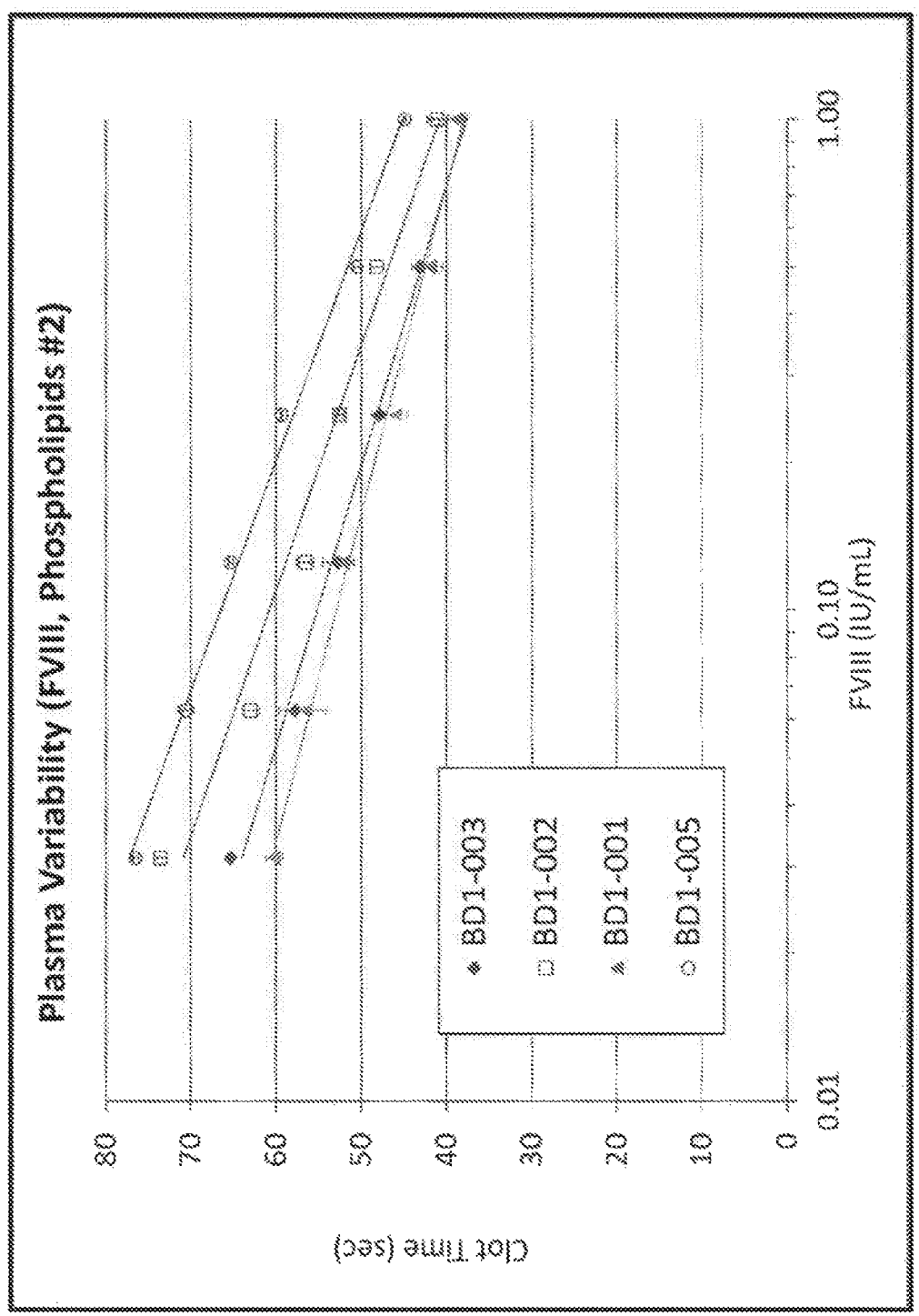

FIG. 5A shows clotting time determined using the Standard FMS Factor VIII assay using Phospholipid Blend 2 in the activated coagulation factor-phospholipid complex. Samples BD1-003, BD1-002, BD1-001 and BD1-005 were collected from 4 hemophilia A subjects and each sample was spiked with 6 levels of rFVIIIFc (100%, 50%, 25%, 12.5%, 6.3% and 3.1%).

Figure 5B:
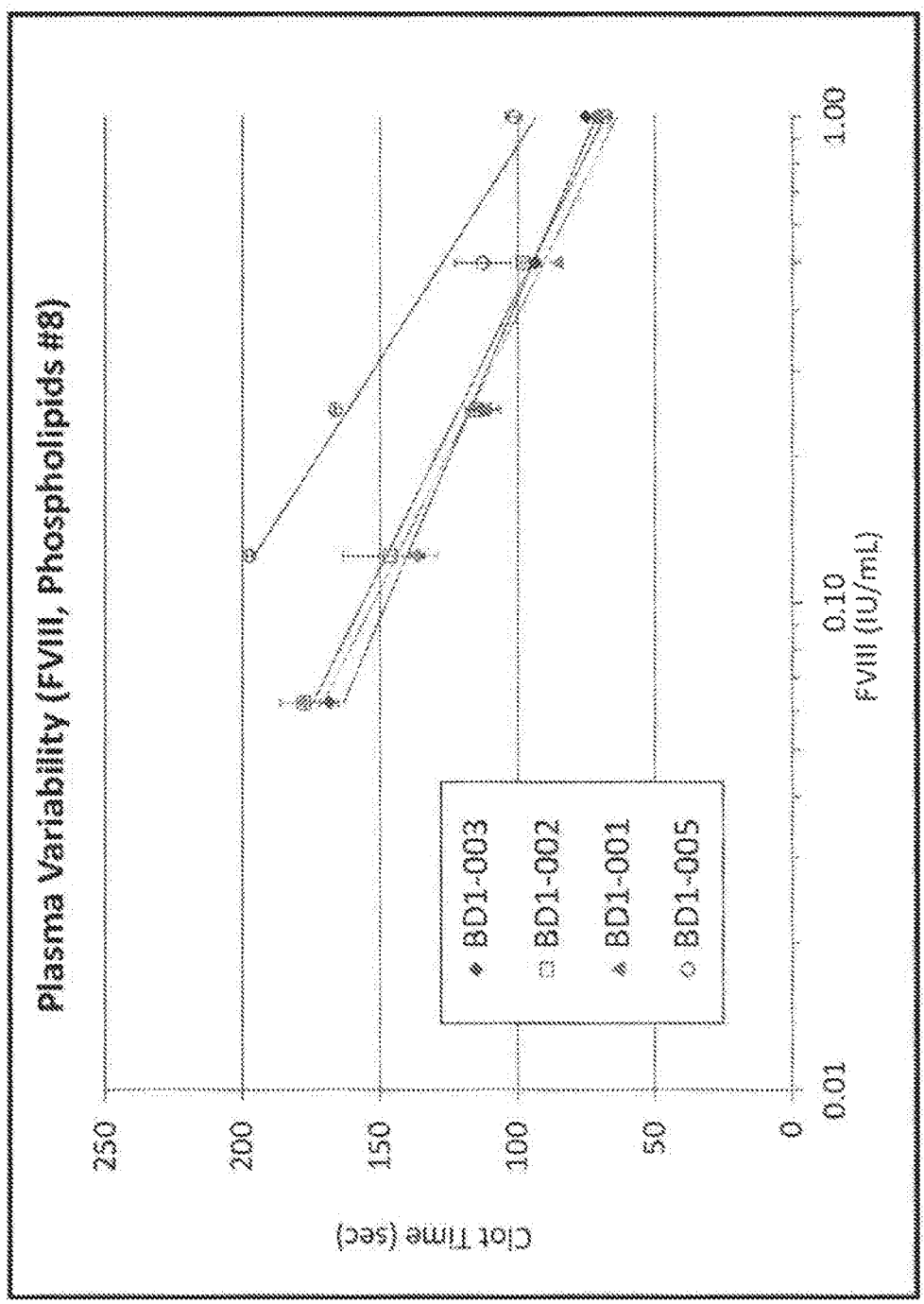

FIG. 5B shows clotting time determined using the Standard FMS Factor VIII assay using Phospholipid Blend 8 in the activated coagulation factor-phospholipid complex. Samples BD1-003, BD1-002, BD1-001 and BD1-005 were collected from 4 hemophilia A subjects and each sample was spiked with 6 levels of rFVIIIFc (100%, 50%, 25%, 12.5%, 6.3% and 3.1%).

Figure 6A:
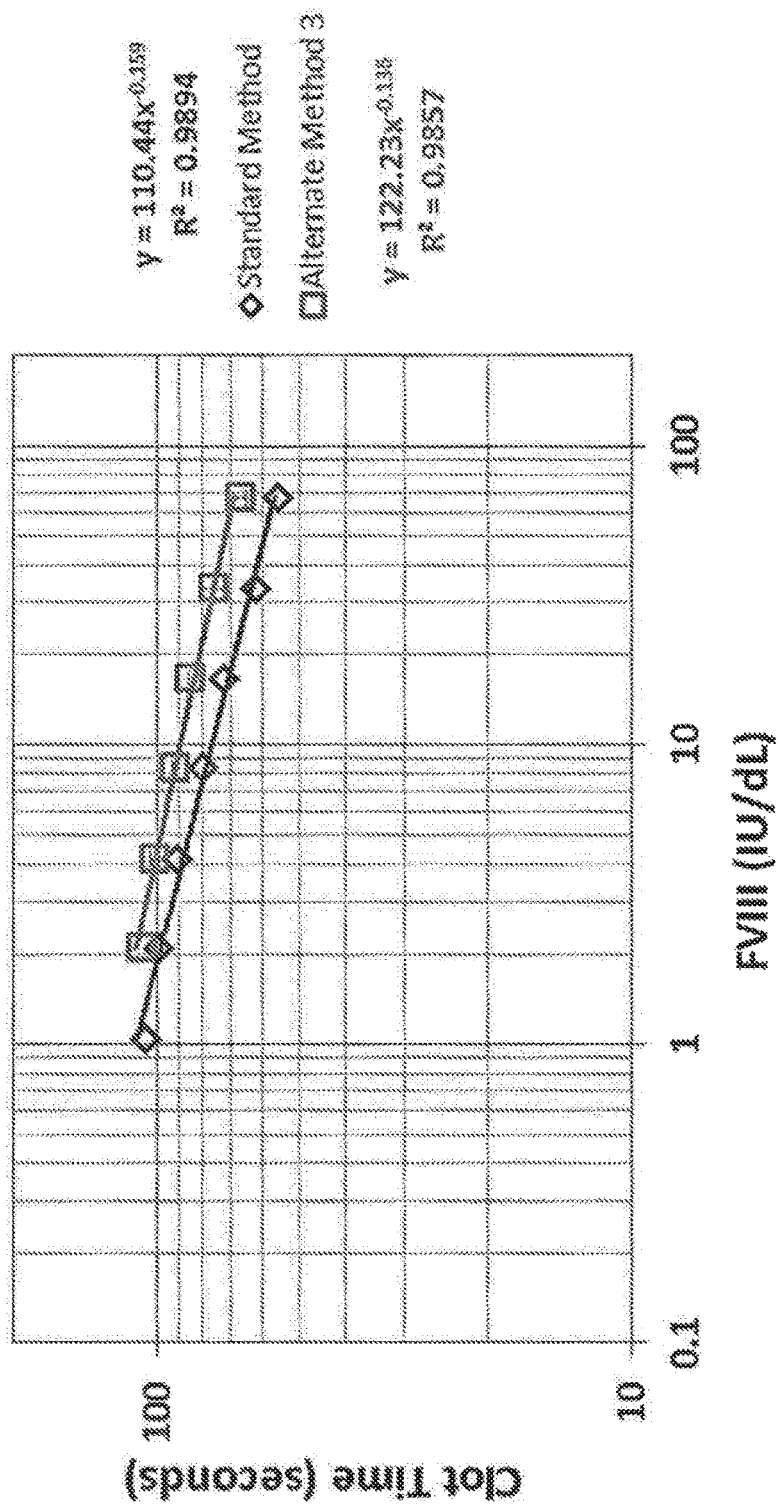

FIG. 6A shows a comparison of clotting time determined using the Standard FMS Factor VIII assay (Standard Method) and Alternate FMS Factor VIII assay (Alternate Method 3). Samples contained 12 μL of re-calcified plasma mixed 1:3 with substrate plasma (Factor VIII deficient plasma supplemented with defined levels of rFVIIIFc). Factor IXa/phospholipids complex was used as activator.

Figure 6B:
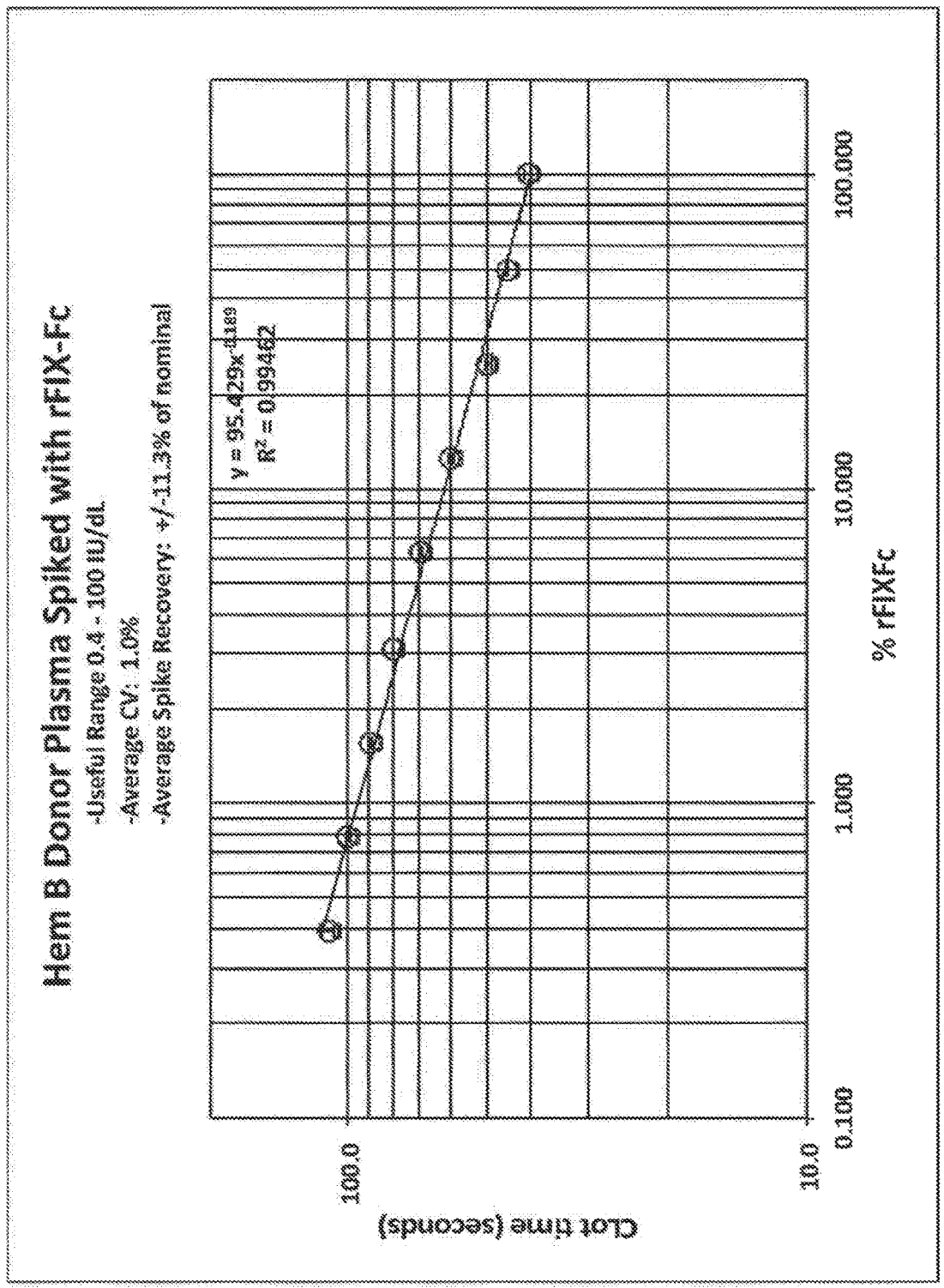

FIG. 6B shows clotting time measured using the Alternate FMS Factor IX assay (Alternate Method 9.8). Samples contained 12 μL of re-calcified plasma mixed 1:3 with substrate plasma (Factor IX deficient plasma supplemented with defined levels of rFIXFc). Factor XIa/phospholipids complex was used as activator.

Figure 7A:
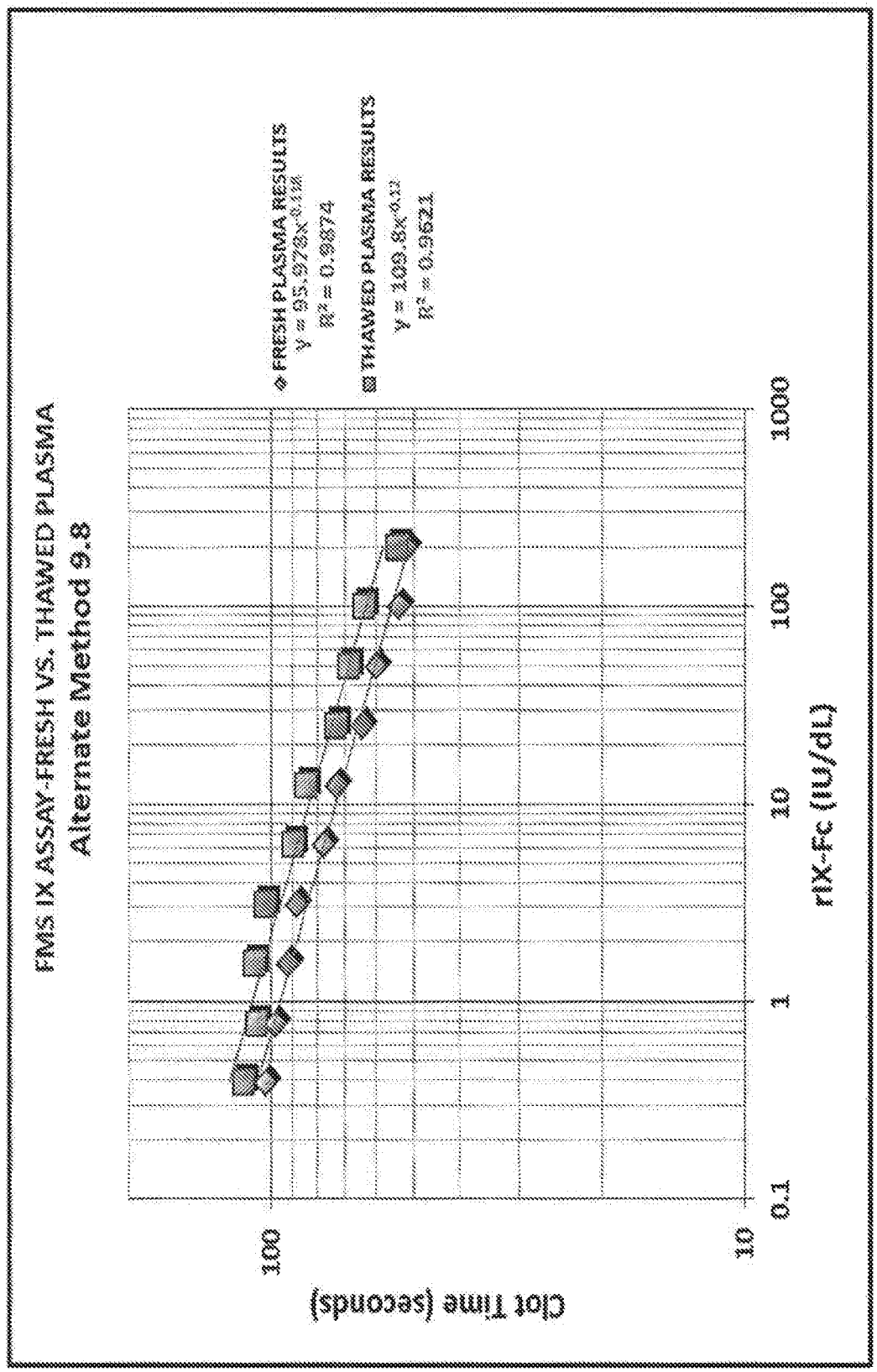

FIG. 7A shows the effect of a single plasma freeze-thaw cycle on Alternate FMS Factor IX assay performance. Samples contained 12 μL of re-calcified plasma mixed 1:3 with substrate plasma (Factor IX deficient plasma supplemented with defined levels of rFIXFc).

Figure 7B:
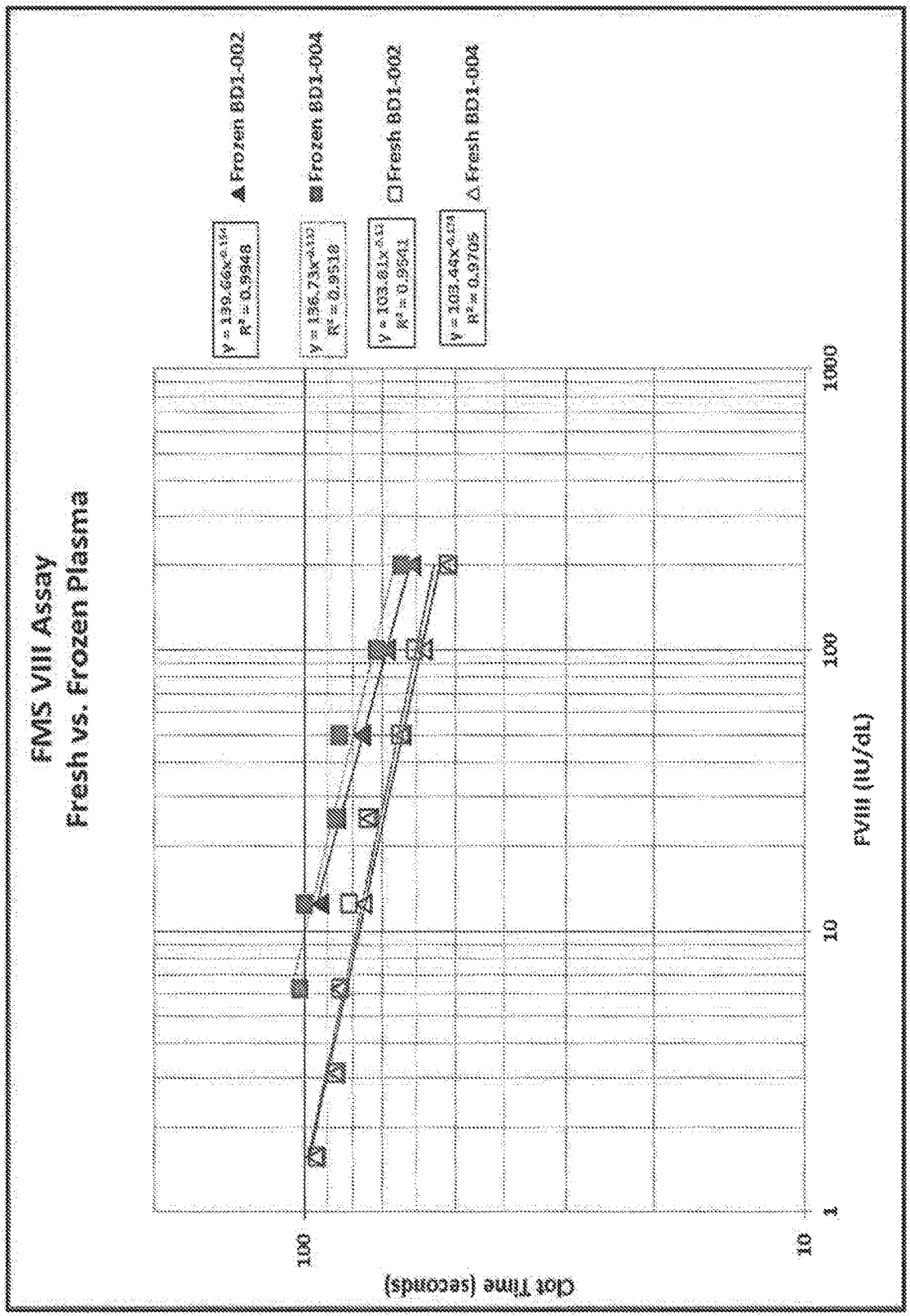

FIG. 7B shows clotting times corresponding to fresh plasma samples, and plasma subjected to a single plasma freeze-thaw cycle as measured using the Alternate FMS Factor VIII assay. Samples contained 12 μL of re-calcified plasma mixed 1:3 with substrate plasma (Factor VIII deficient plasma supplemented with defined levels of rFVIIIFc).

Figure 8A:
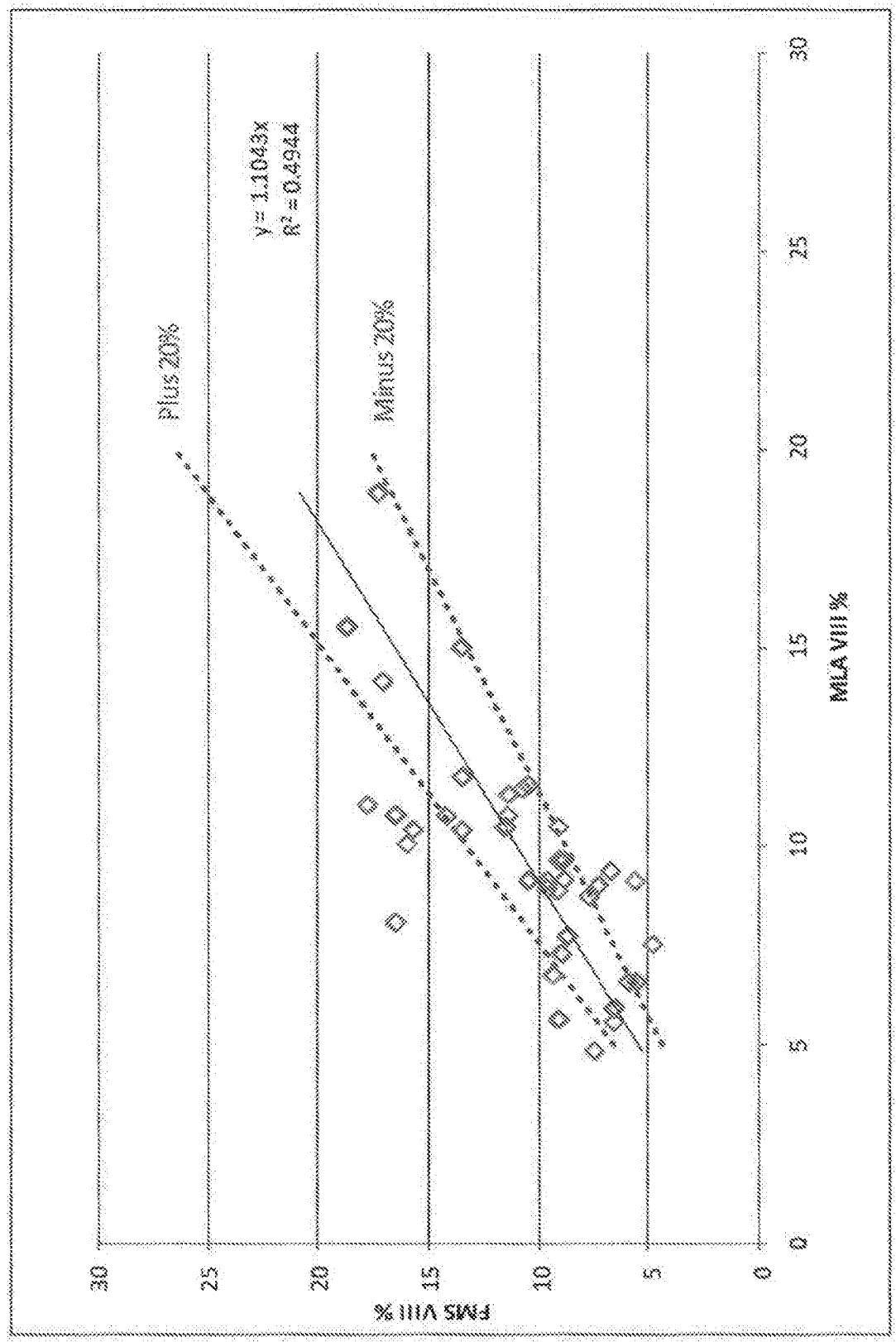

FIG. 8A shows the correlation between spiked rFVIIIFc levels measured using the Alternate FMS Factor VIII assay and rFVIIIFc levels measured by MLA. Citrated plasma samples from 14 hemophilia A donor were collected at 3 sites by 3 different methodologies, and spiked with varying levels of rFVIIIFc prior to being assayed using the Alternate FMS Factor VIII assay or MLA.

Figure 8B:
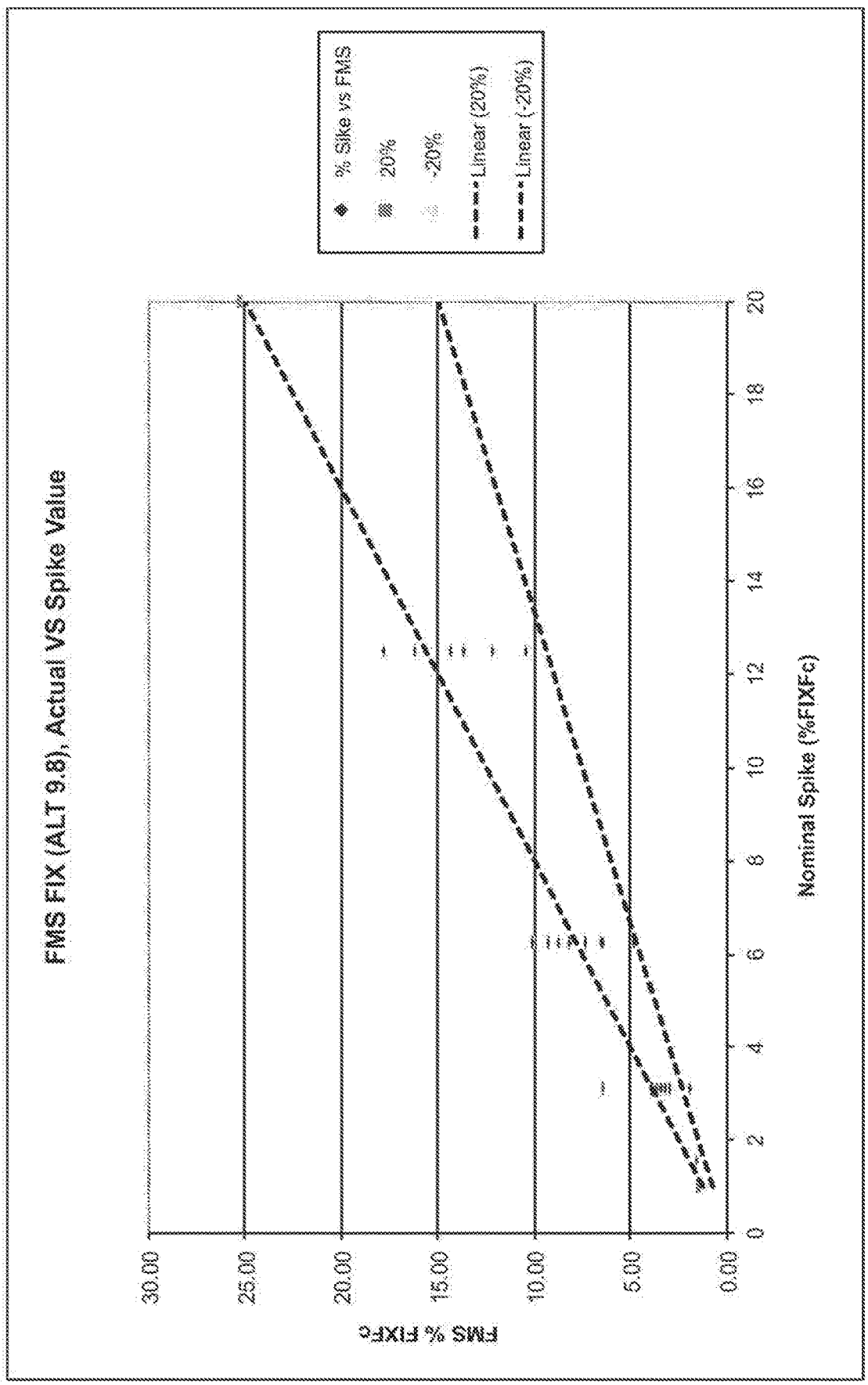

FIG. 8B shows the correlation between spiked rFXFc levels measured using the Alternate FMS FIX assays and rFIXFc levels measured by MLA. Citrated plasma samples from 9 hemophilia B donor were collected at 3 sites using 3 different methodologies, and spiked with varying levels of rFIXFc prior to being assayed using Alternate FMS FIX assay or MLA.

Figure 9A:
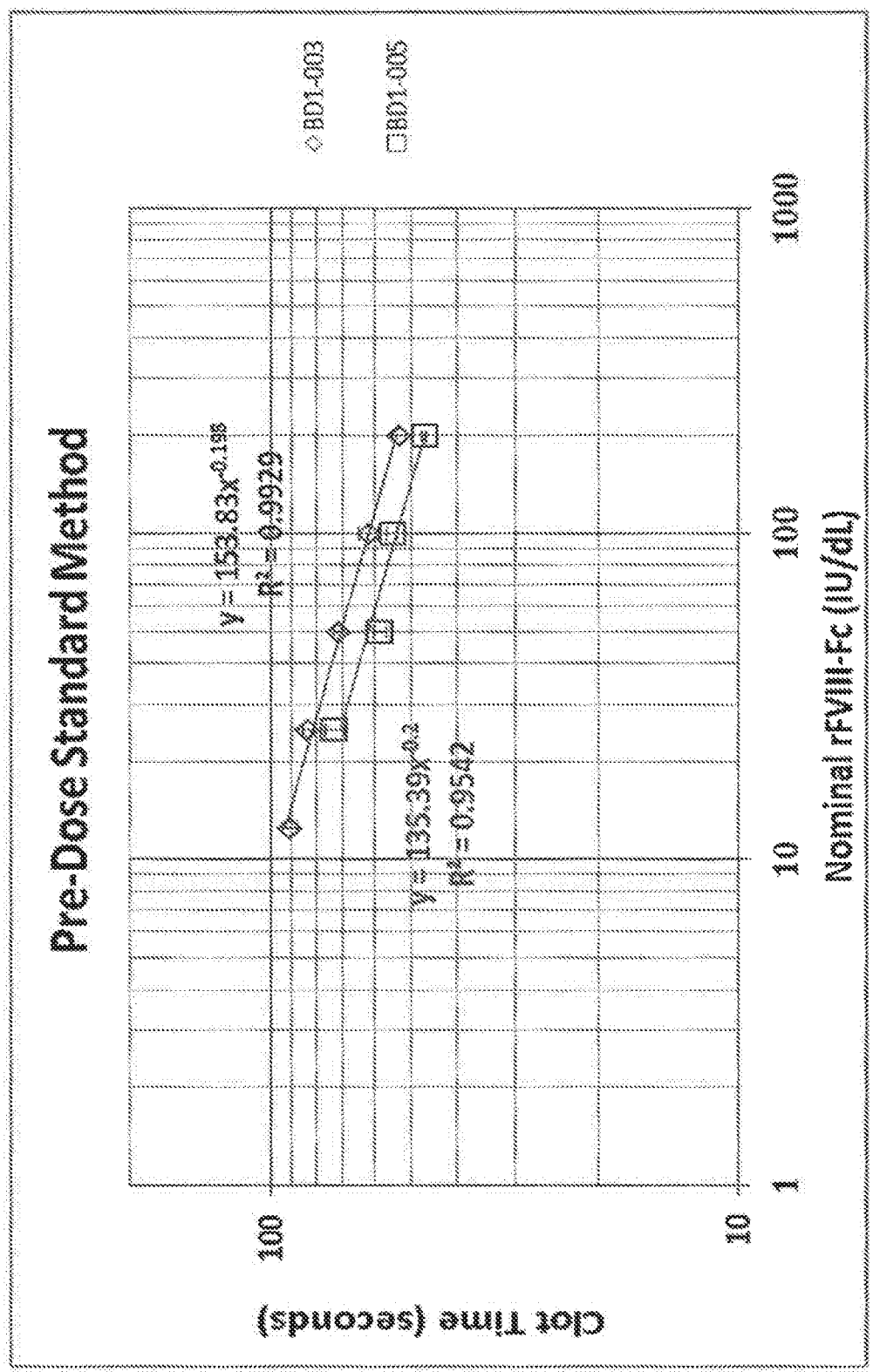

FIG. 9A shows clotting time results obtained by applying the Standard FMS FVIII assay to pre-dose whole blood samples obtained from two hemophilia A subjects (samples designated BD1-003 and BD1-005, respectively) spiked with increasing concentration of rFVIIIFc (0 IU/dl to 200 IU/dL).

Figure 9B:
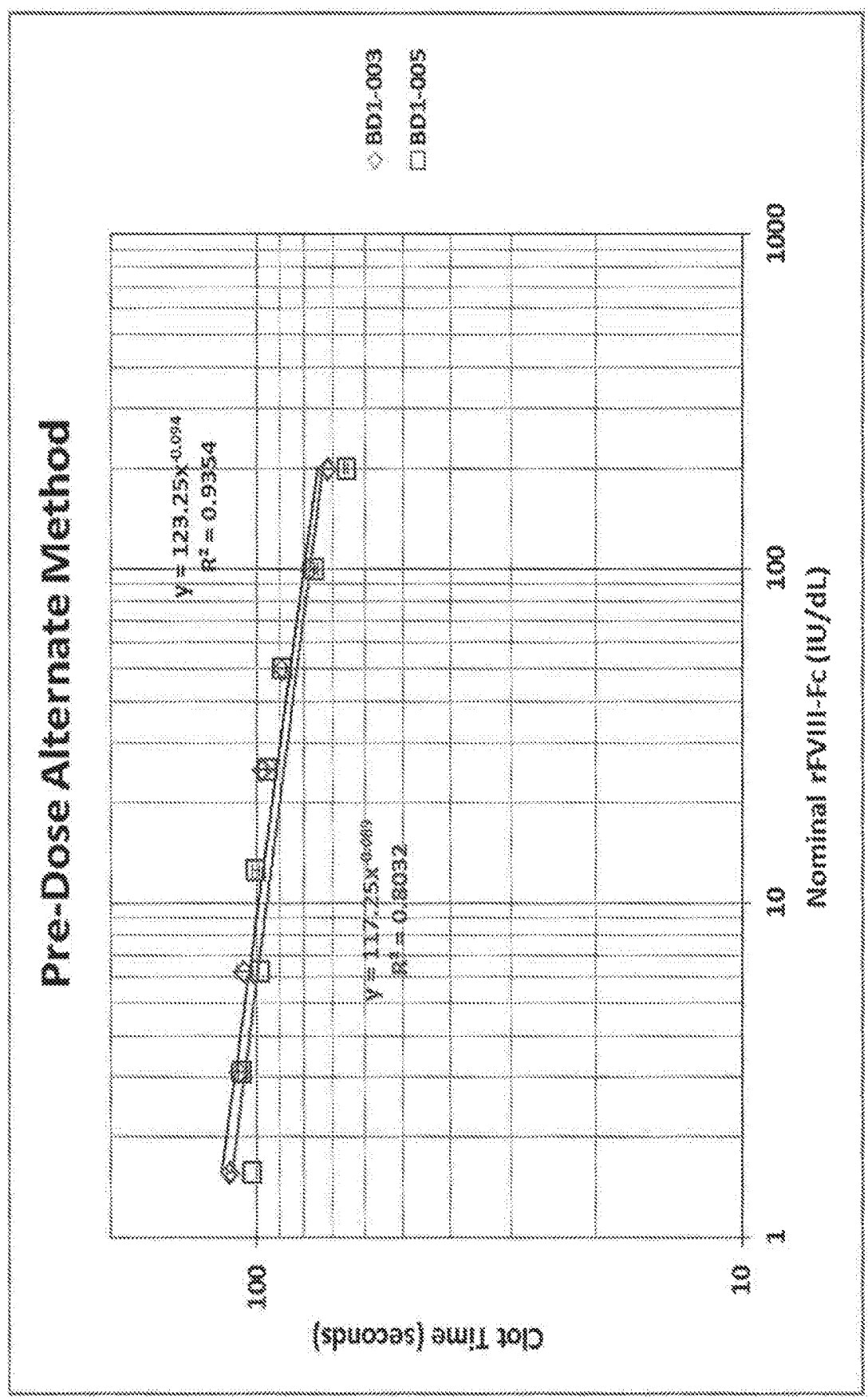

FIG. 9B shows clotting time results obtained by applying the Alternate FMS FVIII assay to pre-dose whole blood samples obtained from two hemophilia A subjects (samples designated BD1-003 and BD1-005, respectively) spiked with increasing concentration of rFVIIIFc (0 IU/dl to 200 IU/dL).

Figure 10A:
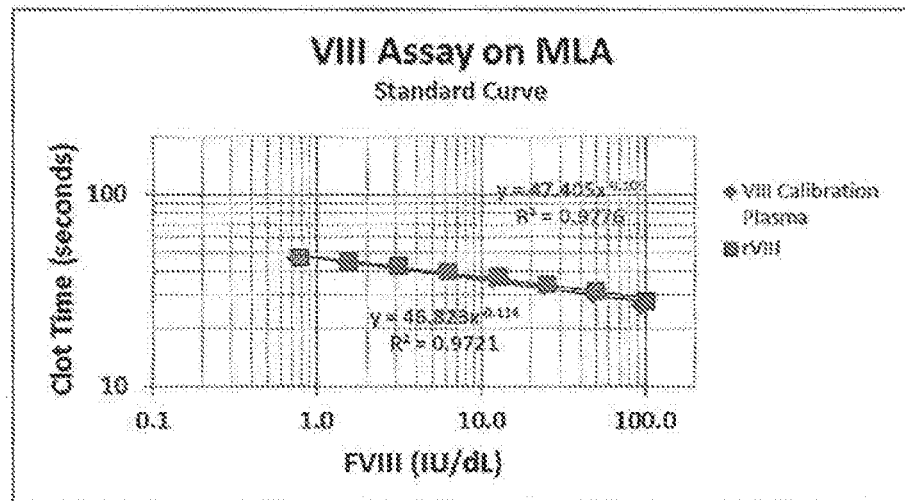
Figure 10B:
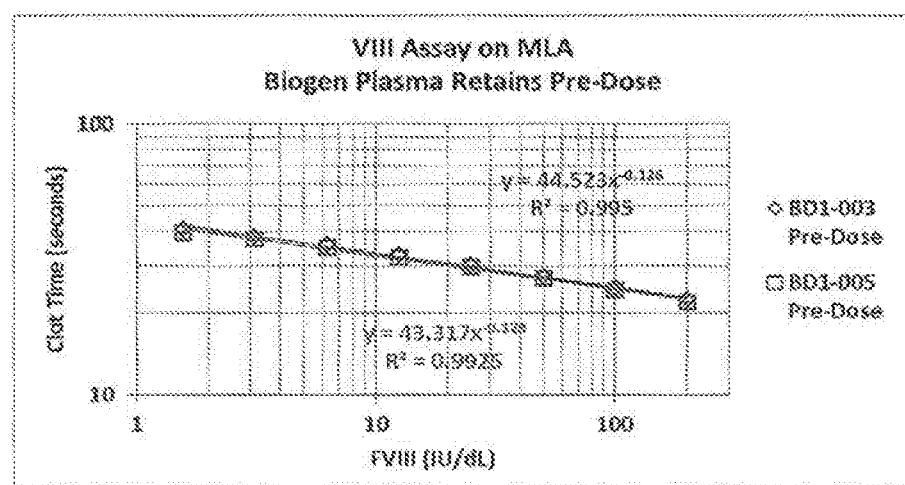
Figure 10C:
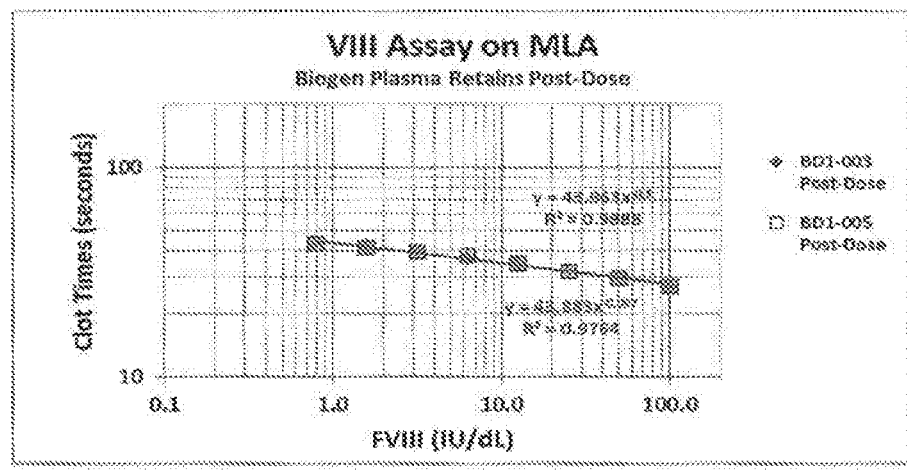

FIGS. 10A, 10B and 10C show clotting times obtained using MLA assay. Samples were frozen plasma retains prepared from the samples spiked with various concentration of rFVIIFc. FIG. 10A shows results corresponding to Factor VIII calibration plasma and rFVIIIFc samples. FIG. 10B shows results corresponding to pre-dose samples obtained from two hemophilia A subjects (samples designated BD1-003 and BD1-005, respectively) spiked with increasing concentration of rFVIIIFc. FIG. 10C shows results corresponding to post-dose samples obtained from two hemophilia A subjects (samples designated BD1-003 and BD1-005, respectively) spiked with increasing concentration of rFVIIIFc.

FIGS. 11A and 11B show, respectively, Standard FMS Factor VIII assay measurements conducted on frozen plasma retains of pre-dose (FIG. 11A) and post-dose (FIG. 11B) samples obtained from two hemophilia A subjects (samples designated BD1-003 and BD1-005, respectively) spiked with increasing concentration of rFVIIIFc.

FIGS. 12A and 12B show, respectively, Alternate FMS Factor VIII assay measurements conducted on frozen plasma retains of pre-dose (FIG. 12A) and post-dose (FIG. 12B) samples obtained from two hemophilia A subjects (samples designated BD1-003 and BD1-005, respectively) spiked with increasing concentration of rFVIIIFc.

Figure 13:
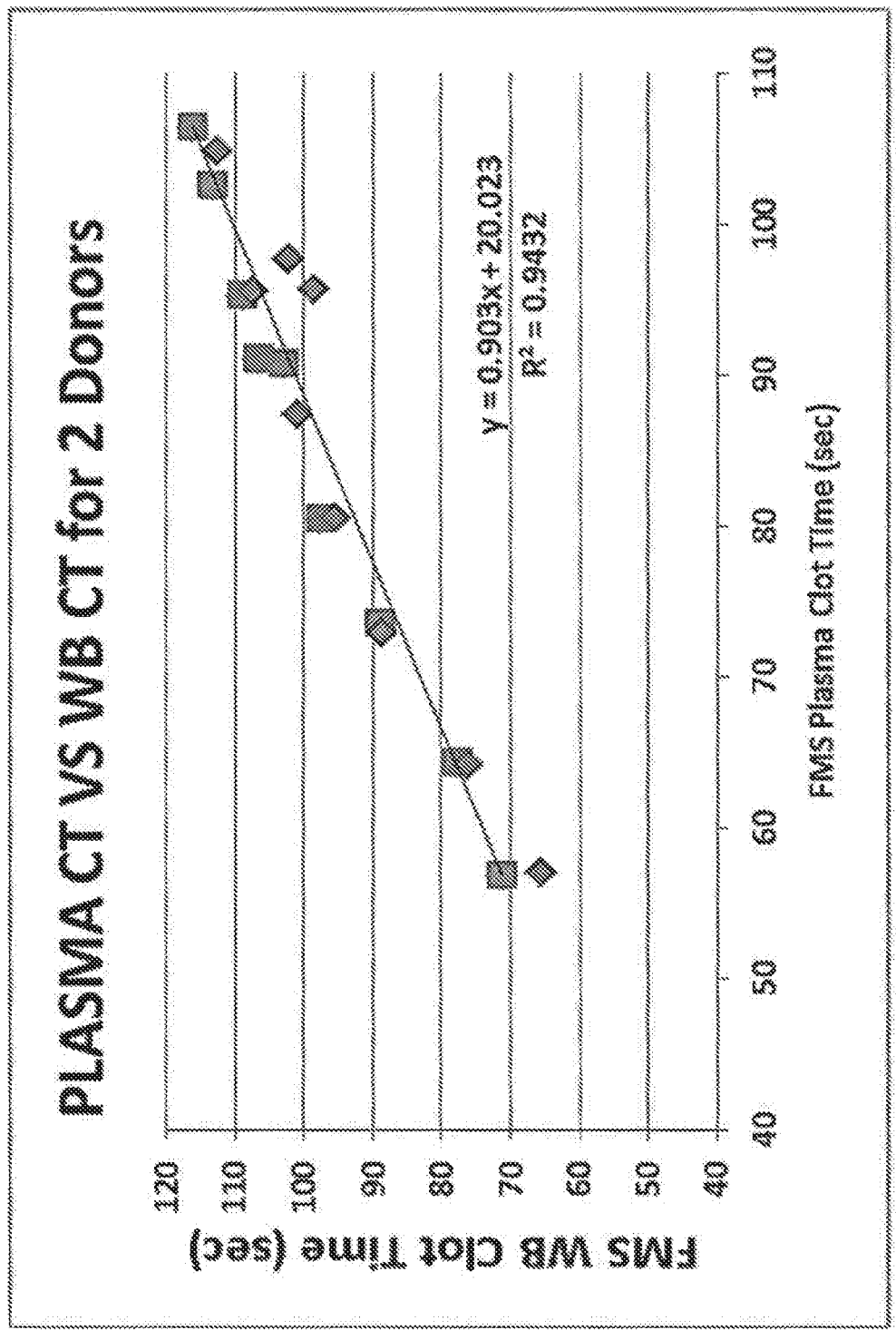

FIG. 13 shows the correlation between whole blood clotting and plasma clotting time measurements performed using the Alternate FMS FVIII assay.

FIG. 14A compares Alternate FMS Factor VIII assay clotting times for plasma and whole blood samples obtained from two patients (BD1-002 and BD1-004). FIG. 14B shows the correlation between whole blood clotting time and plasma clotting time measurements performed using the Alternate FMS FVIII assay. Pre-dose blood samples were spiked with increasing concentrations of rFVIIIFc (0 IU/dL-200 IU/dL).

Figure 15A:
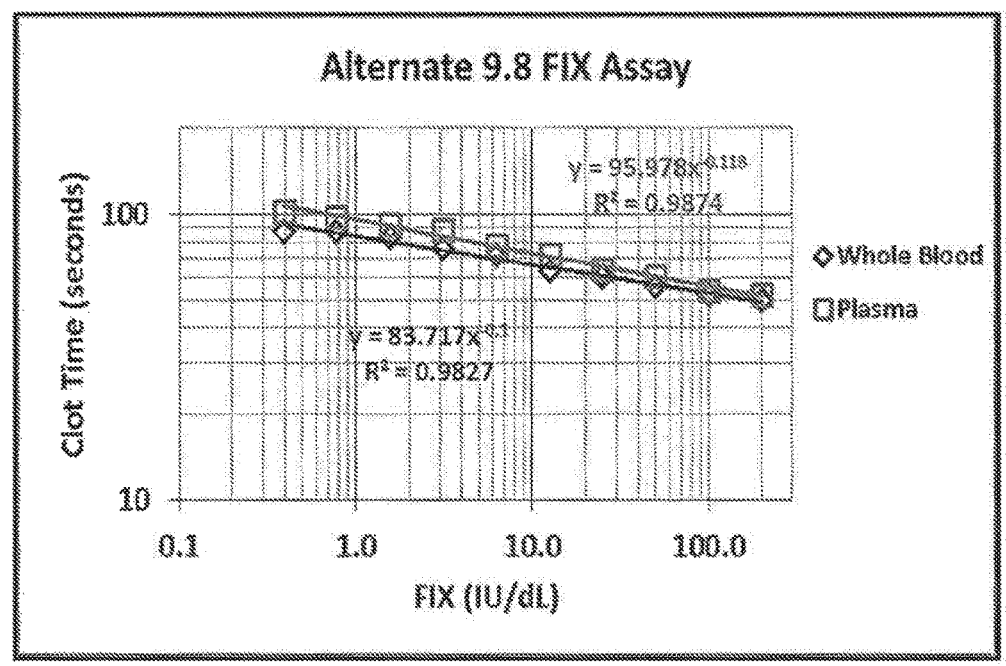
Figure 15B:
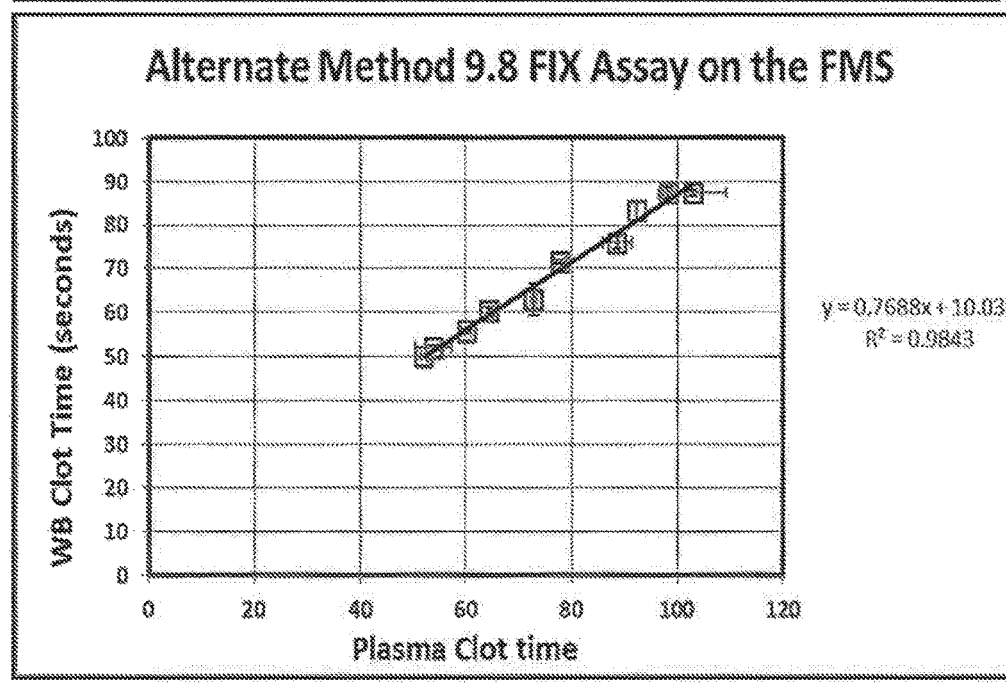

FIG. 15A compares Alternate FMS Factor IX assay clotting times for plasma and whole blood samples. FIG. 15B shows the correlation between whole blood clotting time and plasma clotting time using the Alternate FMS FIX assay. Pre-dose blood samples were spiked with increasing concentration of rFIXFc (0 IU/dL-200 IU/dL).

Figure 16:
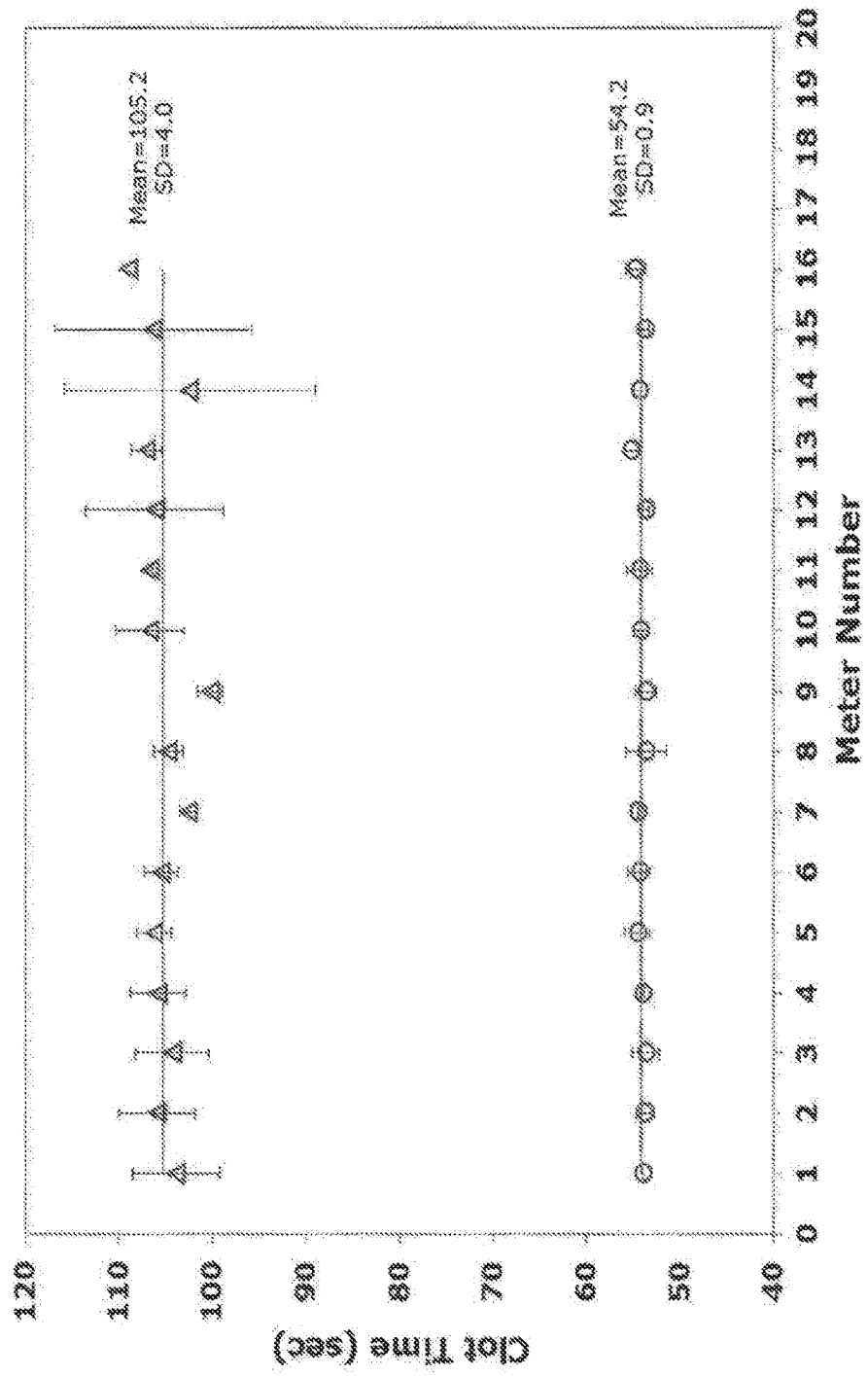

FIG. 16 shows the variability between meters assaying a single FVIII deficient plasma sample spiked to 100% (triangles) and 3% (circles) rFVIIIFc in duplicate on 16 research meters using the Alternate FMS FVIII assay.

Figure 17:
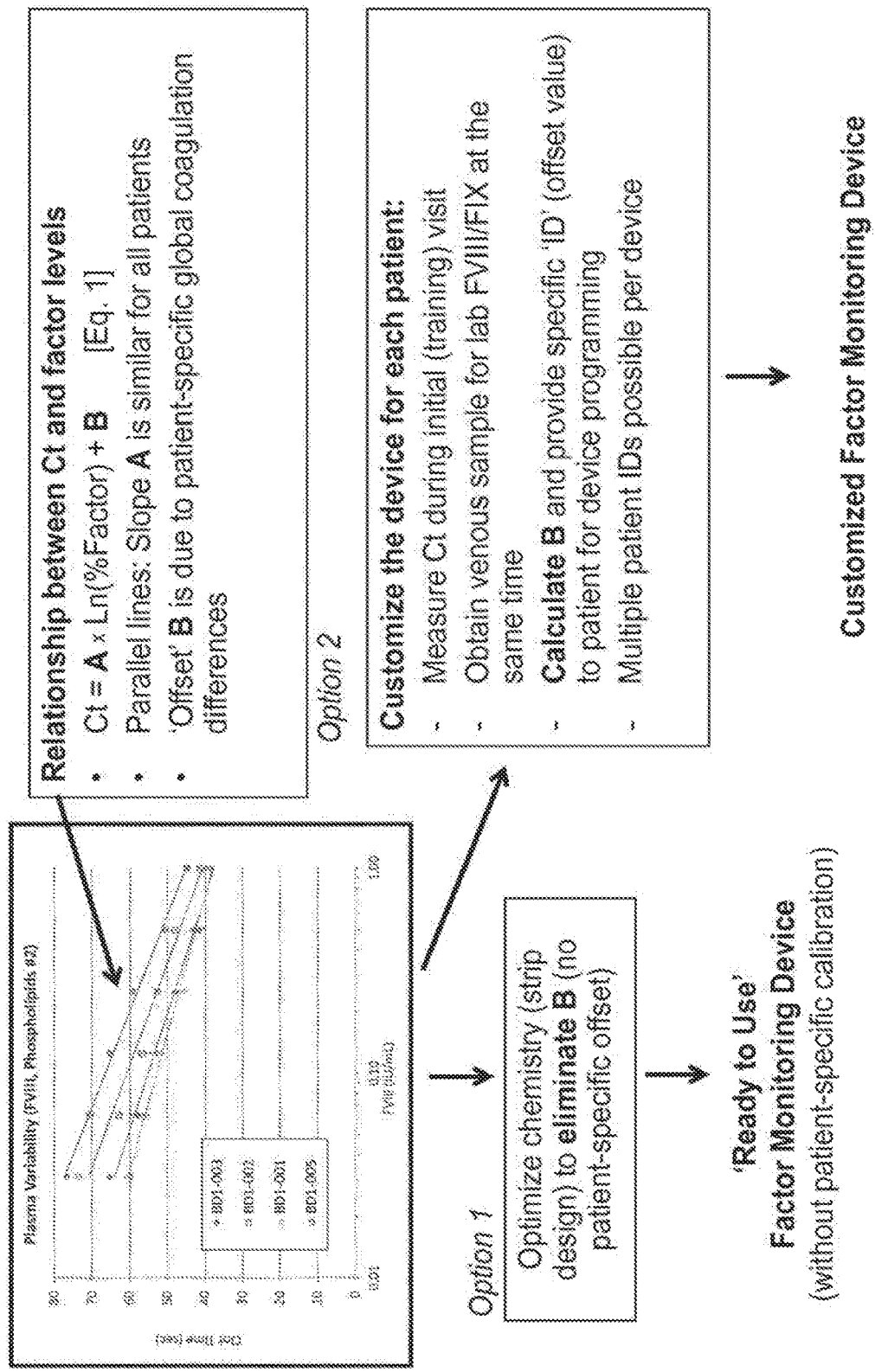

FIG. 17 provides a diagram showing the correlation between coagulation factor concentration (% Factor) and clotting time (Ct) from FMS assays, and the application of such correlation to a point-of-care device.

Figure 18:
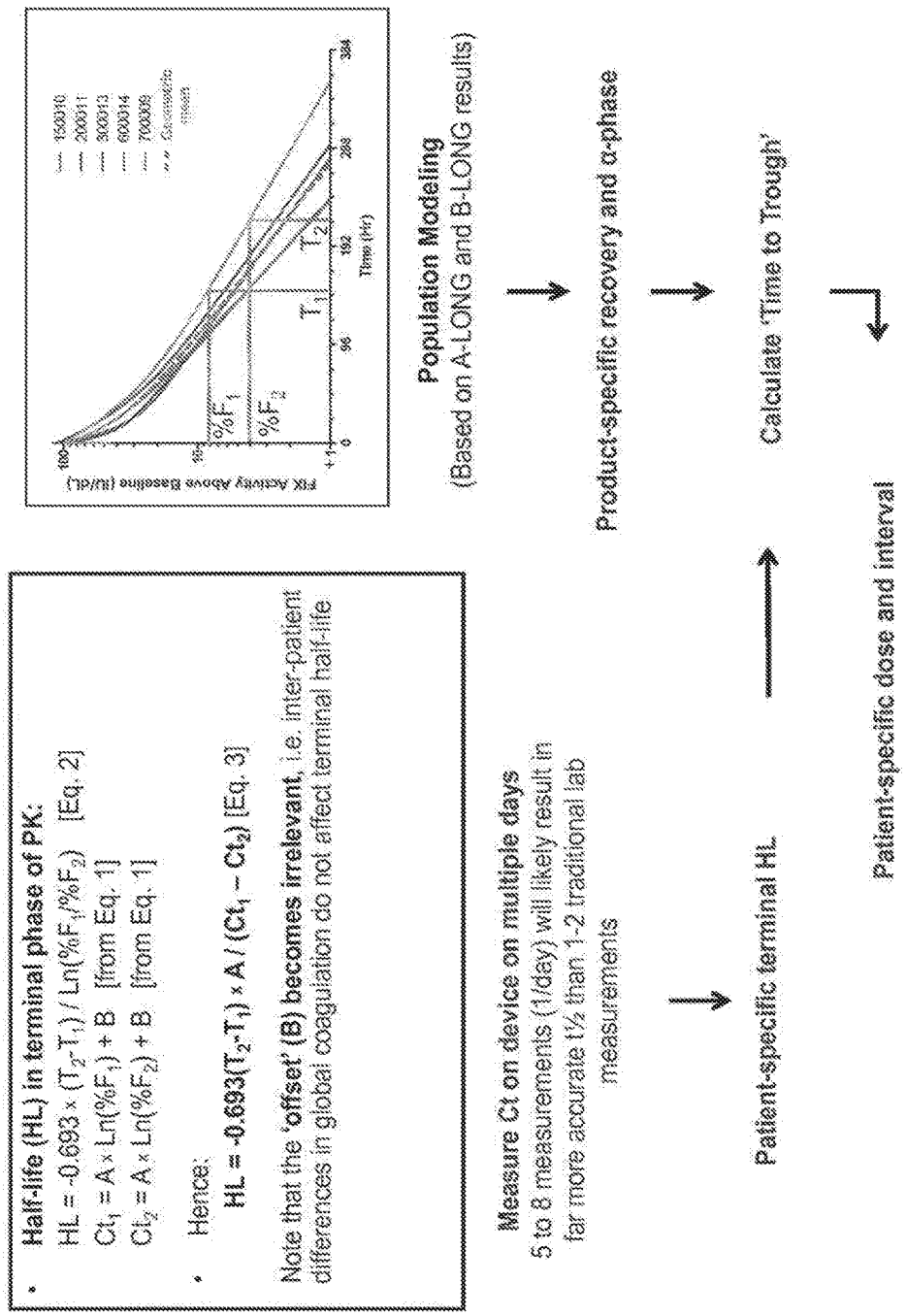

FIG. 18 provides a diagram showing the calculation of terminal half-life from data obtained from FMS assays and its integration with pharmacokinetics data to calculate time to trough and determine patient-specific doses and interval between doses.

DETAILED DESCRIPTION

The present disclosure provides methods and compositions for diagnosing and treating subject having a bleeding disorder. The disclosed methods comprise contacting a sample, e.g., a blood sample or a plasma sample obtained from the patient, with an activation mixture comprising an activated coagulation factor and a phospholipid mixture, wherein the activation mixture is dried onto a solid substrate. In some aspects, the time between the contacting of the activation mixture with the blood sample and the onset of clotting, i.e., the clotting time (Ct), is used to calculate pharmacokinetic parameters which in turn can be used to commence, modify, or cease treatment with coagulation factors. Certain FVIII and FIX polypeptides for use in the methods provided herein are described in International Application No. PCT/US2010/059136, filed Dec. 6, 2010, and in International Application No. PCT/US2011/043569, filed Jul. 11, 2011, each of which is herein incorporated by reference in its entirety.

I. Definitions

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

"Administering," as used herein, refers to giving a pharmaceutically acceptable amount of a therapeutic agent such as a coagulation factor, e.g., Factor VIII or Factor IX polypeptide, to a subject via a pharmaceutically acceptable route. Routes of administration include intravenous, e.g., intravenous injection and intravenous infusion, e.g., via central venous access. Additional routes of administration include subcutaneous, intramuscular, oral, nasal, and pulmonary administration. In some aspects, the administration is subcutaneous. Coagulation factors, e.g., Factor VIII and Factor IX, including fragments, variants, derivatives, chimeric polypeptides, or hybrid polypeptide can be administered as part of a pharmaceutical composition comprising at least one excipient. The term administering also refers to giving any other therapeutic agent or prophylactic agent (e.g., a small molecule) that can be given in a pharmaceutically acceptable amount to a subject having a coagulation-related disorder via a pharmaceutically acceptable route.

The term "sequence" as used to refer to a protein sequence, a peptide sequence, a polypeptide sequence, or an amino acid sequence means a linear representation of the amino acid constituents in the polypeptide in an amino-terminal to carboxyl-terminal direction in which residues that neighbor each other in the representation are contiguous in the primary structure of the polypeptide.

By a "protein" or "polypeptide" is meant any sequence of two or more amino acids linearly linked by amide bonds (peptide bonds) regardless of length, post-translation modification, or function. As used herein, the term "polypeptide" is intended to encompass a singular "polypeptide" as well as plural "polypeptides." "Polypeptide," "peptide," and "protein" are used interchangeably herein. Thus, peptides, dipeptides, tripeptides, or oligopeptides are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. A polypeptide can be generated in any manner, including by chemical synthesis. Also included as polypeptides of the present disclosure are fragments, derivatives, analogs, or variants of the foregoing polypeptides, and any combination thereof.

The term "fragment" when referring to polypeptides and proteins, e.g., coagulation factors such as Factor VIII or Factor IX, include any polypeptides or proteins which retain at least some of the properties of the reference polypeptide or protein. E.g., in the case of procoagulant polypeptides such as coagulation factors and procoagulant peptides, the term fragment would refer to any polypeptides or proteins which retain at least some of the procoagulant activity of the reference polypeptide or protein. Fragments of polypeptides include proteolytic fragments, as well as deletion fragments.

The term "variant" as used herein refers to a polypeptide sequence that differs from that of a parent polypeptide sequence by virtue of at least one amino acid modification. Variants can occur naturally or be non-naturally occurring. Non-naturally occurring variants can be produced using art-known mutagenesis techniques. Variant polypeptides can comprise conservative or non-conservative amino acid substitutions, deletions, or additions.

"Derivatives" of polypeptides or proteins of the present disclosure are polypeptides or proteins which have been altered so as to exhibit additional features not found on the native polypeptide or protein. Also included as "derivatives" are those peptides that contain one or more naturally occurring amino acid derivatives of the twenty standard amino acids. A polypeptide or amino acid sequence "derived from" a designated polypeptide or protein refers to the origin of the polypeptide. Preferably, the polypeptide or amino acid sequence which is derived from a particular sequence has an amino acid sequence that is essentially identical to that sequence or a portion thereof, wherein the portion consists of at least 10-20 amino acids, preferably at least 20-30 amino acids, more preferably at least 30-50 amino acids, or which is otherwise identifiable to one of ordinary skill in the art as having its origin in the sequence.

Polypeptides derived from another peptide can have one or more mutations relative to the starting polypeptide, e.g., one or more amino acid residues which have been substituted with another amino acid residue or which has one or more amino acid residue insertions or deletions. Preferably, the polypeptide comprises an amino acid sequence which is not naturally occurring. Such variants necessarily have less than 100% sequence identity or similarity with the starting polypeptide. In one aspect, the variant will have an amino acid sequence from about 75% to less than 100% amino acid sequence identity or similarity with the amino acid sequence of the starting polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule. In one aspect, there is one amino acid difference between a starting polypeptide sequence and the sequence derived therefrom. Identity or similarity with respect to this sequence is defined herein as the percentage of amino acid residues in the candidate sequence that are identical (i.e. same residue) with the starting amino acid residues, after aligning the sequences and introducing gaps, if necessary, to achieve the maximum percent sequence identity.

A polypeptide which is "isolated" is a polypeptide which is in a form not found in nature. Isolated polypeptides include those which have been purified to a degree that they are no longer in a form in which they are found in nature. In some aspects, a polypeptide which is isolated is substantially pure.

A "recombinant" polypeptide or protein refers to a polypeptide or protein produced via recombinant DNA technology. Recombinantly produced polypeptides and proteins expressed in host cells are considered isolated for the purpose of the invention, as are native or recombinant polypeptides which have been separated, fractionated, or partially or substantially purified by any suitable technique. The polypeptides disclosed herein, e.g., clotting factors, can be recombinantly produced using methods known in the art. Alternatively, proteins and peptides disclosed herein can be chemically synthesized.

A "conservative amino acid substitution" is one in which the amino acid residue is replaced with an amino acid residue having a similar side chain. Families of amino acid residues having similar side chains have been defined in the art, including basic side chains (e.g., Lys, Arg, His), acidic side chains (e.g., Asp, Glu), uncharged polar side chains (e.g., Gly, Asn, Gnl, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Tyr, Phe, Trp, His). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, He, Phe or Val), (iii) a cysteine or proline is substituted for, or by, any other residue, or (iv) a residue having a bulky hydrophobic or aromatic side chain (e.g., Val, He, Phe or Trp) is substituted for, or by, one having a smaller side chain (e.g., Ala, Ser) or no side chain (e.g., Gly).

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

"Polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include those in Sequence Table 1, which encode the polypeptides of Sequence Table 2 (see Sequence Table 1). Polynucleotides also include fragments of the polynucleotides of Table 1, e.g., those that encode fragments of the polypeptides of Table 2, such as Factor VIII, Factor IX, Fc, signal sequence, propeptide, 6His and other fragments of the polypeptides of Sequence Table 2.

The terms "subject" and "patient" are used interchangeably and refer to a human or a non-human mammal, for whom diagnosis, prognosis, or therapy of a bleeding disorder is desired. Non-human mammals include mice, dogs, primates, bears, cats, horses, cows, pigs, and other domestic animals and small animals. Subjects also include pediatric humans. Pediatric human subjects are birth to 20 years, e.g., birth to 18 years, birth to 16 years, birth to 15 years, birth to 12 years, birth to 11 years, birth to 6 years, birth to 5 years, birth to 2 years, or 2 to 11 years of age. In some aspects of the present disclosure, a subject is a naïve subject. A naïve subject is a subject that has not been administered a treatment for a bleeding disorder. In some aspects, a naïve subject has not been treated with prior to being diagnosed with having a bleeding disorder.

The methods disclosed herein can be practiced on a subject in need of control or prevention of bleeding, bleeding episodes, or hemophilia disorders. Such subjects include those in need of control or prevention of bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those need of peri-operative management, such as management of bleeding associated with surgery or dental extraction.

The term "bleeding disease or disorder," as used herein, means a genetically inherited or acquired condition characterized by a tendency to hemorrhage, either spontaneously or as a result of trauma, due to an impaired ability or inability to form a fibrin clot. Examples of such disorders include hemophilias. The three main forms are hemophilia A (factor VIII deficiency), hemophilia B (factor IX deficiency or "Christmas disease") and hemophilia C (factor XI deficiency, mild bleeding tendency). Other hemostatic disorders include, e.g., von Willebrand disease, Factor XI deficiency (PTA deficiency), Factor XII deficiency, deficiencies or structural abnormalities in fibrinogen, prothrombin, Factor V, Factor VII, Factor X or factor XIII, Bernard-Soulier syndrome, which is a defect or deficiency in GPIb. GPIb, the receptor for vWF, can be defective and lead to lack of primary clot formation (primary hemostasis) and increased bleeding tendency), and thrombasthenia of Glanzman and Naegeli (Glanzmann thrombasthenia). In liver failure (acute and chronic forms), there is insufficient production of coagulation factors by the liver; this can increase bleeding risk.

Bleeding disease or disorder can require on-demand treatment or prophylactic treatment. "On-demand treatment," as used herein, means treatment that is intended to take place over a short course of time and is in response to an existing condition, such as a bleeding episode, or a perceived short term need such as planned surgery. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, pen-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for pen-operative management for surgery or dental extraction, major surgery, extensive oral surgery, urologic surgery, hernia surgery, orthopedic surgery such as replacement of knee, hip, or other major joint.

The terms "prophylactic treatment" or "prophylaxis" as used herein, mean administering a procoagulant compound, e.g., a clotting factor, fragment, variant, derivative, chimeric peptide, or hybrid peptide thereof, to a subject over a course of time to increase the level of activity in a subject's plasma. Preferably, the increased level is sufficient to decrease the incidence of spontaneous bleeding or to prevent bleeding, e.g., in the event of an unforeseen injury. Preferably, during prophylactic treatment, the plasma protein level in the subject does not fall below the baseline level for that subject, or below the level that characterizes severe hemophilia.

The term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" is used herein to modify a numerical value above and below the stated value by a variance of 10 percent, up or down (higher or lower).

The term "pharmacokinetic parameters" or "PK parameters" as used herein refers to those constant and variable terms that are related to the disposition of a pharmacologically active agent, e.g., a coagulation factor, within a subject and includes for example volume of distribution, total clearance, metabolic clearance, bioavailability, intrinsic clearance, mean residence time, partitioning coefficients between tissues and blood, elimination rates, half-life, terminal half-life, time to trough, as well as other parameters known in the art. PK parameters can be based, e.g., on protein level or activity level. In addition, certain PK parameters can be based on model predicted data, on observed data, or on combinations of model and observed data.

As used herein, the term "clotting factor," refers to molecules, fragment, derivatives, or analogs thereof, naturally occurring or recombinantly produced, which prevent or decrease the duration of a bleeding episode in a subject. In other words, it means molecules having pro-clotting or pro-coagulant activity, i.e., are responsible for the conversion of fibrinogen into a mesh of insoluble fibrin causing the blood to coagulate or clot. The term "clotting factor" as used herein also encompasses synthetic peptides with procoagulant activity.

The term "clotting time" as used herein, refers to the time period elapsed from the time when the sample is contacted with the activating mixture until the time when the sample clots.

"Half-Life" as used herein, refers to a biological half-life of a particular therapeutic agent in vivo. Terminal half-life can be represented by the time required for half the quantity administered to a subject to be cleared from the circulation and/or other tissues in the subject. When a clearance curve of a given polypeptide is constructed as a function of time, the curve is usually biphasic with a rapid α-phase and longer β-phase. The α-phase typically represents an equilibration of the administered chimeric polypeptide between the intra- and extra-vascular space and is, in part, determined by the size of the polypeptide. The β-phase typically represents the catabolism of the polypeptide in the intravascular space.

The term "terminal plasma half-life" or "terminal half-life" refers to the time required to divide the plasma concentration by two after reaching pseudo-equilibrium. The terminal half-life is especially relevant to multiple dosing regimens, because it controls the degree of therapeutic agent accumulation, concentration fluctuations, and the time taken to reach equilibrium.

"Trough," as used herein, is the lowest plasma activity level reached after administering a dose of a pharmacologically active agent, e.g., a clotting factor such as Factor VIII or Factor IX, a fragment, a derivative or an analog thereof, before the next dose is administered, if any. Accordingly, "time to trough" (T) is the time at which the lowest plasma activity level is reached after administering a pharmacologically active agent before the next dose is administered.

The term "sample" as used herein includes any biological fluid or issue, such as whole blood or serum, obtained from a subject which contains or is suspected to contain a blood coagulation factor. In some specific aspects, that sample is blood or a fraction thereof, muscle, skin, or a combination thereof. Samples can be obtained by any means known in the art.

In order to apply the methods and systems of the disclosure, samples from a patient can be obtained before or after the administration of a therapy to treat a bleeding disorder. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of clotting times and/or PK parameters derived from clotting times, comparisons between clotting times and/or PK parameters derived from clotting times, evaluation of the clotting times and/or PK parameters derived from clotting time, and treatment decisions can be performed by one or more healthcare providers, healthcare benefits providers, and/or clinical laboratories.

As used herein, the term "healthcare provider" refers to individuals or institutions which directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer a therapy to treat a bleeding disease or disorder. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy or therapeutic agent (e.g., a clotting factor such as a Factor VIII or Factor IX polypeptide), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits providers can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, The above enumerated actions can be performed by a healthcare provider, healthcare benefits provider, or patient automatically using a computer-implemented method (e.g., via a web service or stand-alone computer system).

II. Methods and Compositions for Coagulation Activity Testing

Figure 2:
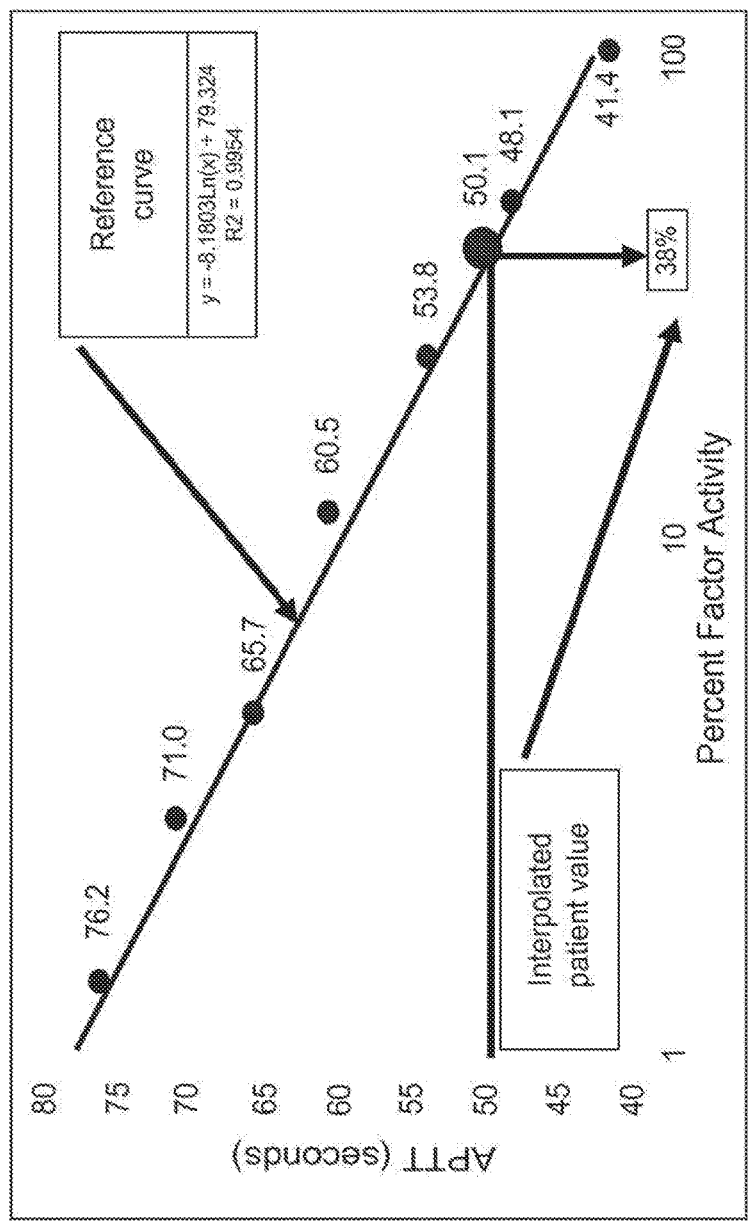
FIG. 2 shows an overview of one stage assay (aPTT).

The standard methodology for determining coagulation factor levels in use today is the one stage coagulation factor clotting assay (FIG. 2). A major drawback of this assay is that one cannot use whole blood samples. A typical one stage coagulation factor clotting assay requires, for example (i) venous blood drawn into sodium citrate anticoagulant, (ii) centrifugation to obtain a plasma sample, (iii) laboratory bench top coagulation analyzers and specifically trained laboratory personnel, (iv) liquid reagent preparation and standard curve construction, (v) multiple step assay procedures, (vi) dilution of patient plasma, (vii) mix with factor deficient plasma to mask inter-individual phenotypic variation, (viii) pre-incubation with non-physiological contact phase activators to generate an activated factor, e.g., Factor XIa, (ix) addition of $Ca^{+2}$ to initiate clotting, (x) optical (most common) or mechanical clot detection, (xi) derivation of factor level from Log-Linear (most common) plot of coagulation factor concentration versus clot time (reliable range for standard instrument systems using log-linear fits is ~3%-120% of normal; high end instruments have incorporated sophisticated software packages that can return accurate values below 1%).

To address the drawbacks of conventional one stage coagulation factor clotting assays, the present disclosure provides a modified coagulation assay which, in contrast with a standard coagulation assay, can operate using a whole blood sample, for example, fingerstick blood. Instead of pre-incubating the sample with a non-physiological contact phase activators, e.g., kaolin, typically used in laboratory-based assays, the assays disclosed herein use an activation mixture comprising an activated coagulation factor-phospholipid complex. This activation mixture is dried onto a solid substrate, e.g., a test strip.

Accordingly, the disclosed assays can be performed in point of care analyzers that do not require specially trained laboratory personnel. This general assay format, in which a patient sample (plasma or whole blood) can be applied directly to the solid substrate containing dried assay chemistry, is referred to as the Standard Factor Monitoring System ("Standard FMS") assay throughout the present disclosure.

In specific aspects of the present disclosure, the Standard FMS assays can be applied to determining coagulation activity of Factor VIII, e.g., measured as clotting time. For the Standard FMS Factor VIII assay, the activated coagulation factor-phospholipid complex can comprise, for example, a mixture of purified activated Factor IX (Factor IXa; abbreviated as FIXa) and phospholipid vesicles, wherein the activation mixture is dried onto a solid substrate.

In other specific aspects of the present disclosure, the Standard FMS assay can be applied to determining coagulation activity of Factor IX, e.g., measured as clotting time. For the Standard FMS Factor IX assay, the activated coagulation factor-phospholipid complex can comprise, for example, a mixture of purified activated Factor XI (Factor XIa; abbreviated as FXIa) and phospholipid vesicles, wherein the activation mixture is dried onto a solid substrate. In some aspects, the assays disclosed herein require no preincubation of the samples with the activators mixture.

In order to address the observed phenotypic variability between samples from the same donor or between donors, the Standard FMS assay can be modified. In some aspects of the present disclosure, less sensitive phospholipid blends in the activator mixture can be used to reduce phenotypic variability. In other aspects, adding a variety of purified coagulation factors to the sample, e.g., Factor II, Factor VII, Factor VIII, Factor IX, Factor X, Factor XI, Factor XII, Factor XIII, fibrinogen, vWF, or Tissue Factor can also reduce phenotypic variability. In other aspects, adding inhibitors to the sample, e.g., CTI, aprotinin, ε-aminocaproic acid (EACA), D-Phenylalanyl-l-prolyl-l-arginine chloromethyl ketone-Factor VIIa (FPRCK-FVIIa), or anti-FVIII monoclonal antibodies can also reduce phenotypic variability. Accordingly, the present disclosure provides also a variant of the Standard FMS assay, referred to as the "Alternate FMS" assay throughout the instant disclosure. This Alternate FMS assay is essentially a hybrid between the Standard FMS assay and a one stage factor assay (e.g., an aPTT assay) which is less susceptible to phenotypic variability. The Alternate FMS assay also utilizes an activation mixture comprising a coagulation factor (e.g., FIXa or FXIa) and a phospholipid vesicle preparation dried on the solid substrate (e.g., a disposable test strip). In the plasma based Alternate FMS assay, one part of sample (e.g., hemophilia plasma or fingerstick whole blood) can be mixed with a volume of a corresponding sample that has been depleted of the assay target factor (referred to as "substrate sample" throughout the instant disclosure). In this manner, the variability of non-target sample components can be normalized by addition of the substrate sample. This combination of sample (e.g., hemophilia plasma or fingerstick whole blood) and substrate sample can be done in an all-liquid system, resulting in a dilution of the sample, thus increasing the lower level of detection of the assay. In some aspects, the sample is diluted with substrate sample at about a 1:2 ratio, at about 1:3 ratio, at about a 1:4 ratio, or at about a 1:5 ratio. Dilution ratios can be adjusted above or below the disclosed ratios using routine experimentation.

As disclosed above, both the Standard FMS assay and the Alternate FMS assays use an activation mixture comprising an activated coagulation factor and a phospholipid mixture, wherein the composition is dried onto a solid substrate. The activation mixture can contain all the substances necessary for the determination of coagulation factor activity, e.g., via measurement of clotting time. These necessary substances are usually an activated coagulation factor functioning as coagulation activator component, phospholipids, and optionally divalent cations.

The activation mixtures disclosed herein generally do not contain stabilizers, however, in some aspects of the present disclosure, the activation mixture can contain one or more stabilizers known in the art, such as amino acids (e.g., D-alanine, L-alanine, beta-alanine, etc.). Suitable concentrations of stabilizers are known in the art or can be routinely determined. In some specific aspects, the activation mixture disclosed herein consists of or substantially consists of an activated coagulation factor and a phospholipid mixture, i.e., the activation mixture it does not contain, e.g., divalent cations, stabilizers such as albumin o amino acids, or additional coagulation factor activators or inhibitors.

In some aspects, the solid substrate can be, e.g., paper, plastic, glass, ceramic material, metal, and combinations thereof. The solid substrate can be, for example, the surface on a test strip, test stick, reaction chamber, cartridge, chip, well plate, or array used in an apparatus to measure coagulation factor activity or coagulation time. In some aspects, the solid substrate can be a membrane, which can be single layered or multilayered. In some aspects, the solid substrate is the surface of a disposable test strip. In other aspects, the solid substrate is the wall in a well in a plastic cartridge. In other aspects, the solid substrate is the wall of a well in a multiwell plate (e.g., a 96-well place). In some aspects, the solid substrate is the wall of a capillary. In other aspects, the solid substrate is the wall of a vial. In other aspects, the solid substrate is a surface in a mechanical mixing component of a measurement apparatus.

The solid substrate can be made of any suitable material which preferably has good thermal conductivity, clarity for optical transmission, mechanical properties for easy construction, surface properties that allow for uniform drying and stability of the activation mixture, and neutrality to the liquid medium in the sample to prevent interference with the coagulation assay. For this purpose, plastic are especially well suited. Suitable plastics include, for example, those with high free surface energies and low water sorption, including PETG, polyester (MYLAR®), polycarbonate (LEXAN®), polyvinyl chloride, polystyrene, SAN, acrylonitrile-butadiene-styrene (ABS) (e.g., CYCOLAC®), etc. In some aspects, plastics and other materials used as solid substrates can be hydrophobic, which would make it difficult to uniformly coat the surface with the activation mixtures disclosed here. Therefore, in some aspects, the substrate can be coated with another reagent (e.g., chemicals such as poly(3-hydroxybutyrate-co-3-hydroxy-hexanoate) (PHBHHx), poly(3-hydroxybutyrate-co-3-hydroxyvalerate) (PHBV), or polylactic acid (PLA); or proteins such as collagen or fibronectin) that would render the surface of the substrate hydrophilic and permit attachment of the activation mixture to the surface. In other aspects, the substrate can be physically modified by plasma etching or corona treating to render its surface hydrophilic.

The activation mixture can be provided, for example, (i) already dried onto a solid substrate, (ii) in a liquid to be dried in situ, or (iii) in a dry form (e.g., lyophilized form) to be reconstituted and dried onto the solid substrate. Dry components can be provided separately or in a premixed form. The activation mixture can be dried onto the solid substrate by using methods known in the art. For example, the drying of the activation mixture can be accomplished by air drying (e.g., at room temperature), drying under an inert gas stream (e.g., nitrogen or argon), vacuum drying, lyophilizing, dessicant drying, convective drying, etc. The term drying "onto" a solid substrate also encompasses drying the activation mixture "into" a porous substrate. In this respect, the dry activation mixture can be, for example, located into porous matrices such as sponges, porous paper filters, fleece or felt material, or can be microencapsulated.

The activation mixture can be applied to the substrate using methods known in the art, e.g., spray painting or lyophilization. In some aspects, the activation mixture can be chemically conjugated to the substrate. Chemical conjugation methods to covalently attach lipids, e.g., phospholipids and/or proteins, e.g., coagulation factors, are known in the art.

In some aspects, the activation mixture disclosed herein can be used to measure clotting time in samples containing or suspected to contain a coagulation factor, for example, Factor VIII or Factor IX. In some aspects, the coagulation factor is a Factor VIII protein or a fragment, variant, or derivative thereof as disclosed below. In other aspects, the coagulation factor is a Factor IX protein or a fragment, variant, or derivative thereof. In some specific aspects, the Factor VIII or Factor IX proteins are chimeric proteins (e.g., rFVIIIFc or rFIXFc) or hybrid proteins.

In some aspects, the Factor VIII chimeric protein is a single chain (SC) rFVIIIFc. SC rFVIIIFc are disclosed, for example, in U.S. Provisional Application No. 61/668,889, and U.S. Pat. No. 7,041,635, both of which are herein incorporated by reference in their entireties.

The activation mixture disclosed herein can contain an activated coagulation factor, or alternatively a hematologically equivalent, such, as a fragment, variant, or derivative thereof.

In some aspects, for example to apply the methods disclosed herein to measure the coagulation activity of a Factor VIII protein (or a fragment, variant, derivative, chimeric protein or hybrid protein thereof), the activated coagulation factor is a Factor IXa protein or a fragment, variant, or derivative thereof. In some specific aspects, a Factor IXa protein (or a fragment, variant, derivative, chimeric protein or hybrid protein thereof) is present in the activation mixture composition prior to drying within a range of about 0.01 U/mL to about 0.05 U/mL. In some aspects, the concentration of Factor IXa protein or a fragment, variant, or derivative thereof is about 0.01 U/mL, about 0.02 U/mL, about 0.03 U/mL, about 0.04 U/mL, about 0.05 U/mL, about 0.06 U/mL, about 0.07 U/mL, about 0.08 U/mL, about 0.09 U/mL, or about 0.1 U/mL. In some aspects, the concentration of Factor IXa protein or a fragment, variant, or derivative thereof is at least about 0.1 U/mL.

In other aspects, for example to apply the methods disclosed herein to measure the coagulation activity of a Factor IX protein or a fragment, variant, or derivative thereof, the activated coagulation factor is a Factor XIa protein or a fragment, variant, or derivative thereof. In some specific aspects, the Factor XIa protein or a fragment, variant, or derivative thereof is present in the activation mixture composition prior to drying within a range of about 0.01 U/mL to about 0.05 U/mL. In some aspects, the concentration of Factor XIa protein or a fragment, variant, or derivative thereof is about 0.01 U/mL, about 0.02 U/mL, about 0.03 U/mL, about 0.04 U/mL, about 0.05 U/mL, about 0.06 U/mL, about 0.07 U/mL, about 0.08 U/mL, about 0.09 U/mL, or about 0.1 U/mL. In some aspects, the concentration of Factor XIa protein or a fragment, variant, or derivative thereof is at least 0.1 U/mL. In some aspects, the concentration of Factor XIa protein or a fragment, variant, or derivative thereof is about 0.01 mg/mL, about 0.02 mg/mL, about 0.03 mg/mL, about 0.04 mg/mL, about 0.05 mg/mL, about 0.06, g/mL, about 0.07 mg/mL, about 0.08 mg/mL, about 0.09 mg/mL, or about 0.1 mg/mL. In some aspects, the concentration of Factor XIa protein or a fragment, variant, or derivative thereof is about 0.1 mg/mL. In some aspects, the concentration of Factor XIa protein or a fragment, variant, or derivative thereof is about 0.10 mg/mL, about 0.15 mg/mL, about 0.20 mg/mL, about 0.25 mg/mL, about 0.30 mg/mL, about 0.35, g/mL, about 0.40 mg/mL, about 0.45 mg/mL, or about 0.50 mg/mL.

One skilled in the art would understand that other activated coagulation factors and cofactors can be used instead of Factor IXa and FXIa depending on the coagulation factor tested in the coagulation assay.

The activation mixture contains a phospholipid mixture comprising at least one phospholipid. In some aspects, the phospholipid mixture comprises 2 phospholipids. In other aspects, the phospholipid mixture comprises 3 phospholipids. In other aspects, the phospholipid mixture comprises more than three phospholipids. In other aspects, the phospholipid mixture comprises at least one phospholipid in combination with at least another lipid, e.g., a fatty acid or cholesterol.

In some specific aspects, the composition of the phospholipid mixture is defined, i.e., phospholipid(s) and other lipid components (if present) are combined according to predetermined ratios. In other aspects, the composition of phospholipid mixture is not defined, e.g., the phospholipid mixture is obtained from an animal and/or vegetal tissue extract (e.g., egg, soy, etc). Chloroform extracts from rabbit brain are an example of suitable phospholipid mixture obtained from a tissue extract known in the art. In some aspects, the phospholipids can be natural. In other aspects, the phospholipids can be synthetic. In some aspects, the phospholipids are a mixture of natural and synthetic phospholipids. The phospholipids in the phospholipid mixture can be, for example, phosphatidylcholine, phosphatidylserine, phosphatidylglycerol, phosphatidic acid, phosphatidylethanolamine, and any combinations thereof.

Synthetic phospholipics that can be present in the phospholipid mixture include, for example, synthetic phosphatidic acid (e.g., DMPA, DPPA, DSPA), synthetic phosphatidylcholine (e.g., DDPC, DLPC, DMPC, DPPC, DSPC, DOPC, POPC, DEPC), synthetic phosphatidylglycerol (e.g., DMPG, DPPG, DSPG, POPG), synthetic phosphatidylethanoamine (e.g., DMPE, DPPE, DSPE, DOPE), synthetic phosphatidylserine (e.g., DOPS), and combinations thereof.

In some specific examples, the phospholipid mixture comprises 70 mole-% of phosphatidylcholine and 30 mole-% of phosphatidylserine. In other specific examples, the phospholipid mixture comprises 80 mole-% of phosphatidylcholine, 10 mole-% of phosphatidylserine, and 10 mole-% of phosphatidylglycerol. In yet other specific examples, the phospholipid mixture comprises 75 mole-% of phosphatidylcholine, 20 mole-% of phosphatidylserine, and 5 mole-% of phosphatidylglycerol.

In some specific examples, the phospholipid mixture consists or consists essentially of 70 mole-% of phosphatidylcholine and 30 mole-% of phosphatidylserine. In other specific examples, the phospholipid mixture consists or consists essentially of 80 mole-% of phosphatidylcholine, 10 mole-% of phosphatidylserine, and 10 mole-% of phosphatidylglycerol. In yet other specific examples, the phospholipid mixture consists or consists essentially of 75 mole-% of phosphatidylcholine, 20 mole-% of phosphatidylserine, and 5 mole-% of phosphatidylglycerol.

In some aspects, the phospholipid mixture comprises at least about 5 mole-%, at least about 10 mole-%, at least about 15 mole-%, at least about 20 mole-%, at least about 25 mole-%, at least about 30 mole-%, at least about 35 mole-%, at least about 40 mole-%, at least about 45 mole-%, at least about 50 mole-%, at least about 55 mole-%, at least about 60 mole-%, at least about 65 mole-%, at least about 70 mole-%, at least about 75 mole-%, at least about 80 mole-%, at least about 85 mole-%, at least about 90 mole-%, or at least about 95 mole-% of phosphatidylcholine.

In some aspects, the phospholipid mixture comprises at least about 5 mole-%, at least about 10 mole-%, at least about 15 mole-%, at least about 20 mole-%, at least about 25 mole-%, at least about 30 mole-%, at least about 35 mole-%, at least about 40 mole-%, at least about 45 mole-%, at least about 50 mole-%, at least about 55 mole-%, at least about 60 mole-%, at least about 65 mole-%, at least about 70 mole-%, at least about 75 mole-%, at least about 80 mole-%, at least about 85 mole-%, at least about 90 mole-%, or at least about 95 mole-% of phosphatidylserine.

In some aspects, the phospholipid mixture comprises at least about 5 mole-%, at least about 10 mole-%, at least about 15 mole-%, at least about 20 mole-%, at least about 25 mole-%, at least about 30 mole-%, at least about 35 mole-%, at least about 40 mole-%, at least about 45 mole-%, at least about 50 mole-%, at least about 55 mole-%, at least about 60 mole-%, at least about 65 mole-%, at least about 70 mole-%, at least about 75 mole-%, at least about 80 mole-%, at least about 85 mole-%, at least about 90 mole-%, or at least about 95 mole-% of phosphatidylglycerol.

In some aspects, the phospholipid mixture further comprises cholesterol. In some aspects, the phospholipid mixture comprises at least about 1 mole-%, at least about 2 mole-%, at least about 3 mole-%, at least about 4 mole-%, at least about 5 mole-%, at least about 6 mole-%, at least about 7 mole-%, at least about 8 mole-%, at least about 9 mole-%, at least about 10 mole-%, at least about 11 mole-%, at least about 12 mole-%, at least about 13 mole-%, at least about 14 mole-%, at least about 15 mole-%, at least about 16 mole-%, at least about 17 mole-%, at least about 18 mole-%, at least about 19 mole-%, or at least about 20 mole-% of cholesterol.

In some aspects, the phospholipid mixture is combined with the activated coagulation factor prior to drying onto a solid substrate. In some aspects, the phospholipid mixture is in vesicle form (e.g., a liposome or other artificial lipid vesicle). In some aspects, the vesicles are unilamellar vesicles, e.g., small unilamellar vesicles. Unilamellar vesicles can be produced using methods known in the arts, e.g., extrusion or sonication. Typically, small unilamellar vesicles are formed by sonication (e.g., tip or bath sonication) from large multilamellar vesicles. Large unilamelar vesicles can be formed, for example, by extrusion or by allowing small unilamellar vesicles to coalesce.

Divalent cations are optionally present in the activation mixture. In some aspects, divalent cations are present in the sample (e.g., a recalcified sample) and in the activation mixture. In other aspects, divalent cations can be added after the sample has contacted the activation mixture.

In some aspects, the divalent cations are calcium ions. Any chemical source of calcium cations can be used, e.g., $CaCl_2$, $Ca(NO_2)_2$, $CaSO_4$, or other inorganic or organic calcium cation-containing compounds.

The methods disclosed herein can be applied to any sample containing a coagulation factor or suspected of containing a coagulation factor. In some aspects, the sample can be whole blood, citrated or equivalently stabilized blood, plasma, or other fluid sample containing or suspected of containing a coagulation factor. In some aspects, the sample is decalcified, e.g., decalcified plasma. Plasma can be decalcified, for example, by adding chelators such as EDTA. In other aspects, the sample is recalcified, e.g., recalcified plasma. Methods to decalcify blood samples, e.g., plasma, and specific conditions and calcium concentrations for recalcification are well known in the art.

Measurements of coagulation, e.g., clotting time (Ct) measurements, using the activation mixtures disclosed herein, wherein the activation mixture is dried onto a solid substrate, can be carried out manually by visual observation of clot formation. However, measurement of coagulation, e.g., clotting time (Ct) measurement, can also be performed using optical or mechanical measurement instruments such as those marketed, e.g., by the Amelung, Baxter, Labor, Medtronic, CoaguSense, Roche Diagnostics (e.g., Coagu-Chek® I, II, XS; Coumatrak®), CardioVascular Diagnostics (e.g., TAS®), Organon Teknica (Coag-A-Mate®), Haemoscope (TEG), Pentapharm (ROTEM), Medirox, Siemens, Hemotek, Helena Laboratories, and Behring companies. Measurements can also be performed using point-of-care devised discussed infra.

The activation mixtures disclosed herein, wherein the activation mixture is dried onto a solid substrate, can be applied to a variety of methods for measuring coagulation, and/or the concentration of coagulation factors in biological samples, e.g., blood or plasma, and/or to determine the effect or concentration of direct or indirect inhibitors of coagulation. Such methods include both chromogenic assays and so-called "clotting methods" such as the aPTT assay. In general, these "clotting methods" are characterized by the fact that coagulation is activated and the time from coagulation activation until detection of clotting in the sample is measured, and in turn clotting time can be converted into direct concentration units by establishing a calibration curve with appropriate calibration reagents.

In specific aspects of the present disclosure, the activation mixture can be used as a reagent for the measurement of the Factor VIII activity of a Factor VIII protein (or a fragment, variant, derivative, chimeric protein, or hybrid protein thereof) in a sample. In one specific aspect, such activation mixture comprises 80% of 0.1 mg/mL Factor IXa and 20% of a phospholipid mixture comprises 75 mole-% of phosphatidylcholine, 20 mole-% of phosphatidylserine, and 5 mole-% of phosphatidylglycerol, wherein said activation mixture is dried onto a solid substrate. In another specific aspect, such activation mixture consist or substantially consists of 80% of 0.1 mg/mL Factor IXa and 20% of a phospholipid mixture comprises 75 mole-% of phosphatidylcholine, 20 mole-% of phosphatidylserine, and 5 mole-% of phosphatidylglycerol, wherein said activation mixture is dried onto a solid substrate.

In specific aspects of the present disclosure, the activation mixture can be used as a reagent for the measurement of the Factor IX activity of a Factor IX protein (or a fragment, variant, derivative, chimeric protein, or hybrid protein thereof) in a sample. In one specific aspect, such activation mixture comprises 80% of Factor XIa suspension and 20% of a phospholipid mixture comprising 75 mole-% of phosphatidylcholine, 20 mole-% of phosphatidylserine, and 5 mole-% of phosphatidylglycerol, wherein said activation mixture is dried onto a solid substrate. In another specific aspect, such activation mixture consists or substantially consists of 80% of Factor XIa suspension and 20% of a phospholipid mixture comprising 75 mole-% of phosphatidylcholine, 20 mole-% of phosphatidylserine, and 5 mole-% of phosphatidylglycerol, wherein said activation mixture is dried onto a solid substrate. The exact amount of FXIa suspension needed varies depending on the specific activity of this reagent and is titrated for optimal amount and may include approximately 0.1 mg/mL to approximately 0.5 mg/mL.

Also provided in the present disclosure is a kit for performing a measurement of coagulation factor activity or coagulation time in a sample, wherein said kit comprises the components to prepare any of the activation mixtures disclosed herein in one or more vials, as well as instructions to dry the components to prepare any of the activation mixtures disclosed herein onto a solid substrate. Such kit can comprise, for example, (i) a solution comprising both an activated coagulation factor and phospholipid vesicles in a single vial, or (ii) separate vials, one of them containing a solution of activated coagulation factor and a second vial containing a solution of phospholipid vesicles, or (ii) a vial containing a solution of activated coagulation factor and a second vial containing a dried phospholipid mixture to be reconstituted to produce phospholipid vesicles, etc. Thus, in some aspects, the kit comprises one or more components in a dry form or non-dry form in one or more vials, instructions for reconstituting or mixing the components in the kit, and instruction for drying the activation mixture onto a solid substrate.

Also provided in the present disclosure is a sample holder for performing a blood coagulation assay, comprising a surface coated with any one of the activation mixtures disclosed herein, wherein the activation mixture is dried onto a solid substrate. For example, the sample holder can be a test strip, a test stick, a reaction chamber, a cup, a cuvette, a cartridge, a chip, a well plate, an array, a membrane, a capillary, etc. A particular advantage of using a dried activation mixture coating a surface (as opposed to using a fluid reagent) in a sample holder is that it extends the shelf life of the sample holder. A second advantage is that using a dried activation mixture applied to coat the inner walls of a sample holder (e.g., a cartridge, a well or a cuvette) is that the operator does not need to mix, pour, or otherwise deal with liquid reactants.

In performing the assays disclosed herein (e.g., the Standard FMS assay or the Alternate FMS assay), a great variation in protein concentrations, incubation times, reagent concentrations, and temperatures can be employed. The selection of particular assay parameters will depend on the coagulation factor to be assayed as well as the source, type and size of the sample to be assayed, the anticipated levels of coagulation factor contained therein, and the threshold of sensitivity desired. Taking these circumstances into consideration, selection of assay parameters will be apparent to those skilled in the art.

The assays disclosed herein (e.g., the Standard FMS assay or the Alternate FMS assay) can be used in methods for determining clotting time in a patient having a bleeding disorder. Accordingly, the present disclosure provides a method for determining clotting time in a patient having bleeding disorder comprising (a) contacting a sample obtained from the patient with an activation mixture comprising an activated coagulation factor and a phospholipid mixture, wherein the activation mixture is dried onto a solid substrate; and, (b) measuring the time between the contacting of the activation mixture with the blood sample and the onset of clotting, thereby calculating the clotting time (Ct).

The present disclosure also provides a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient will benefit from administration of a treatment; and, (c) administering the treatment to the patient if Ct indicates that the patient will benefit from administration of the treatment. Also provided is a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient will benefit from administration of a treatment; and, (c) instructing a healthcare provider to administer the treatment to the patient if Ct indicates that the patient will benefit from administration of the treatment.

The disclosure also provides a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct correlates with a therapeutically efficacious treatment; and, (c) administering an optimized treatment to the patient, wherein the treatment is maintained or adjusted. Also provided is a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct correlates with a therapeutically efficacious treatment; and, (c) instructing a healthcare provider to optimize the treatment administered, wherein the treatment is maintained or adjusted.

The instant disclosure also provides a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient has a bleeding disorder; and, (c) providing a treatment for the bleeding disorder if the patient is in need thereof. Also provided is a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct), wherein Ct indicates whether the patient has a bleeding disorder; and, (c) instructing a healthcare provider to provide treatment for the bleeding disorder if the patient is in need thereof.

Also provided in the present disclosure is a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) comparing the measured Ct with the Ct obtained from a corresponding standard, wherein the standard is representative of a therapeutically efficacious treatment, and wherein a similarity between the patient's results and the standard is indicative of efficacy of the patient's current treatment; and, (d) maintaining or adjusting the patient's treatment based on the relative difference between the patient's results and the corresponding standard. Also provided is a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) comparing the measured Ct with the Ct obtained from a corresponding standard, wherein the standard is representative of a therapeutically efficacious treatment, and wherein a similarity between the patient's results and the standard is indicative of efficacy of the patient's current treatment; and, (d) instructing a healthcare provider to maintain or adjusting the patient's treatment based on the relative difference between the patient's results and the corresponding standard.

The present disclosure also provides a method for determining a coagulation factor level in a bleeding disorder patient, comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) correlating the Ct value with the level of coagulation factor in the sample. The correlation between Ct and coagulation factor level (% Factor) can be calculated, for example, according to the formula:

$$Ct = A \times \mathrm{Ln}(\% \text{ Factor}) + B$$

wherein, for each coagulation factor, A is a constant value corresponding to the slope of a Ct versus coagulation factor concentration dose-response, and B is patient-specific off-set value.

For a given coagulation factor, the A values for dose response curves plotting concentration of coagulation factor (% Factor) versus Ct are similar for all patients, whereas the B off-set values are different due to patient-specific global coagulation differences. The variability in B values can be addressed, for example, by optimizing the chemistry of the activation mixture so that there is no difference in B values among patients. The resulting correlation between concentration of factor and Ct can be used in a "Ready to Use Factor Monitoring Device" that does not require patient-specific calibration. Such device can be, for example, a point-of-care device.

Alternatively, the variability in B values can be addressed by customizing the device for each patient. For example, Ct can be measured during an initial (training) visit using the Standard FMS assay or Alternate FMS assay disclosed herein, and venous sample for standard laboratory analysis can be obtained at the same time. The B value, offset between Ct value from FMS assay(s) and the laboratory assays, could be provided to the patient (e.g., as an ID value). The ID value could be used to program the device, thus providing a "Customized Factor Monitoring Device"

specifically customized for a single patient. Multiple patient IDs would be possible per device. Such device can be, for example, a point-of-care device.

The instant disclosure also provides a method for determining a pharmacokinetic (PK) parameter in a bleeding disorder patient, comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) correlating a PK with the calculated Ct value, thereby determining the value of the PK parameter.

Also provided in the present disclosure is a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter indicates that the patient will benefit from administration of the treatment; and, (d) administering the treatment to the patient if the PK parameter indicates that the patient will benefit from administration of the treatment. Also provided in the present disclosure is a method of treating a patient having a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter indicates that the patient will benefit from administration of the treatment; and, (d) instructing a healthcare provider to administer the treatment to the patient if the PK parameter indicates that the patient will benefit from administration of the treatment.

The present disclosure also provides is a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter correlates with a therapeutically efficacious treatment; and, (d) administering an optimized treatment to the patient, wherein the treatment is maintained or adjusted. The present disclosure also provides a method of optimizing a bleeding disorder treatment in a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter correlates with a therapeutically efficacious treatment; and, (d) instructing a healthcare provider to administer an optimized treatment to the patient, wherein the therapy is maintained or adjusted.

The instant disclosure also provides a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct, wherein the PK parameter indicates whether the patient has a bleeding disorder; and, (d) providing treatment for the bleeding disorder if the patient is in need thereof.

Also provided in the instant disclosure is a method of diagnosing whether a patient is in need of treatment for a bleeding disorder comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) determining a PK parameter based on Ct, wherein the PK parameter indicates whether the patient has a bleeding disorder; and, (d) instructing a healthcare provider to provide therapy to treat the bleeding disorder if the patient is in need thereof.

The present disclosure also provides a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); and, (c) determining a PK parameter based on Ct; (d) comparing the PK parameter with the PK obtained from a corresponding standard, wherein the standard is representative of a therapeutically efficacious treatment, and wherein a similarity between the patient's results and the standard is indicative of efficacy of the patient's current treatment; and, (e) maintaining or adjusting the patient's treatment based on the relative difference between the patient's results and the corresponding standard. Also provided is a method of monitoring the efficacy of a bleeding disorder treatment administered to a patient comprising (a) contacting a sample obtained from the patient with an activation mixture comprising an activated coagulation factor and a phospholipid mixture, wherein the activation mixture is dried onto a solid substrate; (b) measuring the time between the contacting of the activation mixture with the sample and the onset of clotting, thereby calculating the clotting time (Ct); (c) determining a PK parameter based on Ct; (d) comparing the PK parameter with the PK obtained from a corresponding standard, wherein the standard is representative of a therapeutically efficacious treatment, and wherein a similarity between the patient's results and the standard is indicative of efficacy of the patient's current treatment; and, (e) instructing a healthcare provider to maintain or adjust the patient's treatment based on the relative difference between the patient's results and the corresponding standard.

In some aspects, the PK is terminal half-life ("HL"). In other aspects, the PK is time to through ("T"). The PK parameters disclosed herein as well as other PK parameters known in the art can be calculated from Ct and additional parameters that can be determined experimentally and/or from pharmacodynamic simulation and/or pharmacokinetic simulations. For example, pharmacokinetic and pharmacodynamics parameters can be calculated for a certain coagulation factor, for a certain population, or for a certain administration route, dosage, or other condition based on simulations conducts on data obtained from a single patient or from multiple patients (e.g., patients in a clinical trial).

In some aspects, HL can be calculated according to the formula:

$$HL = -0.693 \times (T_2 - T_1) \times A/(Ct_1 - Ct_2)$$

wherein, for each coagulation factor, A is a constant value corresponding to the slope of a Ct versus coagulation factor concentration dose-response, $T_1$ and $T_2$ are times at which Ct is measured, and $Ct_1$ and $Ct_2$ are Ct values measured at $T_1$ and $T_2$, respectively. In this calculation, the offset value B becomes irrelevant, i.e., interpatient differences in global coagulation do not affect terminal half-life. The possibility of repeating Ct measures on a point-of-care device on multiple days applying the method and compositions disclosed herein (for example, one measurement per day for 5 to 8 days) means that the likely result would be far more accurate than terminal half-life values obtained using one or two traditional laboratory-based measurements.

In some aspects, the patient-specific terminal half-life calculated according to the method disclosed above can be combined with pharmacokinetic and/or pharmacodynamics data. For example, product-specific in vivo recovery and distribution phase (α-phase) half-life data can be obtained via population modeling using data obtained from clinical trials. "In vivo recovery" ("IVR") is generally represented by the incremental recovery (K-value), which is the observed peak activity minus predose level and then divided by the dose. IVR can also be calculated on a percentage basis. The mean IVR can be determined in a patient population, or the individual IVR can be determined in a single subject. Product-specific in vivo recovery and distribution phase (α-phase) half-life data can be combined to patient-specific terminal half-life data to calculate time to trough (T) according to the formula:

$$T = -1.44 \times HL/(A \times (Ct_{measured} - Ct_{trough}))$$

wherein for each coagulation factor A is a constant value corresponding to the slope of a Ct versus coagulation factor concentration dose-response, and HL is the terminal half-life, $Ct_{measured}$ is Ct measured at certain time point, and $Ct_{trough}$ is patient-specific clot time at trough. In some aspects, the patient is administered a new dose of coagulation factor every T interval.

In some aspects, the sample used in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, comprises, e.g., whole blood, citrated or equivalently stabilized blood, plasma, or other fluid sample containing or suspected of containing a coagulation factor. In some aspects, the sample is whole blood, for example venous blood obtained via phlebotomy, whereas in other aspects the blood is fingerstick blood. In some specific aspects, a single drop of fingerstick blood is required to practice the disclosed methods.

In other aspects, the sample is plasma. Samples, e.g., plasma or blood, can be refrigerated or used at room temperature. In some aspects, samples, e.g., plasma or blood, can be frozen and thawed prior to contacting the sample with the activation mixture. In other cases, the sample has not been frozen and thawed prior to contacting the sample with the activation mixture. In some aspects, the sample is decalcified, e.g., by adding a chelator such as EDTA to the sample. In other aspects, the decalcified sample is recalcified prior to contacting the sample with the activation mixture by adding a solution containing divalent ions, e.g., calcium ions. In certain aspects, the decalcified sample is recalcified after contacting the sample with the activation mixture.

In certain aspects, variability between samples can be reduced by adding, for example, a purified coagulation factor or an inhibitor of coagulation to the sample. Purified coagulation factor that can be added to the sample include, for example, Factors II, Factor VII, Factor VIII, Factor IX, Factor X, Factor XI, Factor XII, Factor XIII, Fibrinogen, vWF, Tissue Factor, and combinations thereof. Coagulation inhibitors that can be added to the sample include, for example, CTI, aprotinin, ε-aminocaproic acid (EACA), D-Phenylalanyl-l-prolyl-l-arginine chloromethyl ketone-Factor VIIa (FPRCK-FVIIa), anti-coagulation factor monoclonal antibodies, and combinations thereof. In some aspects, the one purified coagulation factor can be added to the sample. In other cases, more than one purified coagulation factor can be added to the sample. In some cases, one coagulation inhibitor can be added to the sample. In other cases, more than one coagulation inhibitor can be added to the sample. In some cases, a combination comprising at least one purified coagulation factor and at least one coagulation inhibitor can be added to the sample.

In some cases, the sample can be diluted, for example, with substrate sample (i.e., sample that has been depleted of the assay target factor). This dilution can consist, for example, of one part of sample diluted with three parts of substrate sample. In some aspects, the sample is diluted with substrate sample at about a 1:2 ratio, at about 1:3 ratio, at about a 1:4 ratio, or at about a 1:5 ratio. Dilution ratios can be adjusted above or below the disclosed ratios using routine experimentation.

In some aspects, the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, use an activation mixture comprising an activated coagulation factor wherein the factor is a Factor IXa protein or a fragment, variant, or derivative thereof.

In some aspects, the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, use an activation mixture comprising an activated coagulation factor wherein the factor is a Factor XIa protein or a fragment, variant, or derivative thereof.

In some aspects, the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, use an activation mixture comprising a phospholipid mixture. This phospholipid mixture can comprise, for example, 1 phospholipid, 2 phospholipids, 3 phospholipids, or more than 3 phospholipids. These phospholipids can be, for example, phosphatidylcholine, phosphatidylserine, or phosphatidylglycerol. The phospholipids in the phospholipid mixture can be, for example, natural phospholipids, synthetic phospholipids, or combinations thereof.

In some specific aspects, the phospholipid mixture comprises 70 mole-% of phosphatidylcholine and 30 mole-% of phosphatidylserine. In certain specific aspects, the phospholipid mixture consists or essentially consists of 70 mole-% of phosphatidylcholine and 30 mole-% of phosphatidylserine. In other aspects, the phospholipid mixture comprises 80 mole-% of phosphatidylcholine, 10 mole-% of phosphatidylserine, and 10 mole-% of phosphatidylglycerol. In yet other aspects, the phospholipid mixture consists or essentially consists of 80 mole-% of phosphatidylcholine, 10 mole-% of phosphatidylserine, and 10 mole-% of phosphatidylglycerol. In some aspects, the phospholipid mixture comprises 75 mole-% of phosphatidylcholine, 20 mole-% of phosphatidylserine, and 5 mole-% of phosphatidylglycerol. In other aspects, the the phospholipid mixture consists or essentially consists of 75 mole-% of phosphatidylcholine, 20 mole-% of phosphatidylserine, and 5 mole-% of phosphatidylglycerol. In certain aspects, the phospholipid mixture further comprises cholesterol, for example at a concentration from about 1 to about 20 mole-% of cholesterol.

In some aspects, the activation mixture used in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, comprises a phospholipid mixture in lipid vesicle form. In some aspects, the lipid vesicles are small unilamellar vesicles.

In some aspects, the activation mixture used in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, further comprises divalent cations, e.g., calcium ions.

In some aspects, the activation mixture used in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, can react with a coagulation factor, e.g., Factor VII, Factor VIII, or Factor IX. In some aspects, the Factor VIII coagulation factor is a Factor VIII protein (or a fragment, variant, derivative, chimeric protein, or hybrid protein thereof). In some aspects, the Factor VIII coagulation factor is a chimeric Factor VIII-Fc fusion protein. In some aspects, the Fc portion of the chimeric Factor VIII protein comprises a human Fc domain. In some aspects, the chimeric Factor VIII protein comprises a B-domain deleted Factor VIII. In specific aspects, the chimeric Factor VIII protein comprises SEQ ID NO:6. or SEQ ID NO:2.

In other aspects, the Factor IX coagulation factor is a Factor IX protein (or a fragment, variant, derivative, chimeric protein, or hybrid protein thereof). In some aspects, the Factor IX coagulation factor is a chimeric Factor IX-Fc fusion protein. In some aspects, the Fc portion of the chimeric Factor IX protein comprises a human Fc domain. In certain specific aspects, the chimeric Factor IX protein comprises SEQ ID NO: 13.

In some aspects, the activation mixture used in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, is dried onto a the solid substrate. This solid substrate can be, for example, paper, plastic, glass, ceramic material, metal, and combinations thereof. In some aspects, the solid substrate is a surface on a test strip, test stick, reaction chamber, cartridge, chip, well plate, or array used in an apparatus to measure coagulation factor activity or coagulation time.

In some aspects, the patient in the methods of treating, optimizing a treatment, diagnosing whether a patient needs a treatment, monitoring the efficacy of the treatment, or in the methods for determining clotting times, coagulation factor levels, and pharmacokinetic (PK) parameters disclosed herein, has not yet been treated with a coagulation factor. However, in other cases, the patient has received prior coagulation factor treatment, but the treatment has been discontinued for a time period sufficient to deplete the coagulation factor treatment from the patient's blood.

The methods, compositions, and systems of the present disclosure can be applied to treating a patient or evaluating or determining whether a patient will benefit from administration of a therapeutically effective dose of a therapeutic agent that is capable of treating a bleeding disorder, for example, hemophilia A or hemophilia B. The methods of systems disclosed herein can be used to apply more precise coagulation factor dosing to patients. In a further aspect, the methods and systems disclosed herein can be used to increase the power and effectiveness of clinical trials. Thus, individuals in a study can be monitored and dosages adjusted individually. When the methods of the present disclosure are used for the treatment of bleeding disorders by administration of a coagulation factor, e.g., a Factor VIII or Factor IX protein (or fragment, variants, derivative, chimeric proteins, or hybrid protein thereof), individualized treatment using the methods provided herein can result in fewer disease flare-ups, and thus provide a higher quality of life for the patient. In order to treat a patient, samples from the patient can be obtained before or after the administration of a FVIII or FIX polypeptide. In some cases, successive samples can be obtained from the patient after clotting factor treatment has commenced or after treatment has ceased.

Samples can, e.g., be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of clotting times, the comparisons between time points, and treatment decisions can be performed by one or more healthcare providers, healthcare benefits providers, and/or clinical laboratories. In some cases, the methods, compositions, and systems disclosed herein can be applied in a point-of-care test system.

The methods described herein can be used for variety of evaluations, including without limitation, analysis of a patient's blood prior to treatment (or after complete washout of prior therapeutic treatment, to evaluate 'baseline' clot formation (which can correlate with severity of the disease) and adding various therapeutic composition(s) such as recombinant FVIII or FIX ex vivo to such blood in order to predict the individual's response to therapy. The methods disclosed herein can be applied, for example, to measure clotting time in samples from a patient suffering from a bleeding disorder, samples from a patient suffering from a clotting disorder, or samples from a healthy patient (e.g., prior to surgery). The methods disclosed herein can also be applied, for example, to determine the effect on coagulation of a natural, recombinant, or chimeric clotting factor, a biological (e.g., an antibody or fusion protein), an anticoagulant, or a small molecule drug added to a plasma or blood sample, or present or suspected to be present in a blood or plasma sample from a patient. Thus, the methods disclosed herein are generally applicable to the measurement of coagulation (e.g., by measuring clotting time) in samples from patients suffering or at risk of suffering conditions other bleeding disorders other than hemophilias. For example, in some conditions such as lupus, coagulation can be altered by the presence of lupus anticoagulant, a prothrombotic agent that precipitates the formation of thrombi in vivo. Patients with lupus and other conditions causing thrombosis can be treated with anticoagulants. Coagulation can also be altered by substances from animal origin, e.g., hirudin or proteins from snake venoms. Certain drug therapies, for example, warfarin treatment, are known to influence coagulation factor levels. Also patients suffering from consumptive coagulapathies such as thrombosis or disseminated intravascular coagulation (DIC) can present anomalies in coagulation factor levels which require careful clinical management. Successful treatment of these conditions similarly requires accurate determination of serum coagulation factor levels. In managing any of the aforementioned medical conditions, one mode of treatment involves administration of exogenous coagulation factors (e.g., Factor VIII or FIX proteins, fragments, variants or derivatives, for example rFVIIIFc or rFIXFc). It is essential that the precise concentration of such therapeutic doses be measured, and the quantity of coagulation factor be monitored.

Accordingly, the methods for diagnosing, treating, optimizing treatment, monitoring treatment, etc. disclosed herein can generally be applied to any diseases, conditions, or any situations in which blood coagulation is compromised or is suspected to be compromised, and also for prophylactic or preventive purposes (for example, to detect the onset of a disease or condition in a patient at risk or with a family history of such disease).

III. Point-of-Care Applications

In many situations, blood coagulation tests can be performed directly at the point of care without transport of the sample to an separate facility, e.g., a laboratory. The advantages of point-of-care analysis include (i) short turn-around time, as there is no time or only little time needed for transport of the sample, which allows fast monitoring-directed decisions, (ii) transport of the sample to an emergency laboratory can be very expensive, especially at night and when only few samples are to be analyzed, and (iii) self-testing of the patient is possible.

Available point-of-care methods methods for analysis of coagulation time have the same limitations as the determination of aPTT in the laboratory, e.g., non-linear dose response, low sensitivity, or high variation between samples and/or patients.

The methods and compositions of the present disclosure can be used in improved assays for point-of-care analysis of samples, e.g., blood samples such as whole blood samples. Thus, the present disclosure also includes a point-of-care hematological assay wherein the activation mixture disclosed herein is positioned in one or more reaction locations in a test apparatus and a sample of body fluid to be assayed (e.g., whole blood, citrated blood, or plasma) is contacted by the activation mixture.

As a specific aspect, the present disclosure provides a point-of-care device designed to rapidly test for coagulation levels, e.g., levels of coagulation factor VIII (FVIII) or factor IX (FIX) levels in hemophilia patients, from a finger stick blood sample by using raw clotting times, wherein said point of care device uses a disposable sample holder (e.g., a disposable strip) coated with a activation mixture comprising an activated coagulation factor and a phospholipid mixture, and wherein said activation mixture is dried onto said disposable sample holder.

The Standard FMS and Alternate FMS assays disclosed herein can be implemented in point-of-care devices and used as a global hemostasis tests by using raw clotting times (Ct) to determine individual pharmacokinetic parameters which in term can be used to decide treatment. Accordingly, the methods and composition disclosed herein can be applied to measure coagulation activity by implementing them in commercially available point-of-care self-monitoring devices, for example, i-STAT 1 (Abbott Point of Care); INRatio or INRatio2 PT INR Monitors (Alere); RapidPoint (Bayer); Coag-Sense PT/INR Monitoring System (CoaguSense); Actalyke Mini II, Actalyke XL, or Cascade POC (Helena Point of Care); Gem PCL Plus (Instrumentation Laboratory); Hemochrom Response, Hemochron Signature Elite, Hemochron Signature+, or ProTime Microcoagulation System (ITC); ACT Plus, or HMS Plus (Medtronic Cardiac Surgery); CoaguCheck XS Pro PT, CoaguCheck XS PT, CoaguCheck Plus PT (Roche Diagnostics); etc.

IV. Factor VIII and Factor IX Polypeptides

The methods and compositions provided in the present disclosure can be used in assays to determine the activity of clotting factors, such as Factor VIII and Factor IX polypeptides (including fragments, variants, derivatives, chimeric, and hybrid polypeptides). A detailed description of Factor VIII and Factor IX polypeptides (including fragments, variants, derivatives, chimeric and hybrid polypeptides) whose coagulating activity can be assessed by using the methods and compositions of the present disclosure is provided below.

A. Factor VIII Polypeptides

"Factor VIII," as used herein, means functional Factor VIII polypeptide in its normal role in coagulation, unless otherwise specified. Thus, the term Factor VIII includes variant polypeptides that are functional. Factor VIII proteins include the human, porcine, canine, and murine Factor VIII proteins. The full length polypeptide and polynucleotide sequences are known, as are many functional fragments, mutants and modified versions. Examples of human Factor VIII sequences are shown as subsequences in SEQ ID NOs: 2, 6, 8, 10, and 12 (Sequence Table 2). Factor VIII polypeptides include, e.g., full-length Factor VIII, full-length Factor VIII minus Met at the N-terminus, mature Factor VIII (minus the signal sequence), mature Factor VIII with an additional Met at the N-terminus, and/or Factor VIII with a full or partial deletion of the B domain. Factor VIII polypeptides include B domain deletions, whether partial or full deletions or single chain FVIII. Factor VIII can be made by recombinant means ("recombinant Factor VIII" or "rFVIII"), i.e., it is not naturally occurring or derived from plasma.

"B domain" of Factor VIII, as used herein, is the same as the B domain known in the art that is defined by internal amino acid sequence identity and sites of proteolytic cleavage by thrombin, e.g., residues Ser741-Arg1648 of full length human Factor VIII. The other human Factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the Factor VIII light chain activation peptide. The locations of the boundaries for all of the domains, including the B domains, for porcine, mouse and canine Factor VIII are also known in the art. In certain aspects, the B domain of Factor VIII is deleted ("B domain deleted Factor VIII" or "BDD FVIII"). An example of a BDD FVIII is REFACTO (recombinant BDD FVIII), which has the same sequence as the Factor VIII portion of the sequence in Sequence Table 2A(i) (amino acids −19 to 1438 or 1 to 1438 of SEQ ID NO:2).

A "B domain deleted Factor VIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some aspects, a B domain deleted Factor VIII sequence of the present disclosure comprises any one of the deletions disclosed at col. 4, line 4 to col. 5, line 28 and examples 1-5 of U.S. Pat. No. 6,316,226 (also in U.S. Pat. No. 6,346,513). In some aspects, a B domain deleted Factor VIII of the present disclosure has a deletion disclosed at col. 2, lines 26-51 and examples 5-8 of U.S. Pat. No. 5,789,203 (also U.S. Pat. Nos. 6,060,447, 5,595,886, and 6,228,620). In some aspects, a B domain deleted Factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some aspects, a B domain deleted Factor VIII has a deletion of most of the B domain, but still contains amino-terminal sequences of the B domain that are essential for in vivo proteolytic processing of the primary translation product into two polypeptide chain, as disclosed in WO 91/09122, which is incorporated herein by reference in its entirety. In some aspects, a B domain deleted factor VIII is constructed with a deletion of amino acids 747-1638, e.g., virtually a complete deletion of the B domain. Hoeben R. C., et al. *J. Biol. Chem.* 265 (13): 7318-7323 (1990), incorporated herein by reference in its entirety. A B domain deleted Factor VIII can also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions include, e.g.: deletion of amino acids 982 through 1562 or 760 through 1639 (Toole et al., Proc. Natl. Acad. Sci. U.S.A. (1986) 83, 5939-5942)), 797 through 1562 (Eaton, et al. Biochemistry (1986) 25:8343-8347)), 741 through 1646 (Kaufman (PCT published application No. WO 87/04187)), 747-1560 (Sarver, et al., DNA (1987) 6:553-564)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety.

In other aspects, BDD FVIII includes a FVIII polypeptide containing fragments of the B-domain that retain one or more N-linked glycosylation sites, e.g., residues 757, 784, 828, 900, 963, or optimally 943, which correspond to the amino acid sequence of the full-length FVIII sequence. Examples of the B-domain fragments include 226 amino acids or 163 amino acids of the B-domain as disclosed in Miao, H. Z., et al., Blood 103(a): 3412-3419 (2004), Kasuda, A, et al., J. Thromb. Haemost. 6: 1352-1359 (2008), and Pipe, S. W., et al., J. Thromb. Haemost. 9: 2235-2242 (2011) (e.g., the first 226 amino acids or 163 amino acids of the B domain are retained). In still other aspects, BDD FVIII further comprises a point mutation at residue 309 (from Phe to Ser) to improve expression of the BDD FVIII protein. See Miao, H. Z., et al., Blood 103(a): 3412-3419 (2004). In still other aspects, the BDD FVIII includes a FVIII polypeptide containing a portion of the B-domain, but not containing one or more furin cleavage sites (e.g., Arg1313 and Arg 1648). See Pipe, S. W., et al., J. Thromb. Haemost. 9: 2235-2242 (2011). The references are incorporated herein by reference, and each of the foregoing deletions can be made in any Factor VIII sequence.

In certain aspects, FVIII includes a single chain FVIII polypeptide. In one embodiment, a single chain FVIII polypeptide can include one or more mutations or substitutions at R1645 or R1648 corresponding to full-length Factor VIII sequence or both. Additional examples of single chain FVIII polypeptides can be found at U.S. Provisional Application No. 61/668,889, filed Jul. 6, 2012, which is incorporated herein by reference in its entirety. In another embodiment, a single chain FVIII polypeptide contains a FVIII polypeptide having a deletion of R1645 and/or R1648 corresponding to full-length FVIII sequence or a sequence containing R1645 and/or R1648 corresponding to full-length FVIII. For example, a single chain FVIII can contain a deletion of amino acid positions 746 to 1649, 746 to 1652, 746 to 1655, 758 to 1649, 758 to 1652, 758 to 1655, 765 to 1649, 765 to 1652, 765 to 1655, 748 to 1658, 755 to 1658, 762 to 1658, 769 to 1658, 776 to 1658, or 783 to 1658 corresponding to full-length FVIII sequence. Additional examples can be found at U.S. Pat. No. 7,041,635, filed Jan. 3, 2003, which is incorporated herein by reference in its entirety.

A great many functional Factor VIII variants are known, as is discussed above and below. In addition, hundreds of nonfunctional mutations in Factor VIII have been identified in hemophilia patients, and it has been determined that the effect of these mutations on Factor VIII function is due more to where they lie within the 3-dimensional structure of Factor VIII than on the nature of the substitution (Cutler et al., Hum. Mutat. 19:274-8 (2002), incorporated herein by reference in its entirety). In addition, comparisons between Factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human Factor VIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing Factor VIII in mammalian host cells and purification of human Factor VIII. Human Factor VIII expression in CHO (Chinese hamster ovary) cells and BHKC (baby hamster kidney cells) has been reported. Human Factor VIII has been modified to delete part or all of the B domain (U.S. Pat. Nos. 4,994,371 and 4,868,112, each of which is incorporated herein by reference in its entirety), and replacement of the human Factor VIII B domain with the human Factor V B domain has been performed (U.S. Pat. No. 5,004,803, incorporated herein by reference in its entirety). The cDNA sequence encoding human Factor VIII and predicted amino acid sequence are shown in SEQ ID NOs:1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of Factor VIII having reduced antigenicity and reduced immunoreactivity. U.S. Pat. No. 6,376,463, Lollar, J. S., incorporated herein by reference in its entirety, also reports mutants of Factor VIII having reduced immunoreactivity. US Application Publ. No. 2005/0100990, Saenko et al., incorporated herein by reference in its entirety, reports functional mutations in the A2 domain of Factor VIII.

A number of functional Factor VIII molecules, including B-domain deletions, are disclosed in the following patents U.S. Pat. Nos. 6,316,226 and 6,346,513, both assigned to Baxter; U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

The porcine Factor VIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of factor VIII sequences from a pig spleen cDNA library has been reported (Healey, J. F., et al., Blood 88:4209-4214 (1996), incorporated herein by reference in its entirety). Hybrid human/porcine Factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric Factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

The Factor VIII (or Factor VIII portion of a chimeric polypeptide) can be at least 90% or 95% identical to a Factor VIII amino acid sequence shown in Sequence Table 2 without a signal sequence (amino acids 1 to 1438 of SEQ ID NO:2; amino acids 1 to 2332 of SEQ ID NO:6; amino acids 1 to 740 of SEQ ID NO:8; amino acids 1 to 745 of SEQ ID NO:10; or amino acids 1 to 684 of SEQ ID NO:12). The Factor VIII (or Factor VIII portion of a chimeric polypeptide) can be identical to a Factor VIII amino acid sequence shown in Sequence Table 2 without a signal sequence (amino acids 1 to 1438 of SEQ ID NO:2; amino acids 1 to 2332 of SEQ ID NO:6; amino acids 1 to 740 of SEQ ID NO:8; amino acids 1 to 745 of SEQ ID NO:10; or amino acids 1 to 684 of SEQ ID NO:12).

The Factor VIII (or Factor VIII portion of a chimeric polypeptide) can be at least 90% or 95% identical to a Factor VIII amino acid sequence shown in Sequence Table 2 with a signal sequence (amino acids −19 to 1438 of SEQ ID NO:2; amino acids −19 to 2332 of SEQ ID NO:6; amino acids −19 to 740 of SEQ ID NO:8; amino acids −19 to 745 of SEQ ID NO:10; or amino acids −20 to 684 of SEQ ID NO:12). The Factor VIII (or Factor VIII portion of a chimeric polypeptide) can be identical to a Factor VIII amino acid sequence shown in Sequence Table 2 with a signal sequence (amino acids −19 to 1438 of SEQ ID NO:2; amino acids −19 to 2332 of SEQ ID NO:6; amino acids −19 to 740 of SEQ ID NO:8; amino acids −19 to 745 of SEQ ID NO:10; or amino acids −20 to 684 of SEQ ID NO:12).

B. Factor IX Polypeptides

"Factor IX", "FIX", "protein having FIX activity", "FIX protein", or "FIX polypeptide" as used herein, means functional Factor IX polypeptide in its normal role in coagulation, unless otherwise specified. Thus, the term Factor IX includes variant polypeptides that are functional and the polynucleotides that encode such functional variant polypeptides. Factor IX polypeptides include the human, bovine, porcine, canine, feline, and murine Factor IX polypeptides. The full length polypeptide and polynucleotide sequences of Factor IX are known, as are many functional variants, e.g., fragments, mutants and modified versions. Factor IX polypeptides include full-length Factor IX, full-length Factor IX minus Met at the N-terminus, full-length Factor IX minus the signal sequence, mature Factor IX (minus the signal sequence and propeptide), and mature Factor IX with an additional Met at the N-terminus. Factor IX can be made by recombinant means ("recombinant Factor IX" or "rFIX"), i.e., it is not naturally occurring or derived from plasma.

great many functional Factor IX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses Factor IX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant Factor IX molecules that exhibit increased protein stability, increased in vivo and in vitro half-life, and increased resistance to proteases at page 4, line 1 to page 19, line 11. WO 2007/149406 A2 also discloses chimeric and other variant Factor IX molecules at page 19, line 12 to page 20, line 9.

International publication number WO 08/118507 A2, which is herein incorporated by reference in its entirety, discloses Factor IX mutants that exhibit increased dotting activity at page 5, line 14 to page 6, line 5. International publication number WO 09/051717 A2, which is herein incorporated by reference in its entirety, discloses Factor IX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant Factor IX molecules that have an increased number of glycosylation sites, which result in an increased half-life, at page 4, line 26 to page 12, line 6. International publication number WO 09/140015 A2, which is herein incorporated by reference in its entirety, discloses functional Factor IX mutants that an increased number of Cys residues, which can be used for polymer (e.g., PEG) conjugation, at page 11, paragraph [0043] to page 13, paragraph [0053].

In addition, hundreds of non-functional mutations in Factor IX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional Factor IX polypeptide.

The Factor IX (or Factor IX portion of a chimeric polypeptide) can be at least 90% or at least 95% or 100% identical to a Factor IX amino acid sequence shown in Sequence Table 2 without a signal sequence and propeptide sequence (amino acids 1 to 415 of SEQ ID NO:14), or alternatively, with a propeptide sequence, or with a propeptide and signal sequence (full length Factor IX).

Factor IX coagulant activity is expressed as International Unit(s) (IU). One IU of Factor IX activity corresponds approximately to the quantity of Factor IX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

"Protein having FIX activity which is in its activated form," or "activated FIX protein" means the activated form of a corresponding FIX protein/polypeptide. The term "activated" in connection with an activated FIX protein/polypeptide is used according to its common meaning. For example, in vivo, Factor IX is produced as a zymogen, an inactive precursor. It is processed to remove a signal peptide, glycosylated and then cleaved, e.g., by factor XIa or factor VIIa to produce activated FIX (FIXa), a two-chain form where the two chains are linked by a disulfide bridge. For example, activated FIX protein can be formed during the production and/or purification of a recombinant FIX protein. In one example, in a pharmaceutical FIX polypeptide compositions, the activated form of the FIX polypeptide can be considered an impurity.

C. Factor VIII and Factor IX Chimeric Polypeptides

"Chimeric polypeptide," as used herein, means a polypeptide that includes within it at least two moieties (or portions thereof such as subsequences or peptides) from different sources. Chimeric polypeptides can include two, three, four, five, six, seven, or more polypeptides or portions thereof from different sources, such as different genes, different cDNAs, or different animal or other species. Chimeric polypeptides can include one or more linkers joining the different polypeptides or portions thereof. Thus, the polypeptides or portions thereof can be joined directly or they can be joined indirectly, via linkers, or both, within a single chimeric polypeptide. Chimeric polypeptides can include additional peptides such as signal sequences and sequences such as 6His and FLAG that aid in protein purification or detection. In addition, chimeric polypeptides can have amino acid or peptide additions to the N- and/or C-termini.

In certain aspects, a chimeric polypeptide is a long-acting clotting factor. "Long-acting clotting factor" such as long-acting FVIII or long-acting FIX is a Factor VIII or Factor IX having an increased half-life (also referred to herein as t½, t½ beta, elimination half-life and HL) over a reference Factor VIII or a reference Factor IX, respectively. The increased half-life of a long-acting Factor VIII or a long-acting Factor IX may be due to fusion to one or more non-Factor VIII or non-Factor IX polypeptides such as, e.g., Fc, XTEN, albumin, a PAS sequence, transferrin, CTP (28 amino acid C-terminal peptide (CTP) of hCG with its 4 O-glycans), polyethylene glycol (PEG), hydroxyethyl starch (HES), albumin binding polypeptide, albumin-binding small molecules, or two or more combinations thereof. The increased half-life may be due to one or more modification, such as, e.g., pegylation. Exemplary long-acting clotting factor polypeptides include, e.g., chimeric Factor VIII polypeptides comprising Fc, chimeric Factor VIII polypeptides comprising XTEN, chimeric Factor VIII polypeptides comprising albumin, chimeric Factor IX polypeptides comprising Fc, chimeric FIX polypeptide comprising XTEN, or chimeric Factor IX polypeptide comprising albumin. Additional exemplary long-acting Factor VIII polypeptides include, e.g., pegylated Factor VIII or pegylated Factor IX.

The "reference" polypeptide, in the case of a long-acting chimeric Factor VIII polypeptide, is a polypeptide consisting essentially of the Factor VIII portion of the chimeric polypeptide, e.g., the same Factor VIII portion without the Fc portion, without the XTEN portion, or without the albumin portion. The "reference" polypeptide, in the case of a long-acting chimeric Factor IX polypeptide, is a polypeptide consisting essentially of the Factor IX portion of the chimeric polypeptide, e.g., the same Factor IX portion without the Fc portion, without the XTEN portion, or without the albumin portion. Likewise, the reference polypeptide in the case of a modified Factor VIII or Factor IX is the same Factor VIII or Factor IX without the modification, respectively, e.g., a Factor VIII without the pegylation or a Factor IX without the pegylation.

In some aspects, the chimeric polypeptide comprises a Factor VIII portion and a non-Factor VIII portion. In some aspects, the chimeric polypeptide comprises a Factor IX portion and a non-Factor IX portion. Exemplary non-Factor VIII or non-Factor IX portions include, e.g., Fc, and albumin. Exemplary chimeric polypeptides include, e.g., chimeric Factor VIII-Fc polypeptides, chimeric Factor IX-Fc polypeptides, chimeric Factor VIII-albumin polypeptides, and chimeric Factor IX-albumin polypeptides.

Figure 1:
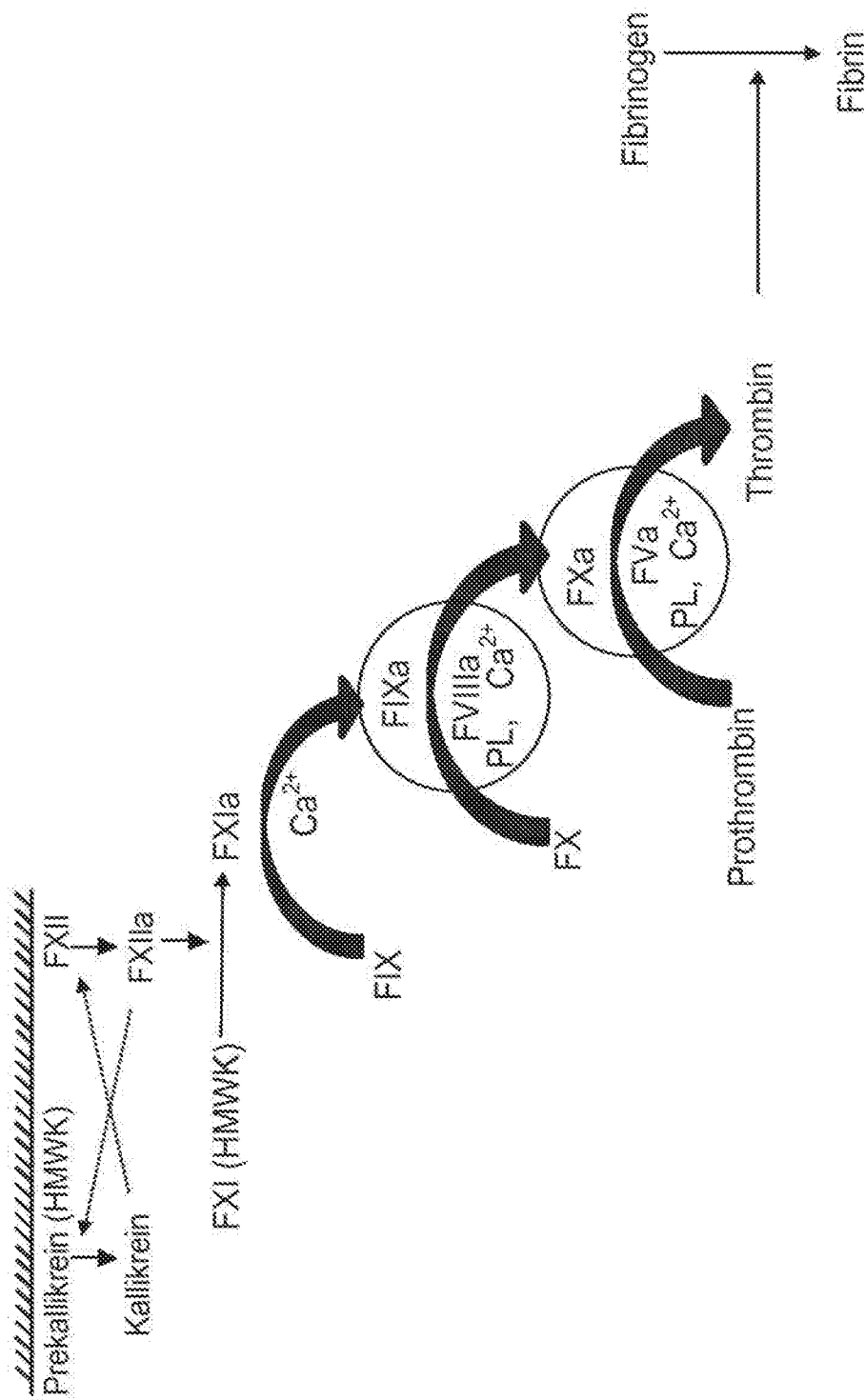
FIG. 1 shows a schematic representation of the coagulation cascade.

In some aspects, a chimeric polypeptide comprising a Factor VIII or Factor IX portion of a chimeric protein has an increased half-life (t½) over a polypeptide consisting of the same Factor VIII or Factor IX portion without the non Factor VIII or Factor IX portion. A chimeric Factor VIII or Factor IX polypeptide with an increased t½ can be referred to herein as a long-acting Factor VIII or Factor IX. Long-acting chimeric Factor VIII or Factor IX polypeptides include, e.g., Factor VIII or Factor IX fused to Fc (including, e.g., chimeric Factor VIII or Factor IX polypeptides in the form of a hybrid such as a FVIIIFc monomer dimer hybrid; see e.g, FIGS. 1 and 2, and Table 2; and U.S. Pat. Nos. 7,404,956 and 7,348,004).

Exemplary chimeric Factor VIII polypeptides include, e.g., chimeric Factor VIII-Fc polypeptides. Exemplary chimeric Factor VIII-Fc polypeptides include, e.g., SEQ ID NOs:2, 6, 8, 10, and 12 (Sequence Table 2), with or without their signal sequences and the chimeric Fc polypeptide of SEQ ID NO:4 (Sequence Table 2). The chimeric polypeptide can comprise a sequence at least 90% or 95% identical to the Factor VIII and Fc amino acid sequence shown in Sequence Table 2A(i) without a signal sequence (amino acids 1 to 1665 of SEQ ID NO:2) or at least 90% or 95% identical to the Factor VIII and Fc amino acid sequence shown in Sequence Table 2A(i) with a signal sequence (amino acids −19 to 1665 of SEQ ID NO:2). The chimeric polypeptide can comprise a sequence identical to the Factor VIII and Fc amino acid sequence shown in Sequence Table 2A(i) without a signal sequence (amino acids 1 to 1665 of SEQ ID NO:2) or identical to the Factor VIII and Fc amino acid sequence shown in Sequence Table 2A(i) with a signal sequence (amino acids −19 to 1665 of SEQ ID NO:2).

Exemplary chimeric Factor IX polypeptides are Factor IX-FcRn BP chimeric polypeptides, e.g., Factor IX-Fc chimeric polypeptides such as the FIXFc in SEQ ID NO:2 (Sequence Table 2), with or without its signal sequence and propeptide. Other exemplary chimeric polypeptides include, but are not limited to, Factor IX-XTEN chimeric polypeptides. Factor IX can be fused to either N-terminus or C-terminus of XTEN. The chimeric polypeptide can comprise a sequence at least 90% or at least 95% or 100% identical to the Factor IX and FcRn BP, e.g., the Fc amino acid sequence shown in Sequence Table 2A without a signal sequence and propeptide sequence (amino acids 1 to 642 of SEQ ID NO:14), or alternatively, with a propeptide sequence, or alternatively with a signal sequence and a propeptide sequence.

D. Factor VIII and Factor IX Hybrid Polypeptides

"Hybrid" polypeptides and proteins, as used herein, means a combination of a chimeric polypeptide with a second polypeptide. The chimeric polypeptide and the second polypeptide in a hybrid can be associated with each other via non-covalent protein-protein interactions, such as charge-charge or hydrophobic interactions. The chimeric polypeptide and the second polypeptide in a hybrid can be associated with each other via covalent bond(s) such as disulfide bonds. The chimeric peptide and the second peptide can be associated with each other via more than one type of bond, such as non-covalent and disulfide bonds. Hybrids are described in WO 2004/101740, WO2005/001025, U.S. Pat. Nos. 7,404,956, 7,348,004, and WO 2006/074199, each of which is incorporated herein by reference in its entirety. The second polypeptide can be a second copy of the same chimeric polypeptide or it can be a non-identical chimeric polypeptide.

In some aspects, the second polypeptide is a polypeptide comprising an Fc. In some aspects, the chimeric polypeptide is a chimeric Factor VIII-Fc polypeptide and the second polypeptide consists essentially of Fc, e.g, a rFVIIIFc recombinant fusion protein consisting of a single molecule of recombinant B-domain deleted human FVIII (BDD-rFVIII) fused to the dimeric Fc domain of the human IgG1, with no intervening linker sequence. This hybrid polypeptide is referred to herein as FVIIIFc monomeric Fc fusion protein, FVIIIFc monomer hybrid, monomeric FVIIIFc hybrid, and FVIIIFc monomer-dimer. In some aspects, the chimeric polypeptide is a Factor IX-FcRn BP, e.g., Factor IX-Fc chimeric polypeptide, and the second polypeptide consists essentially of Fc. See, e.g., Sequence Table 2 (SEQ ID NOs:14 and 4). See, e.g., U.S. Pat. No. 7,404,956, which is incorporated herein by reference in its entirety.

The second polypeptide in a hybrid can comprise or consist essentially of a sequence at least 90% or at least 95%, or 100% identical to the amino acid sequence shown in Sequence Table 2 without a signal sequence (amino acids 1 to 227 of SEQ ID NO:4), or alternatively, at least 90%, or at least 95%, or 100% identical to the amino acid sequence shown in Table 2 with a signal sequence (amino acids −20 to 227 of SEQ ID NO:4).

Having now described the present invention in detail, the same will be more clearly understood by reference to the following examples, which are included herewith for purposes of illustration only and are not intended to be limiting of the invention. All patents and publications referred to herein are expressly incorporated by reference in their entireties.

EXAMPLES

Materials and Methods

Preparation of Test Strips (FVIII)

Disposable strips were the same type as currently used in Coag-Sense™ PT/INR Monitoring System (CoaguSense, Inc, Fremont, Calif.) without the Prothrombin Time reagents added to the strip. Strips were coated with 1.25 μL of 80% of 0.1 mg/mL purified Factor IXa (obtained from Haematologic Technologies, Essex Junction, Vt.) plus 20% phospholipid vesicles prepared as described below. Strips were air dried in a dry 37° C. incubator and individually sealed in plastic pouches containing a desiccant.

Preparation of Phospholipids

The strip for the Standard FMS Factor VIII assay used an equal mix of Phospholipid Blend 2 and Phospholipid Blend 8. Phospholipid Blend 2 consisted of a phosphatidylcholine (PC) and phosphatidylserine (PS) mixture at a 70:30 molar ratio (mol-%). Phospholipid Blend 8 consisted of a PC, PS and phosphatidylglycerol (PG) mixture at a 80:10:10 molar ratio. Thus, the optimized ratio of PL on the Standard FMS Factor VIII assay strip ("standard strip") was 75:20:5 (PC:PS:PG).

To prepare phospholipid blends, a total of 2.6 μmoles of phospholipids dissolved in chloroform was dispensed into a glass tube, where individual phospholipids were mixed at the defined molar ratio (synthetic phospholipids can be obtained from Avanti Polar Lipids, Alabaster, Ala.). The phospholipid mixture was dried in a fume hood under a gentle stream of nitrogen or argon. When dry, phospholipid mixtures were dried in a speed-vac for an additional 1 hour to overnight under high vacuum to remove any residual chloroform. 2.6 mL Hepes Buffered Saline (10 mM HEPES pH 7.4 and 140 mM NaCl) at room temperature were added to the dried-down phospholipid mixture until all the dried lipid suspension was re-hydrated. The tube was incubated at 37° C. and vortexed intermittently. The result was a milky, uniform suspension. Small unilamellar vesicles were prepared by sonication for 7-10 minutes on ice with one-minute gap intervals between the shocks. The residual large vesicles were removed by filtering using 45-micron filters.

Test Procedure

The test strip containing the dried activator mixture (FIXa/PL mixture) was pre-warmed automatically after insertion into the measuring device. When the device was ready to receive a sample, patient plasma or whole blood was recalcified with 0.3 volumes of 60 mM $CaCl_2$ and 12 μL of the recalcified sample were immediately added to the well of the pre-warmed test strip. Clot formation was initiated as the blood/plasma dissolved the dried activator on the test strip. The device measured the time from initiation to formation of a clot with defined characteristics. This time interval was referred to as clotting time (Ct). See, e.g., FIG. 3 for an example of the application of the Standard FMS Factor VIII assay.

Further optimization of the FMS FVIII assay included the addition of trace amounts of Factor VIII (approx. 1% of normal) to the dried activator mixture, which resulted in a base clot time, rather than "timing out" in the absence any clot formation in severely hemophilic patient samples. Further optimization of the FMS FVIII assays will include adding $CaCl_2$ on the dried test strip rather than off-strip recalcification of the sample.

Optimized FMS FVIII assay chemistry during the clot reaction can contain the following reactants (i) 9.2 µL patient blood; (ii) 2.8 µL buffer; (iii) 14 mM $CaCl_2$; (iv) 21 µM phospholipid mix (PC:PS:PG at 75:20:5); (v) 8.3 µg Factor IXa; and (vi) 24 pg Factor VIII.

FMS Factor IX Assay

The FMS Factor IX assay (see, e.g., FIG. 4 for an example of the application of the Standard FMS Factor IX assay) followed the same procedure as for Factor VIII, except that (i) the activator mixture included on the test strip contains Factor XIa instead of Factor IXa (the exact amount of Factor XIa needed varied depending on the specific activity of this reagent and is titrated for optimal amount); and, (ii) trace amounts of Factor IX could optionally be added to the strip to achieve a base clotting time to improve responsiveness to small amounts of Factor IX in the patient sample.

Example 1

Standard Factor Monitoring System (FMS) Assay

Both Standard FMS assays (Standard FMS Factor VIII assay and Standard FMS Factor IX assay) were initiated by the application of 12 µL of recalcified patient plasma directly to the test bed, a disposable test strip containing activated coagulation factor-phospholipid complex. On this test bed, utilizing linear log-log curve fitting of concentration versus clotting time, both Standard FMS assays performed well when an individual Hemophilia A or Hemophilia B donor plasma was spiked with either rFVIIIFc or rFIXFc, respectively (TABLE 1).

TABLE 1

Application of Standard FMS Factor VIII and Factor IX assays to Hemophilia A and Hemophilia B Samples spiked with either rFVIIIFc or rFIXFc, respectively.

| | Standard FMS Factor VIII Assay | Standard FMS Factor IX Assay |
|---|---|---|
| Assay Range (IU/dL) | 0.8-100 | 0.2-100 |
| Accuracy (% Spike Recovery) | +/−10% | +/−10.1 |
| Precision (% CV) | 3.8 | 1.9 |

Example 2

Sensitivity of the Standard FMS Assay to Individual Phenotypic Variability

The disclosed "Standard FMS" assay system utilized undiluted patient plasma, thus, it was more analogous to an aPTT assay than to the one-stage factor assay. In the laboratory aPTT assay, one part undiluted patient plasma is generally combined with equal parts of liquid aPTT reagent and of $CaCl_2$ solution. In contrast, in the one-stage assay, one part diluted (1:5) patient plasma is generally combined with one part factor deficient plasma, one part aPTT reagent, and one part $CaCl_2$. Because of this dilution of patient plasma with factor deficient plasma, the one stage factor assay largely masks inter-subject variability that can occur as a result of variable levels of non-target coagulation factors (TABLE 2).

TABLE 2

Hemophilia Donor Phenotypic Variability

| Sample | PT (sec) | APTT (sec) | Fib. (mg/dL) | % II | % V | % VII | % VIII | % IX | % X | % XI | % XII |
|---|---|---|---|---|---|---|---|---|---|---|---|
| VIII Deficient Plasma Samples | | | | | | | | | | | |
| HRF11P2F8 | 11.1 | 104.8 | 293 | 85 | 86 | 80 | <1 | 86 | 107 | 79 | 85 |
| HRF11P3F8 | 11.2 | >400 | 353 | 82 | 76 | 95 | <1 | 98 | 95 | 82 | 87 |
| GK 892-2086 | 11.6 | 103.0 | 248 | 78 | 67 | 81 | <1 | 76 | 93 | 80 | 126 |
| HRF10-389 | 11.2 | 117.2 | 276 | 78 | 94 | 72 | <1 | 74 | 93 | 62 | 80 |
| HRF10-1081 | 10.8 | >400 | 334 | 89 | 116 | 80 | <1 | 113 | 122 | 100 | 92 |
| BD-001 | 11.0 | 70.2 | 293 | In89 | 92 | 75 | 2.2 | 90 | 97 | 90 | 121 |
| BD1-002 | 11.3 | 111.3 | 345 | 92 | 90 | 55 | <1 | 120 | 125 | 99 | 120 |
| BD1-005 | 10.4 | 91.4 | 342 | 99 | 98 | 84 | <1 | 128 | 132 | 115 | 105 |
| BD-00X | 10.7 | 76.3 | 236 | 94 | 75 | 91 | <1 | 102 | 101 | 83 | 85 |
| IX Deficient Plasma Samples | | | | | | | | | | | |
| HRF11P1F9 | 12.0 | 105.6 | 383 | 85 | 111 | 57 | 91 | 2 | 114 | 94 | 110 |
| HRF09-860 | 12.9 | 82.6 | 226 | 89 | 88 | 43 | 63 | 2 | 115 | 80 | 77 |
| HRF11-019 | 11.7 | 106.8 | 387 | 82 | 111 | 60 | 101 | 2 | 114 | 105 | 113 |
| GK 929-2074 | 11.8 | 113.1 | 357 | 85 | 113 | 58 | 94 | 2 | 117 | 97 | 105 |
| GK 939-2054 | 12.1 | 97.8 | 257 | 89 | 96 | 53 | 72 | 2 | 130 | 79 | 89 |

Chromogenic based Factor VIII and Factor IX assays are also insensitive to non-target coagulation factors because of the large sample dilutions and physiologically irrelevant concentrations of added coagulation factors and inhibitors.

To assess the sensitivity of the Standard FMS assay to individual phenotypic variability, four plasma samples collected from individual hemophilia A (HemA) donors after 5 day washout period (essentially 0% Factor VIII, confirmed by in-house assays) were spiked at 6 levels of rFVIIIFc (100%, 50%, 25%, 12.5%, 6.3%, 3.1%) and the clotting time was determined using the Standard FMS Factor VIII assay. The Standard FMS assay was applied using no equilibrating factors, and activation mixture comprising FIXa and Phospholipid Blend 2 (FIG. 5A) or Phospholipid Blend 8 (FIG. 5B). Although log-linear plots of rFVIIIFc concentration versus clot time for the 4 individuals displayed the same assay range and sensitivity, each of the individuals displayed a unique dose response to added rFVIIIFc.

Example 3

Alternate FMS Assay

To eliminate the observed phenotypic variability, several modifications to the Standard FMS methodology were investigated. Substitution of less sensitive phospholipid blends was able to reduce phenotypic variability. Adding a variety of purified coagulation factors, e.g., Factors II, VII, VIII, IX, X, XI, XII, XIII, fibrinogen, vWF and Tissue Factor, and inhibitors, e.g., CTI, aprotinin, ε-aminocaproic acid (EACA), D-Phenylalanyl-l-prolyl-l-arginine chloromethyl ketone-Factor VIIa (FPRCK-FVIIa), or anti-FVIII monoclonal antibodies, also was able to reduce phenotypic variability.

A variant of the Standard FMS was developed. This variant, referred to as the "Alternate FMS" assay throughout the instant disclosure was essentially designed as a hybrid between the "Standard FMS" assay and a one stage coagulation factor assay. The Alternate FMS assay also utilized an activation mixture comprising activated coagulation factor (FIXa or FXIa) combined with a phospholipid vesicle preparation and dried on the solid substrate (e.g., a disposable test strip). In the plasma based Alternate FMS assay (see FIGS. 6A and 6B), one part hemophilia plasma spiked with either rFVIIIFc or rFIXFc was mixed with three parts of a substrate plasma that had been depleted of the assay target factor. In this manner, the variability of non-target plasma components was normalized by addition of the substrate plasma.

This combination of hemophilia plasma and substrate plasma was done in an all-liquid system resulting in a four-fold dilution of the hemophilia test plasma, thus increasing the lower level of detection.

TABLE 3

Range, average precision and accuracy data for Alternate FMS Factor VIII and Factor IX Assays

| | Alternate FMS Factor VIII Assay | Alternate FMS Factor IX Assay |
| --- | --- | --- |
| Range (IU/dL) | 1.5-100 | 0.4-100 |
| Average Precision (% CV) | 1.8% | 1.0% |
| Accuracy (% Spike Recovery) | +/−10.2 | +/−11.3 |

It is anticipated that preparing a dry substrate plasma format will significantly improve the lower level of detection, since the target analyte will be four-fold higher than in the current format.

Example 4

Evaluation of Inter-Subject Variability Using the Alternate FMS Assay

To evaluate the ability of the Alternate FMS assay format to decrease inter-subject variability, 14 hemophilia A and 9 hemophilia B plasma samples were procured to conduct spike recovery studies. Plasma samples were obtained from 4 different vendors, collected by 3 different methodologies on 3 different anticoagulants. Plasma samples included immunodepleted as well as congenital hemophilia plasma. Plasma samples were also subjected to different storage conditions as well as freeze thaw cycles. The effect of a single plasma freeze thaw cycle on Alternate FMS assay performance is shown in FIGS. 7A (Alternate FMS Factor IX assay) and 7B (Alternate FMS Factor VIII assay).

In each case, samples contained 12 µL of re-calcified plasma mixed 1:3 with substrate plasma (Factor IX deficient plasma supplemented with defined levels of rFIXFc in the Alternate FMS Factor IX assay; and Factor VIII deficient plasma supplemented with defined levels of rFVIIIFc in the Alternate FMS Factor VIII assay). The results of the spike recovery studies are summarized in FIGS. 8A and 8B.

The samples presented in FIG. 8A were citrated plasma samples collected from 14 hemophilia A donors (assumed <1% Factor VIII). Plasma samples were collected at 3 sites, using 3 different methodologies and spiked with varying levels of rFVIIIFc. Each of these samples was also assayed on a laboratory reference system (MLA-1000 Coagulation Analyzer) utilizing the manufacturer's suggested reagents and calibration standard plasma traceable to the appropriate WHO standard. For hemophilia A plasmas spiked with rFVIIIFc, the theoretical values (assuming Factor VIII plasma levels supplied by vendors) were not in good agreement with values determined on the MLA. This could be related to sample quality issues, errors in the MLA assay, or errors in stock Factor VIII concentrations. For this reason, spike recovery assays for Alternate FMS Factor VIII assay in FIG. 8A were plotted as MLA value vs. Alternate FMS Factor VIII assay value (FIG. 8A). The dashed lines on the graph represented +/−20% of the MLA determined Factor VIII level. The average CV for all the Alternate FMS Factor VIII assays performed on the 14 hemophilia A donors was 3.1.

The samples presented in FIG. 8B were citrated plasma samples collected from 9 hemophilia B donors (8 donors were <1% Factor IX; 1 donor was ~34% Factor IX). Plasma samples were collected at 3 sites, using 3 different methodologies and spiked with varying levels of rFIXFc. Each of these samples was also assayed on a laboratory reference system (MLA-1000 Coagulation Analyzer) utilizing the manufacturer's suggested reagents and calibration standard plasma traceable to the appropriate WHO standard. Factor IX values and MLA values were in good agreement. Assuming the MLA value was the "true value," a plot was constructed of MLA factor concentration versus Alternate FMS Factor IX assay concentrations (FIG. 8B). The dashed lines on the graph represented +/−20% of the MLA determined Factor IX level. The average CV for the 64 determinations on 8 different instruments was 3.1% (range 0-10.2%). There was no apparent bias over the range of Factor IX concentrations (1.5-12.5 IU/dL) tested.

Assuming that the concentration determined by the MLA assay was the true value, then 61% of the Alternate FMS Factor VIII determinations and 75% of the Alternate FMS Factor IX determinations were within a +/−20% accuracy range. The average spike recovery for the Alternate FMS Factor VIII assay was +/−21% (Range 0.8-51%) and for the Alternate FMS Factor IX assay it was +/−23% (Range 0.3-98%). Assay performance was remarkable considering the non-ideal nature of the frozen plasma samples, uncertainties surrounding stock concentrations of rFVIII and rFIX products, not yet optimized test bed parameters, manual solid substrate production, and non-standardized "off the shelf" critical raw materials.

Example 5

Adaptation of Alternate FMS Assay to Whole Blood Samples

The feasibility of adapting these Alternate FMS assays to whole blood was examined in normal donors and in hemophilia A (n=4) (results shown in Example 5.1) and hemophilia B (n=1) subjects (results shown in Example 5.2).

The experimental protocol was similar for each round of testing using Alternate FMS Factor VIII and Factor IX assays. In both cases, subjects were asked to suspend factor replacement therapy for a minimum of 4 days prior to the test date. Citrated venous whole blood and fingerstick whole blood samples were collected prior to patient self-administration of their individual routine replacement therapy. A second set of citrated venous whole blood and fingerstick whole blood samples were collected and tested 20-40 minutes post infusion. Fingerstick samples, pre and post infusion were applied directly to the FMS test bed (solid substrate containing activation mixture). Aliquots of pre-infusion citrated venous blood samples were spiked with varying levels of the appropriate drug product (either rFVIIIFc or rFIXFc) and then assayed using the Alternate FMS assay. Samples were also tested on the MLA system.

Example 5.1

Adaptation of Alternate FMS Factor VIII Assay to Whole Blood Samples

The Alternate FMS Factor VIII assay was applied to six hemophilia A subjects. The results of the last 2 test events are summarized in FIGS. 9A, 9B, 10A, 10B, 10C, 11A, 11B, 12A, 12B, 13, 14A, 14B, and 14C, and TABLES 4 and 5. A direct comparison of the data in FIGS. 9A, 9B, 10A, 10B, 10C, 11A, 11B, 12A, and 12B, and FIGS. 14A, 14B, and 14C test data cannot be made owing to reagent lot changes. The major goal of the testing was to determine the feasibility of the Alternate FMS assay to mute the inter-subject variability inherent in the Standard FMS assay in whole blood samples from hemophilia A donors as it did in frozen plasma samples.

FIGS. 9A and 9B summarize an experiment in which citrated venous and fingerstick whole blood samples were collected from 2 hemophilia A subjects 5 days pre and post infusion treatment with factor replacement therapy. Samples were spiked with increasing concentrations (0 IU/dl to 200 IU/dL) of rFVIIIFc and tested utilizing the Standard FMS standard and Alternate FMS assays. Assuming both subjects' baseline FVIII values were 0 IU/dL, then the 2 hemophilia A subjects displayed disparate dose response in the Standard FMS assay. This was likely due to inter-subject variability in coagulation factors other than FVIII or to cellular components. When these same samples were run using the Alternate FMS assay, both subjects displayed similar concentration dependent clot times over the range of 1.5-200 IU/dL rFVIIIFc.

Each of the venous whole blood samples from the spike experiments described above was centrifuged to prepare plasma samples. The frozen plasma retentions were subsequently assayed on the MLA system (FIGS. 10A, 10B and 10C), using the Standard FMS Factor VIII assay (FIGS. 11A and 11B), and using the Alternate FMS Factor VIII assay (FIGS. 12A and 12B) to ascertain the relationship between FMS whole blood clot times versus plasma clot times. The trends in dose response for plasma samples mirrored those of venous whole blood samples (see FIG. 13) indicating a correlation that can be exploited for calibration purposes.

Example 5.2

Application of the Alternate FMS Factor VIII Assay to Citrated and Non-Citrated Whole Blood Samples Since the ultimate goal for the FMS assays was to use fingerstick whole blood that was not citrate anticoagulated, a comparison between citrated venous blood, citrated plasma and non-citrated fingerstick blood was performed in parallel to the previously described experiment. The results of this comparison are summarized in TABLE 4. Fingerstick whole blood samples displayed concentration-dependent clotting analogous to venous blood and plasma samples in both the Standard and the Alternate FMS methods.

TABLE 4

FMS FVIII Assays - Plasma/Venous/Fingerstick Blood Sampling Correlation

| | Standard FMS Factor VIII Assay | | Alternate FMS Factor VIII Assay | |
|---|---|---|---|---|
| | DONOR ID | | | |
| | 003 | 005 | 003 | 005 |
| | Clot Time (seconds) | | | |
| Pre-Dose (<1% FVIII) | | | | |
| Venous | >300 | >300 | 116.5 | 112.6 |
| Fingerstick | >300 | >300 | ND | ND |
| Plasma | >300 | >300 | 102.6 | 104.9 |
| Venous + 100% rFVIII-Fc Spike | 61.5 | 55.2 | 77.8 | 76.3 |
| Plasma + 100% rFVIII-Fc Spike | 45.8 | 46.5 | 64.4 | 64 |
| Post-Dose (assume 100% FVIII) | | | | |
| Venous | 65 | 56.1 | 89.1 | 83.6 |
| Fingerstick | 54.7 | 48.6 | 71.1 | ND |
| Plasma | 52.9 | 47 | 72.2 | 70.4 |

ND = Not determined

Two additional Hemophilia A donors were tested using essentially the same protocol with the following changes: (i) testing focused mainly on the Alternate FMS assay, (ii) new lots of strips and raw materials, including substrate plasma, were used in this testing, and (iii) a modified fingerstick protocol using a high flow pediatric lancet was employed. Also, plasma samples separated from the citrated venous blood were assayed prior to freezing and retesting. Samples were spiked with increasing levels (0.8-200 IU/dL) rFVIIIFc prior to assay.

The results of this second round of testing are displayed in FIGS. 14A and 14B, and TABLE 5. General assay performance was improved in these tests compared with the results from the previous round of testing shown in TABLE 4.

TABLE 5

Alternate FMS Factor VIII Assay - Plasma/Venous/Fingerstick Blood Sampling Correlation

| | Alternate Method DONOR ID | |
|---|---|---|
| | BD1-002 | BD1-004 |
| | CLOT TIME (seconds) | |
| Pre-Dose Samples | | |
| Venous Blood | >300 | >300 |
| Fingerstick Blood | >300 | >300 |
| Plasma | >300 | >300 |
| Venous + 100% rFVIII-Fc Spike | 56.7 | 57.4 |
| Plasma + 100% rFVIII-Fc Spike | 60.0 | 57.9 |
| Post Dose Samples | | |
| Venous Blood | 54.9 | 59.9 |
| Fingerstick Blood Drop 1 | 53.6 | 55.1 |
| Drop 2 | 57.7 | 61.7 |
| Plasma, Neat | 58.5 | ND |

Results indicated that, in the current format, the useful range for the Alternate FMS Factor VIII assay in venous blood is 1.5 IU/dL-200 IU/dL. The average CV for all of these determinations (n=17) was 2.1% (range 0.3-4.8) with no trend in CV with level of FVIII. As it was designed to do, the Alternate FMS Factor VIII assay displayed minimized intersubject variability thought to result from natural variations in non-Factor VIII effectors.

It is anticipated that optimization of instrument parameters to improve clot detection at the lower (<1%) range will expand the useful range of the assay to <0.5 IU/dL. Limited data on fingerstick whole blood indicated a good correlation to citrated whole blood and plasma. Experiments that follow temporal FMS fingerstick assays on post factor replacement therapy will be used to explore useful range for this format.

Example 5.3

Adaptation of Alternate FMS Factor IX Assay to Whole Blood Samples

The utility of the Alternate FMS Factor IX assay in whole blood samples was demonstrated by performing experiments analogous to those described for Factor VIII on a Hem B subject. The Hem B subject suspended Factor IX replacement therapy for 4 days prior to the test date. Citrated venous whole blood, citrated plasma, and fingerstick whole blood samples were collected pre- and post-self administration of the subject's routine Factor IX replacement therapy.

Aliquots of pre-infusion venous blood were spiked with increasing levels of rFIXFc (0-200 IU/dL) for use in constructing dose-response curves using the Alternate FMS Factor IX assay. Plasma samples separated from these samples were assayed fresh using the Alternate FMS IX assay. Frozen retentions were subsequently assayed using the Alternate FMS Factor IX assay and the MLA reference system. The results from these experiments are summarized in FIGS. 15A and 15B, and TABLE 6. The average CV for the 44 determinations performed on 8 random instruments was 1.7%. The range of CV values (0-5.8%) did not appear correlated to Factor IX levels.

The potential range in whole blood as demonstrated by the venous blood dose-response curves was 0.4 IU/dL-100 IU/dL with an average CV of 1.8%. Again, CVs were not significantly different over the entire range of the assay.

TABLE 6

Alternate FMS Factor IX Assay - Plasma/Venous/Fingerstick Blood Sampling Correlation

| | Alternate Method Factor IX Assay DONOR ID BD2-002 Clot Time (seconds) |
|---|---|
| Pre-Dose Samples | |
| Venous Blood | 90.4 |
| Fingerstick Blood | 103.5 |
| Plasma | 107.6 |
| Venous + 100% rFVIII-Fc Spike | 52.2 |
| Plasma + 100% rFVIII-Fc Spike | 53.8 |
| Post Dose Samples | |
| Venous Blood | 54.1 |
| Fingerstick Blood | 62.8 |
| Plasma, Neat | 63.4 |

Example 6

Evaluation of Instrument-to-Instrument Variability

This experiment used 8 instruments in random order for 64 determinations using the Hem A samples used in Example 4. Instrument to instrument variability was evaluated by assaying a single Factor VIII deficient plasma sample spiked to 100% and 3% rFVIIIFc in duplicate on 16 research instruments (FIG. 16). The observed CV values for the 100% spike (1.7%) and the observed CV value for the 3% spike (3.8%) were exceptional in light of the fact that no tuning was done on those instruments and the results included inter-instrument results.

Example 7

Factor Monitoring vs. PK Determination vs. Global Hemostasis Test

Accurate dotting factor level determination in patients is a technical challenge. Several approaches can be use, e.g., factor monitoring, pharmacokinetics (PK) determination, or using a global hemostasis test.

Factor monitoring can be accomplished by routine measurement of Factor VIII or Factor IX levels by finger stick at treatment center and/or at the patient's home. This approach has some advantages, e.g., it can be used for determining "traditional" PK (recovery, clearance, terminal t½, etc.), it allows long-term use by the patient or caregiver to evaluate coverage at any given time, patients and health care providers are familiar with the concept of using factor levels for dosing (or the concept is easy to adopt), and it can be used for any current Factor VIII or Factor IX products anywhere ("lab access" in developing countries, diagnostic tool). The main drawback of this approach is that it requires high accuracy and precision, which makes it the most technically challenging approach. This is due, among other factor, to high inter-patient variability of coagulation time at equivalent factor levels, which needs to be "equilibrated" or alternatively can require one-time patient-specific calibration (e.g., single lab measurement during training visit).

If using PK determination, the readout is clot time only; thus, it does not provide actual clotting factor levels. The main advantages of this approach are that it requires precision only, since accuracy for factor levels is not needed, and no patient-specific calibration needed. In general, home-use with 5-8 measurements is likely to provide more accurate PK than 1-2 laboratory tests. This approach is also less technically challenging than factor monitoring because inter-patient variability in coagulation is not relevant for calculation of terminal t½, high precision and linearity of dose response have been shown for plasma, and proof of Concept for device chemistry has been achieved. The main drawbacks of this approach are (i) lack of transparency for dose determination based on clot time, and (ii) long-term use by subject requires adoption of "global hemostasis" concepts, e.g., "Minimal clot time needed for individual hemostasis" (however, these concepts can be intuitive: "If your blood does not clot in 90 sec, you need more factor").

Determining Factor Level from Clot Time (Ct)

FIG. 17 exemplifies the use of clotting time measurements from FMS assays to determine factor levels. FMS assay results showed a linear relationship between Ct and factor levels, which can be represented according to Equation 1:

$$Ct = A \times \mathrm{Ln}(\% \text{ Factor}) + B \quad \text{[Equation 1]}$$

where the slope A was similar for all patients, at the offset B was due to patient-specific global coagulation differences.

It is possible to optimize the chemistry of the FMS assay (e.g., test strip design) to eliminate B, so there is no patient-specific offset. This approach can be used to design "ready to use" factor monitoring devices that do not require patient-specific calibration. Alternatively, the factor monitoring device can be customized for each patient by calculating B for each patient and configuring the monitoring device accordingly.

Determining Dosing Regimen Based on Clot Time (Ct)

FIG. 18 exemplifies how dosage regimens can be determined based on clotting time (Ct) determined using an FMS assay and data from population modeling, e.g., based on the A-LONG rFVIIIFc clinical trial (ClinicalTrials.gov Identifier NCT01181128) or the B-LONG rFIXFc clinical trial (ClinicalTrials.gov Identifier NCT01027364).

Half-life (HL) in terminal phase of PK can be determined according to the following set of equations:

$$Ct_1 = A \times \mathrm{Ln}(\% \ F_1) + B \quad \text{[from Equation 1]}$$

$$Ct_2 = A \times \mathrm{Ln}(\% \ F_2) + B \quad \text{[from Equation 1]}$$

$$HL = -0.693 \times (T_2 - T_1)/\mathrm{Ln}(\% \ F_1/\% \ F_2) \quad \text{[Equation 3]}$$

hence:

$$HL = -0.693 \times (T_2 - T_1) \times A/(Ct_1 - Ct_2) \quad \text{[Equation 4]}$$

where A is the slope, a device-specific parameter which would be the same for all patients. Note that the "offset" (B) becomes irrelevant, i.e., inter-patient differences in global coagulation do not affect terminal half-life.

Population modeling based on clinical trials can be used to calculate product-specific in vivo recovery and α-phase half-life (distribution phase half-life), which in turn can be used to calculate "time to trough." FMS assay derived patient-specific half-life values and "time to trough" values can in turn be used to calculate patient-specific dose and dose interval.

Global Hemostasis Test Based on FMS Assay

The FMS assays described above have been used to develop a global hemostasis test. The FMS assays disclosed herein measure an individual's overall clotting potential at any given level of coagulation factor. Proof of concept, sensitivity and range of the FMS assays have been established as shown in the examples above. Furthermore, no external dilution is performed as there is no need to equilibrate patient-specific differences.

As shown above in Equation 3, an increase in Ct as clotting factor is cleared over time correlates with terminal half-life (HL). Individual clot time at trough ($Ct_{trough}$) is a critical parameter to establish in each patient. With known patient-specific HL and $Ct_{trough}$, the "time to trough" (T) after any measured Ct is then predictable and can be calculated according to the following formula:

$$T = -1.44 \times HL/(A \times (Ct_{measured} - Ct_{trough})) \quad \text{[Equation 5]}$$

The time to trough (T) would correspond to the time to the next dose.

CONCLUSIONS

If the primary purpose of the application of the FMS assay is to define the initial dosing regimen, a precise readout of clot time is sufficient. There is no need for accuracy or patient-specific calibration for terminal t½. To determine other PK parameters (e.g., recovery and clearance) in individual patients, accurate factor levels are required, however.

"Minimal clot time needed for hemostasis" can be an important biomarker for the individual patient. Once the FMS assay has been applied to measure (i) individual Ct at trough and (ii) change in Ct over time (i.e., individual terminal PK), estimating the "time to trough" (time to next dose) based on a single Ct measurement is expected to be very accurate.

It is to be appreciated that the Detailed Description section, and not the Summary and Abstract sections, is intended to be used to interpret the claims. The Summary and Abstract sections can set forth one or more but not all exemplary aspects of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary aspects, but should be defined only in accordance with the following claims and their equivalents.

SEQUENCE TABLE 1

| Polynucleotide Sequences: FIX-Fc |
|---|

A. B-Domain Deleted FVIIIFc
A(i). B-Domain Deleted FVIIIFc Chain DNA Sequence (FVIII signal peptide underlined, Fc region in bold) (SEQ ID NO: 1, which encodes SEQ ID NO: 2)

<u>atgcaaatagagctctccacctgcttctttctgtgccttttgcgattctgctttagt</u>gccaccagaagatactacctg
ggtgcagtggaactgtcatgggactatatgcaaagtgatctcggtgagctgcctgtggacgcaagatttcctcctaga
gtgccaaaatcttttccattcaacacctcagtcgtgtacaaaaagactctgtttgtagaattcacggatcaccttttc
aacatcgctaagccaaggccaccctggatgggtctgctaggtcctaccatccaggctgaggtttatgatacagtggtc
attacacttaagaacatggcttccatcctgtcagtcttcatgctgttggtgtatcctactggaaagcttctgaggga
gctgaatatgatgatcagaccagtcaaagggagaaagaagatgataaagtcttccctggtggaagccatacatatgtc
tggcaggtcctgaaagagaatggtccaatggcctctgacccactgtgccttacctactcatatctttctcatgtggac
ctggtaaaagacttgaattcaggcctcattggagccctactagtatgtagagaagggagtctggccaaggaaaagaca
cagaccttgcacaaatttatactacttttttgctgtatttgatgaagggaaaagttggcactcagaaacaaagaactcc
ttgatgcaggatagggatgctgcatctgctcgggcctggcctaaaatgcacacagtcaatggttatgtaaacaggtct
ctgccaggtctgattggatgccacaggaaatcagtctattggcatgtgattggaatgggcaccactcctgaagtgcac
tcaatattcctcgaaggtcacacatttcttgtgaggaaccatcgccaggcgtccttggaaatctcgccaataactttc
cttactgctcaaacactcttgatggacctggacagtttctactgttttgtcatatctcttcccaccaacatgatggc
atggaagcttatgtcaaagtagacagctgtccagaggaaccccaactacgaatgaaaaataatgaagaagcggaagac
tatgatgatgatcttactgattctgaaatggatgtggtcaggtttgatgatgacaactctccttccttttatccaatt
cgctcagttgccaagaagcatcctaaaacttgggtacattacattgctgctgaagaggaggactgggactatgctccc
ttagtcctcgcccccgatgacagaagttataaaagtcaatatttgaacaatggccctcagcggattggtaggaagtac
aaaaaagtccgatttatggcatacacagatgaaacctttaagactcgtgaagctattcagcatgaatcaggaatcttg
ggacctttacttatggggaagttggagacacactgttgattatatttaagaatcaagcaagcagaccatataacatc
taccctcacggaatcactgatgtccgtcctttgtattcaaggagattaccaaaaggtgtaaaacatttgaaggatttt
ccaattctgccaggagaaatattcaaatataaatggacagtgactgtagaagatgggccaactaaatcagatcctcgg
tgcctgacccgctattactctagtttcgttaatatggagagagatctagcttcaggactcattggccctctcctcatc
tgctacaaagaatctgtagatcaaagaggaaaccagataatgtcagacaagaggaatgtcatcctgttttctgtattt
gatgagaaccgaagctggtacctcacagagaatatacaacgctttctccccaatccagctggagtgcagcttgaggat
ccagagttccaagcctccaacatcatgcacagcatcaatggctatgtttttgatagtttgcagttgtcagtttgtttg
catgaggtggcatactggtacattctaagcattggagcacagactgacttccttctgtcttcttctctggatatacc
ttcaaacacaaaatggtctatgaagacacactcaccctattccattctcaggagaaactgtcttcatgtcgatggaa
aacccaggtctatggattctggggtgccacaactcagacttcggaacagaggcatgaccgccttactgaaggtttct
agttgtgacaagaacactggtgattattacgaggacagttatgaagatatttcagcatacttgctgagtaaaaacaat
gccattgaaccaagaagcttctctcaaaacccaccagtcttgaaacgccatcaacgggaaataactcgtactactctt
cagtcagatcaagaggaaattgactatgatgataccatatcagttgaaatgaagaaggaagattttgacatttatgat
gaggatgaaaatcagagcccccgcagctttcaaaagaaaacacgacactattttattgctgcagtggagaggctctgg
gattatgggatgagtagctccccacatgttctaagaaacagggctcaggtgtcccctcagttcaagaaagtt
gttttccaggaatttactgatggctccttactcagcccttataccgtggagaactaaatgaacatttgggactcctg
gggccatatataagagcagaagttgaagataatatcatggtaactttcagaaatcaggcctctcgtccctattcctc
tattctagccttatttcttatgaggaagatcagaggcaaggagcagaacctagaaaaaactttgtcaagcctaatgaa
accaaaacttacttttggaaagtgcaacatcatatggcacccactaaagatgagtttgactgcaaagcctggcttat
ttctctgatgttgacctggaaaaagatgtgcactcaggcctgattggaccccttctggtctgccacactaacacactg
aaccctgctcatgggagacaagtgacagtacaggaatttgctctgttttccaccatctttgatgagaccaaaagctgg
tacttcactgaaaatatggaaagaaactgcagggctccctgcaatatccagatggaagatcccactttaaagagaat
tatcgcttccatgcaatcaatggctacataatggatacactacctggcttagtaatggctcaggatcaaaggattcga
tggtatctgctcagcatgggcagcaatgaaaacatccattctattcatttcagtggacatgtgttcactgtacgaaaa
aagagaggatataaatggcactgtacaactctctatccaggtgttttcgaggtgttttaccatccaaagct
ggaatttggcgggtggaatgccttattggcgagcatctacatgctgggatgagcacacttttctggtgtacagcaat
aagtgtcagactcccctgggaatggcttctggacacattagagattttcagattacagctcaggacaatatggacag
tgggcccaaagctggccagacttcattattccggatcaatcaatgcctggagcaccaaggagccctttttcttggatc
aaggtggatctgttggcaccaatgattattcacggcatcaagacccaggtgcccgtcagaagttctccagcctctac
atctctcagtttatcatcatgtatagtcttgatgggaagaagtggcaaactcctcgaggaaattccactggaaccctta
atggtcttctttggcaatgtggattcatctgggataaaaacaatatttttaaccctccaattattgctcgatacatc
cgtttgcacccaactcattatagcattcgcagcactcttcgcatggagttgatgggctgtgatttaaatagttgcagc
atgccattgggaatggagagtaaagcaatatcagatgcacagattactgcttcatcctactttaccaatatgtttgcc
acctggtctccttcaaaagctcgacttcacctccaagggaggagtaatgcctggagacctcaggtgaataatccaaaa
gagtggctgcaagtggacttccagaagacaatgaaagtcacaggagtaactactcagggagtaaaatctctgcttacc
agcatgtatgtgaaggagttcctcatctccagcagtcaagatggacatctcttttttcagaatggcaaa
gtaaaggtttttcagggaaatcaagactccttcacacctgtggtgaactctctagccccaccgttactgactcgctac
cttcgaattcaccccccagagtggtgcaccagattgccctgaggatggaggttctgggctgcgaggcacaggacctc
tacgacaaaactcacacatgccccaccgtgcccagctccagaactcctgggcggaccgtcagtcttcctcttccccca
aaacccaaggacaccctcatgatctcccggacccctgaggtcacatgcgtggtggtggacgtgagccacgaagaccct
gaggtcaagttcaactggtacgtggacggcgtggaggtgcataatgccaagacaaagccgcggggaggagcagtacaac
agcacgtaccgtgtggtcagcgtcctcaccgtcctgcaccaggactggctgaatggcaaggagtacaagtgcaaggtc
tccaacaaagccctcccagcccccatcgagaaaaccatctccaaagccaaagggcagccccgagaaccacaggtgtac
accctgcccccatcccgggatgagctgaccaagaaccaggtcagcctgacctgcctggtcaaaggcttctatcccagc
gacatcgccgtggagtgggagagcaatgggcagccggagaacaactacaagaccacgcctcccgtgttggactccgac
ggctccttcttcctctacagcaagctcaccgtggacaagagcaggtggcagcaggggaacgtcttctcatgctccgtg
atgcatgaggctctgcacaaccactacacgcagaagagcctctccctgtctccgggtaaa

SEQUENCE TABLE 1-continued

Polynucleotide Sequences: FIX-Fc

A(ii). Fc DNA sequence (mouse Igκ signal peptide underlined) (SEQ ID NO: 3), which encodes SEQ ID NO: 4)

<u>atggagacagacacactcctgctatgggtactgctgctctgggttccaggttccactggt</u>gacaaaactcacacatgc
ccaccgtgcccagcacctgaactcctgggaggaccgtcagtcttcctcttccccccaaaacccaaggacaccctcatg
atctcccggacccctgaggtcacatgcgtggtggtggacgtgagccacgaagaccctgaggtcaagttcaactggtac
gtggacggcgtggaggtgcataatgccaagacaaagccgcgggaggagcagtacaacagcacgtaccgtgtggtcagc
gtcctcaccgtcctgcaccaggactggctgaatggcaaggagtacaagtgcaaggtctccaacaaagcccTcccagcc
cccatcgagaaaaccatctccaaagccaaagggcagccccgagaaccacaggtgtaccccctgcccccatcccgcgat
gagctgaccaagaaccaggtcagcctgacctgcctggtcaaaggcttctatcccagcgacatcgccgtggagtgggag
agcaatgggcagccggagaacaactacaagaccacgcctcccgtgttggactccgacggctccttcttcctctacagc
aagctcaccgtggacaagagcaggtggcagcaggggaacgtcttctcatgctccgtgatgcatgaggctctgcacaac
cactacacgcagaagagcctctccctgtctccgggtaaa B. Full Length FVIIIFc B(i). Full Length FVIIIFc DNA Sequence (FVIII signal peptide underlined, Fc region in bold) (SEQ ID NO: 5, which encodes SEQ ID NO: 6)

<u>atgcaaatagagctctccacctgcttctttctgtgccttttgcgattctgctttagt</u>gccaccagaagatactacctg
ggtgcagtggaactgtcatgggactatatgcaaagtgatctcggtgagctgcctgtggacgcaagatttcctcctaga
gtgccaaaatcttttccattcaacacctcagtcgtgtacaaaaagactctgtttgtagaattcacggatcaccttttc
aacatcgctaagccaaggcccccctggatgggtctgctaggtcctaccatccaggctgaggtttatgatacagtggtc
attacacttaagaacatggcttccatcctgtcagtcttcatgctgttggtgtatcctactggaaagcttctgagggga
gctgaatatgatgatcagaccagtcaaagggaagaagatgataaagtcttccctggtggagagccatacatatgtc
tggcaggtcctgaaagagaatggtccaatggcctctgacccactgtgccttacctactcatatctttctcatgtggac
ctggtaaaagacttgaattcaggcctcattggagccctactagtatgtagagaagggagtctggccaaggaaaagaca
cagaccttgcacaaatttatactacttttttgctgtatttgatgaagggaaaagttggcactcagaaacaaagaactcc
ttgatgcaggatagggatgctgcatctgctcgggcctggcctaaaatgcacacagtcaatggttatgtaaacaggtct
ctgccaggtctgattggatgccacaggaaatcagtctattggcatgtgattggaatgggcaccactcctgaagtgcac
tcaatattcctcgaaggtcacacatttcttgtgaggaaccatcgccaggcgtccttggaaatctcgccaataactttc
cttactgctcaaacactcttgatggaccttggacagtttctactgttttgtcatatctcttcccaccaacatgatggc
atggaagcttatgtcaaagtagacagctgtccagaggaaccccaactacgaatgaaaaataatgaagaagcggaagac
tatgatgatgatcttactgattctgaaatggatgtggtcaggtttgatgatgacaactctcccttccttatccaaatt
cgctcagttgccaagaagcatcctaaaacttgggcatatcattgctgctgaagaggaggactgggactatgctccc
ttagtcctcgcccccgatgacagaagttataaagtcaatatttgaacaatggccctcagcggattggtaggaagtac
aaaaagtccgatttatggcatacacagatgaaacctttaagactcgtgaagctattcagcatgaatcaggaatcttg
ggacctttacttatgggaagttggagacaacactgttgattatttaagaatcaagcaagcagaccatataacatc
taccctcacggaatcactgatgtccgtcctttgtattcaaggagattaccaaaaggtgtaaaacatttgaaggatttt
ccaattctgccaggagaaatattcaaatataaatggacagtgactgtagaagatgggccaactaaatcagatcctcgg
tgcctgacccgctattactctagtttcgttaatatggagagagatctagcttcaggactcattggccctctcctcatc
tgctacaaagaatctgtagatcaaagaggaaaccagataatgtcagacaaggaaatgtcatcctgttttctgtattt
gatgagaaccgaagctggtacctcacagagaatatacaacgctttctccccaatccagctggagtgcagcttgaggat
ccagagttccattgtttgcatgaggtggcatactggtacattctaagcattggagcacagactgacttcctttctgtc
ttcttctctggatataccttcaaacacaaaatggtctatgaagacacactcaccctattccattctcaggagaaact
gtcttcatgtcgatggaaaacccaggtctatggattctggggtgccacaactcagacttcggaacagaggcatgacc
gccttactgaaggtttctagttgtgacaagaacactggtgattattacgaggacagttatgaagatatttcagcatac
ttgctgagtaaaaacaatgccattgaaccaagaagcttctcccagaattcaagcacccTagcactaggcaaaagcaa
tttaatgccaccacaattccagaaaatgacatagagaagactgacccttggtttgcacacagaacacctatgcctaaa
atacaaaatgtctcctctagtgatttgttgatgctctgcgacagagttcctactccacatgggctatccttatctgat
ctccaagaagccaaatatgagacttttttctgatgatcacatcccctggagcaatagacagtaataacagcctgtctgaa
atgacacactcaggccacagctccatcacagtggggacatggtatttaccctgagtcaggcctccaattaagatta
aatgagaaactggggacaactgcagcaacagagttgaagaaacttgatttcaaagtttctagtacatcaaataatctg
atttcaacaattccatcagacaatttggcagcaggtactgataatacaagttccttaggacccccaagtatgccagtt
cattatgatagtcaattagataccactctatttggcaaaaagtcatctccccttactgagtctggtggacctctgagc
ttgagtgaagaaataatgattcaaagttgttagaatcaggtttaatgaatagcaagaaagttcatgggaaaaat
gtatcgtcaacagagtggtaggttatttaaagggaaaagagctcatggacctgctttgttgactaaagataatgcc
ttattcaaagttagcatctctttgttaaagacaaacaaaacttccaataattcagcaactaatagaaagactcacatt
gatggcccatcattattaattgagaatagtccatcagtctgcaaatatattaagaaagtgacactgagttttaaaaaa
gtgacacctttgattcatgacagaatgcttatggacaaaaatgctacagctttgaggctaaatcatatgtcaaataaa
actacttcatcaaaaaacatggaaatggtccaacagaaaaagaggccccattccaccagatgcacaaatccagat
atgtcgttcttttaagatgctattcttgccagaatcagcaaggtggatacaaaggactcatggaaagaactctctgaac
tctgggcaaggccccagtccaaagcaattagtatccttaggaccagaaaatctgttgaagagtcagaatttcttgtct
gagaaaaacaaagtggtagtaggaaagggtgaatttacaaaggacgtaggactcaaagagatggtttttccaagcgc
agaaacctatttcttactaacttggataatttacatgaaataatacacacaatcaagaaaaaaaattcaggaagaa
atagaaaagaaggaaacattaatccaagagaatgtagttttgcctcagatacatacagtgactggcactaagaattttc
atgaagaaccttttcttactgagcactaggcaaaatgtagaaggttcatatgacggggcatatgctcctcagtacttcaa
gatttaggtcattaaatgattcaacaaatagaacaaagaaacacacagctcatttctcaaaaaagggggaggaagaa
aacttggaaggcttgggaaatcaaacccaagcaaattgtagagaaatgcatgcaccacaaggatatctcctaatacc
agccagcagaattttgtcacgcaacgtagtaagagagctttgaaacaattcagactcccactagaagaaacagaactt
gaaaaaagataattgtggatgacacctcaacccagtggtccaaaaacatgaaacattgacccgagcaccctcaca
cagatagactacaatgagaaggagaaaggggccattactcagtctccTtatcagattgccttacgaggagtcatagc
atccctcaagcaaatagatctccattacccattgcaaggtatcatcatttccatctattagacctatatctgacc
agggtcctattccaagacaactcttctcatcttccagcagcatcTtatgaaagaaaggattctgggtccaagaaagc
agtcatttcttacaaggagcaaaaaaaataacctttctTtagccattcatgagtttgagatgactgctgGGGatcaaga
gaggttggctccctggggacaagtgccacaaattcagtcacataccagaaaagttgagaacactgttctcccgaaacca
gacttgcccaaaacatctggcaaagttgaattgcttccaaaagttcacatttatcagaaggaccTattccctacggaa
actagcaatgggtctcctggccatctggatctcgtggaagggagccttcttcagggaacagagggagcgattaagtgg
aatgaagcaaacagacctggaaaagttcccttcctgagagtagcaacagaaagctctgcaaagactcccccaagcta
ttggatcctcttgcttgggataaccactatggtactcagataccaaaagaagagtggaaatcccaagagaagtcacca SEQUENCE TABLE 1-continued Polynucleotide Sequences: FIX-Fc gaaaaaacagcttttaagaaaaaggataccattttgtccctgaacgcttgtgaaagcaatcatgcaatagcagcaata
aatgagggacaaaataagcccgaaatagaagtcacctgggcaaagcaaggtaggactgaaaggctgtgctctcaaaac
ccaccagtcttgaaacgccatcaacgggaaataactcgtactactcttcagtcagatcaagaggaaattgactatgat
gataccatatcagttgaaatgaagaaggaagattttgacattatgatgaggatgaaaatcagagccccccgcagcttt
caaaagaaaacacgacactattttattgctgcagtggagaggctctgggattatgggatgagtagctccccacatgtt
ctaagaaacagggctcagagtggcagtgtccctcagttcaagaaagttgttttccaggaatttactgatggctccttt
actcagccctatacccgtggagaactaaatgaacattttgggactcctggggccatatataagagcagaagttgaagat
aatatcatggtaactttcagaaatcaggcctctcgtcccattccttctattctagccttattcttatgaggaagat
cagaggcaaggagcagaacctagaaaaaacttgtcaagcctaatgaaccaaaacttacttttggaaagtgcaacat
catatggcacccactaaagatgagtttgactgcaaagcctgggcttatttctctgatgttgacctggaaaagatgtg
cactcaggcctgattggacccctttctggtctgccacactaacacactgaaccctgctcatgggagacaagtgacagta
caggaatttgctctgttttttccaccatctttgatgagaccaaaagctggtacttcactgaaaatatgaaagaaactgc
agggctccctgcaatatccagatggaagatcccactttaaagagaattatcgcttccatgcaatcaatggctacata
atggatacactacctggcttagtaatggctcaggatcaaaggattcgatggtatctgctcagcatgggcagcaatgaa
aacatccattctattcatttcagtggacatgtgttcactgtacgaaaaaaaagaggagtatataaatggcactgtacaat
ctctatccaggtgttttgagacagtggaaatgttaccatccaaagctggaatttggcgggtggaatgccttattggc
gagcatctacatgctgggatgagcacacttttctggtgtacagcaataagtgtcagactccctgggaatggcttct
ggacacattagagattttcagattacagcttcaggacaatatggacagtgggcccaaagctggccagacttcattat
tccggatcaatcaatgcctggagcaccaaggagcccttttcttggatcaaggtggatctgttggcaccaatgattatt
cacggcatcaagacccagggtgcccgtcagaagttctccagcctctacatctctcagtttatcatcatgtatagtctt
gatgggaagaagtggcagacttatcgaggaaattccactggaaccttaatggtcttctttggcaatgtggattcatct
gggataaaacacaatatttttaaccctccaattattgctcgatacatccgtttgcacccaactcattatagcattcgc
agcactcttcgcatggagttgatgggtcgtgatttaaataagttgcagcatgccattgggaatggagagtaaagcaata
tcagatgcacagattactgcttcatcctactttaccaatatgtttgccacctggtctccttcaaaagctcgacttcac
ctccaagggaggagtaatgcctggagacctcaggtgaataatccaaaagagtggctgcaagtggacttccagaagaca
atgaaagtcacaggagtaactactcagggagtaaaatctctgcttaccagcatgtatgtgaaggagttcctcatctcc
agcagtcaagatggccatcagtggactctcttttttcagaatggcaaagtaaaggtttttcagggaaatcaagactcc
ttcacacctgtggtgaactctctagacccaccgttactgactcgctaccttcgaattcaccccccagagttgggtgcac
cagattgccctgaggatggaggttctgggctgcgaggcacaggacctctac**gacaaaactcacacatgcccaccgtgc
ccagctccagaactcctgggcggaccgtcagtcttcctcttccccccaaaacccaaggacaccctcatgatctcccgg
acccctgaggtcacatgcgtggtggtggacgtgagccacgaagaccctgaggtcaagttcaactggtacgtggacggc
gtggaggtgcataatgccaagacaaagccgcgggaggagcagtacaacagcacgtaccgtgtggtcagcgtcctcacc
gtcctgcaccaggactggctgaatggcaaggagtacaagtgcaaggtctccaacaaagcccccagccccatcgag
aaaaccatctccaaagccaaagggcagccccgagaaccacaggtgtacaccctgcccccatcccgggatgagctgacc
aagaaccaggtcagcctgacctgcctggtcaaaggcttctatcccagcgacatcgccgtggagtgggagagcaatggg
cagccggagaacaactacaagaccacgcctcccgtgttggactccgacggctccttcttcctctacagcaagctcacc
gtggacaagagcaggtggcagcaggggaacgtcttctcatgctccgtgatgcatgaggctctgcacaaccactacacg
cagaagagcctctccctgtctccgggtaaa**

C(i). Heavy Chain (HC)-Fc DNA sequence (no linker between HC and Fc) (signal peptide
underlined, Fc region in bold) (SEQ ID NO: 7, which encodes SEQ ID NO: 8)
<u>atgcaaatagagctctccacctgcttctttctgtgccttttgcgattctgctttagtgccaccagaagatactacctg</u>
ggtgcagtggaactgtcatgggactatatgcaaagtgatctcggtgagctgcctgtggacgcaagatttcctcctaga
gtgccaaaatcttttccattcaacacctcagtcgtgtacaaaagactctgtttgtagaattcacggatcaccttttc
aacatcgctaagcaaggccaccctggatgggtctgctaggtcctaccatccaggctgaggtttatgatacagtggtc
attacacttaagaacatggcttcccatcctgtcagtcttcatgctgttggtgtatcctactggaaagcttctgaggga
gctgaatatgatgatcagaccagtcaaagggagaaagaagatgataaagtcttccctggtggaagccatacatatgtc
tggcaggtcctgaaagagaatggtccaatggcctctgacccactgtgccttacctactcatatctttctcatgtggac
ctggtaaaagacttgaattcaggcctcattggagccctactagtatgtagagagggagtctggccaaggaaaagacac
agaccttgcacaaatttatactacttttgctgtatttgatgaaggggaaactggcactcagaaacaaagaactcct
tgatgcaggatagggatgctgcatctgctcgggcctggcctaaaatgcacacagtcaatggttatgtaaacaggtctc
tgccaggtctgattggatgccacaggaaatcagtctattggcatgtgattggaatgggcaccactcctgaagtgcact
caatattcctcgaaggtcacacattcttgtgaggaaccatcgccaggcgtccttggaaatctgccaataactttcc
ttactgctcaaaacactcttgatggaccttggacagtttctactgttttgtcatatctcttcccaccaacatgatggca
tggaagcttatgtcaaagtagacagcttgccagaggaacccccaactacgaatgaaaaataatgaagaagcggaagact
atgatgatgatcttactgattctgaaatggatgtggtcaggtttgatgatgacaactctccttcctttatccaaattc
gctcagttgccaagaagcatcctaaaacttgggtacattacattgctgctgaagaggaggactgggactatgctccct
tagtcctcgcccccgatgacagaagttataaaagtcaatatttgaacaatggccctcagcggattggtaggaagtaca
aaaagtccgatttatggcatacacagatgaaaccttaagactcgtgaagctattcagcatgaatcaggaatcttgg
gacctttacttatggggaagttggagacacactgttgattatattaagaatcaagcaagcagaccatataacatct
accctcacggaatcactgatgtccgtccttgtattcaaggagattaccaaaaggtgtaaaacatttgaaggattc
caattctgccaggagaaatattcaaatataaatggacagtgactgtagaagatgggccaactaaatcagatcctcggt
gcctgacccgctattactctagtttcgttaatatggagagatctagcttcaggactcattggccctctcctcatct
gctacaaagaatctgtagatcaaagaggaaaccagataatgtcagacaagaggaatgtcatcctgttttctgtatttg
atgagaaccgaagctggtacctcacagagaatatacaacgctttctcccaatccagctggagtgcagcttgaggatc
cagagttccaagcctccaacatcatgcacagcatcaatggctatgtttttgatagtttgcagttgtcagttgtttgc
atgaggtggcatactggtacattctaagcattggagcacagactgacttcctttctgtcttcttctctggatataccct
tcaaacacaaaatggtctatgaagacacactcacccctattcccattctcaggagaaactgtcttcatgtcgatggaaa
acccaggtctatggattctggggtgccacaactcagactttcggaacagaggcatgaccgccttactgaaggtttcta
gttgtgacaagaacactggtgattattacgaggacagttatgaagatatttcagcatacttgctgagtaaaaacaatg
ccattgaaccaagacaaaactcacacatgcccaccgtgcccagctccagaactcacacatgcccaccgtgcccagctcc
tcttcccccaaaacccaaggacaccctcatgatctcccgaccctgaggtcacatgcgtggtggtggacgtgagcc
acgaagaccctgaggtcaagttcaactggtacgtggacggcgtggaggtgcataatgccaagacaaagccgcgggagg
agcagtacaacagcacgtaccgtgtggtcagcgtcctcaccgtcctgcaccaggactggctgaatggcaaggagtaca
agtgcaaggtctccaacaaagcccccagccccatcgagaaaaccatctccaaagccaaagggcagccccgagaac
cacaggtgtacaccctgcccccatcccgggatgagctgaccaagaaccaggtcagcctgacctgcctggtcaaaggct SEQUENCE TABLE 1-continued Polynucleotide Sequences: FIX-Fc tctatcccagcgacatcgccgtggagtgggagagcaatgggcagccggagaacaactacaagaccacgcctcccgtgt
tggactccgacggctccttcttcctctacagcaagctcaccgtggacaagagcaggtggcagcaggggaacgtcttct
catgctccgtgatgcatgaggctctgcacaaccactacacgcagaagagcctctccctgtctccgggtaaa C(ii). Heavy Chain (HC)-Fc DNA sequence (5 amino acid linker between HC and Fc) (signal
peptide underlined, Fc region in bold, 5 amino acid linker is double-underlined)
(SEQ ID NO: 9, which encodes SEQ ID NO: 10)
<u>atgcaaatagagctctccacctgcttctttctgtgccttttgcgattctgctttagt</u>gccaccagaagatactacctg
ggtgcagtggaactgtcatgggactatatgcaaagtgatctcggtgagctgcctgtggacgcaagatttcctcctaga
gtgccaaaatcttttccattcaacacctcagtcgtgtacaaaaagactctgtttgtagaattcacggatcaccttttc
aacatcgctaagccaaggccaccctggatgggtctgctaggtcctaccatccaggctgaggtttatgatacagtggtc
attacacttaagaacatggcttcccatcctgtcagtcttcatgctgttggtgtatcctactggaaagcttctgaggga
gctgaatatgatgatcagaccagtcaaagggagaaagaagatgataaagtcttccctggtggaagccatacatatgtc
tggcaggtcctgaaagagaatggtccaatggcctctgacccactgtgccttacctactcatatctttctcatgtggac
ctggtaaaagacttgaattcaggcctcattggagccctactagtatgtagagaaggagctggccaaggaaaagaca
cagaccttgcacaaatttatactacttttgctgtatttgatgaaggaaagttggcactcagaaacaaagaactcc
ttgatgcaggatagggatgctgcatctgctcgggcctggcctaaaatgcacacagtcaatggttatgtaaacaggtct
ctgccaggtctgattggatgccacaggaaatcagtctattggcatgtgattggaatgggcaccactcctgaagtgcac
tcaatattcctcgaaggtcacacatttcttgtgaggaaccatccgcaggcgtccttggaaatctcgccaataactttc
cttactgctcaaacactcttgatggacctggacagtttctactgttttgtcatatctcttcccaccaacatgatggc
atggaagcttatgtcaaagtagacagctgtccagaggaaccccaactacgaatgaaaaataatgaagaagcggaagac
tatgatgatgatcttactgattctgaaatggatgtggtcaggtttgatgatgacaactctccttcctttatccaatt
cgctcagttgccaagaagcatcctaaaacttgggtacattacattgctgctgaagaggaggactggactatgctccc
ttagtcctcgcccccgatgacagaagttataaaagtcaatatttgaacaatggccctcagcggattggtaggaagtac
aaaaaagtccgatttatggcatacacagatgaaacctttaagactcgtgaagctattcagcatgaatcaggaatcttg
ggacctttactttatgggaagttggagacacactgttgattatatttaagaatcaagcaagcagaccatataacatc
tacccctcacggaatcactgatgtccgtccttttgtattcaaggagattaccaaaaggtgtaaaacatttgaaggattt
ccaattctgccaggagaaatattcaaatataaatggacagtgactgtagaagatgggccaactaaatcagatcctcgg
tgcctgaccgctattactctagtttcgttaatatggagagagatctagcttcaggactcattggcctctcctcatc
tgctacaaagaatctgtagatcaaagaggaaaccagataatgtcagacaagaggaatgtcatcctgttttctgtattt
gatgagaaccgaagctggtacctcacagagaatatacaacgctttctccccaatccagctggagtgcagcttggaggat
ccagagttccaagcctccaacatcatgcacagcatcaatggctatgttttttgatagtttgcagttgtcagtttgtttg
catgaggtggcatactggtacattctaagcattggagcacagactgacttcctttctgtcttcttctctggatatacc
ttcaaacacaaaatggtctatgaagacacactcacccctattccattctcaggagaaactgtcttcatgtcgatggaa
aacccaggtctatggattctggggtgccacaactcagactttcggaacagaggcatgaccgccttactgaaggtttct
agttgtgacaagaacactggtgattattacgaggacagttatgaagatatttcagcatacttgctgagtaaaaacaat
gccattgaaccaagaa<u>agcttctcccagaat</u>gacaaaactcacacatgcccaccgtgcccagctccagaactcctgggc
ggaccgtcagtcttcctcttccccccaaaacccaaggacaccctcatgatctcccggacccctgaggtcacatgcgtg
gtggtggacgtgagccacgaagaccctgaggtcaagttcaactggtacgtggacggcgtggaggtgcataatgccaag
acaaagccgcggaggaggcagtacaacagcacgtaccgtgtggtcagcgtcctcaccgtcctgcaccaggactggctg
aatggcaaggagtacaagtgcaaggtctccaacaaagccctcccagcccccatcgagaaaaccatctccaaagccaaa
gggcagccccgagaaccacaggtgtacaccctgcccccatcccgggatgagctgaccaagaaccaggtcagcctgacc
tgcctggtcaaaggcttctatcccagcgacatcgccgtggagtgggagagcaatgggcagccggagaacaactacaag
accacgcctcccgtgttggactccgacggctccttcttcctctacagcaagctcaccgtggacaagagcaggtggcag
caggggaacgtcttctcatgctccgtgatgcatgaggctctgcacaaccactacacgcagaagagcctctccctgtct
ccgggtaaa C(iii). Light Chain (LC)-Fc DNA sequence (signal peptide underlined, Fc region in bold)
(SEQ ID NO: 11, which encodes SEQ ID NO: 12)
<u>atggagacagacacactcctgctatgggtactgctgctctgggttccaggttccactggt</u>gaaataactcgtactact
cttcagtcagatcaagaggaaattgactatgatgataccatatcagttgaaatgaagaaggaagatttgacatttat
gatgaggatgaaatcagagccccccgcagctttcaaaagaaaacacgacactatttattgctgcagtggagaggctc
tgggattatgggatgagtagctccccacatgttctaagaaacagggctcagagtggcagtcgtccctcagttcaagaaa
gttgttttccaggaatttactgatggctcctttactcagcccttataccgtggagaactaaatgaacatttgggactc
ctggggccatatataagagcagaagttgaagataatatcatggtaactttcagaaatcaggcctctcgtccctattcc
ttctattctagccttatttcttatgaggaagatcagaggcaaggagcagaacctagaaaaaactttgtcaagcctaat
gaaaccaaaacttacttttgggaaagtgcaacatcatatggcaacccactaaagtgagtttgactgcaaagcctgggct
tatttctctgatgttgacctgaaaaagatgtgcactcaggcctgattggaccccttctggtctgccacactaacaca
ctgaaccctgctcatgggagacaagtgacagtacaggaatttgctctgttttttcaccatctttgatgagaccaaaagc
tggtacttcactgaaaatatgaaagaaactgcagggctccctgcaatatccagatggaagatcccactttaaagag
aattatcgcttccatgcaatcaatggctacataatggctacacctccttaggtctggctgcaggatcaaagatt
cgatggtatctgctcagcatgggcagcaatgaaaacatccattctattcattcagtggacatgtgttcactgtacga
aaaaagaggagtaaaatggcactgtacaatctctatccaggtgttttgagacagtggaaatgttaccatccaaa
gctggaatttggcgggtggaatgccttattggcgagcatctacatgctgggatgagcacttttctggtgtacagc
aataagtgtcagactccctgggaatggcttctgacacattagaatttctggattacagcttcaggacaatatgga
cagtgggccccaaagctggccagacttcattattccggatcaatcaatgcctggacaccaaggagccttttcttgg
atcaaggtggatctgttggcaccaatgattattcacggcatcaagacccagggtgcccgtcagaagtctccagcctc
tacatctctcagtttatcatcatgtatagtcttgatgggaagaagtggcagacttatcgaggaaattccactggaacc
ttaatggtcttcttttggcaatgtggattcatctgggataaaaacacaatattttaaccctccaattattgctcgatac
atccgtttgcacccaactcattatagcattcgcagcactcttcgcatggagtttgatgggctgtgatttaaatagttgc
agcatgccattgggaatggagagtaaagcaatatcagatgcacagattactgcttcatcctactttaccaatatgttt
gccacctggtctccttcaaaagctcgacttcacctccaagggaggtaatgcctggagacctcaggtgaataatcca
aaagatggctgcaagtgacttcagaagacaatgaaagtgcagggtaactactcagggagtaaaatctctgctt
accagcatgtatgtgaaggagttcctcatctccagcagtcaagatggcactggatctctctttttcagaatggc
aaagtaaaggttttcagggaaatcaagactccttcacacctgtggtgaactctctagacccaccgtactgactcgc
taccttcgaattcaccccagagtgggtgcaccagattgccctgaggatggaggttctgggctgcgaggcacaggac
ctctacgacaaaactcacacatgcccaccgtgcccagctccagaactcctgggcggaccgtcagtcttcctcttcccc
ccaaaacccaaggacaccctcatgatctcccggacccctgaggtcacatgcgtggtggtggacgtgagccacgaagac

SEQUENCE TABLE 1-continued

Polynucleotide Sequences: FIX-Fc cctgaggtcaagttcaactggtacgtggacggcgtggaggtgcataatgccaagacaaagccgcgggaggagcagtac
aacagcacgtaccgtgtggtcagcgtcctcaccgtcctgcaccaggactggctgaatggcaaggagtacaagtgcaag
gtctccaacaaagccctcccagccccatcgagaaaaccatctccaaagccaaagggcagccccgagaaccacaggtg
tacaccctgcccccatcccgggatgagctgaccaagaaccaggtcagcctgacctgcctggtcaaaggcttctatccc
agcgacatcgccgtggagtgggagagcaatgggcagccggagaacaactacaagaccacgcctcccgtgttggactcc
gacggctccttcttcctctacagcaagctcaccgtggacaagagcaggtggcagcaggggaacgtcttctcatgctcc
gtgatgcatgaggctctgcacaaccactacacgcagaagagcctctccctgtctccgggtaaa D. FIX-Fc Chain DNA Sequence (SEQ ID NO: 13, which encodes SEQ ID NO: 14)
pSYN-FIX-030 Nucleotide sequence (nt 1 to 7583):
FIX exon 1 (signal peptide, 1st amino acid propeptide): nt 690-777
FIX mini intron: nt 778-1076
FIX propeptide sequence: nt 1077-1126
Mature FIX sequence: nt 1127-2371
Fc: nt 2372-3052 gcgcgcgttgacattgattattgactagttattaatagtaatcaattacggggtcattagttcatagcccatatatgg
agttccgcgttacataacttacggtaaatggcccgcctggctgaccgcccaacgaccccgcccattgacgtcaataa
tgacgtatgttcccatagtaacgccaataggggactttccattgacgtcaatgggtggagtatttacggtaaactgccc
acttggcagtacatcaagtgtatcatatgccaagtacgccccctattgacgtcaatgacggtaaatggcccgcctggc
attatgcccagtacatgaccttatgggactttcctacttggcagtacatctacgtattagtcatcgctattaccatgg
tgatgcggttttggcagtacatcaatgggcgtggatagcggtttgactcacggggatttccaagtctccaccccattg
acgtcaatgggagtttgttttggcaccaaaatcaacgggactttccaaaatgtcgtaacaactccgccccattgacgc
aaatgggcggtaggcgtgtacggtgggaggtctatataagcagagctctctggctactagagaacccactgcttact
ggcttatcgaaattaatacgactcactatagggagacccaagcttcgcgacgtacggccgccaccatgcagcgcgtga
catgatcatggcagaatcaccaggcctcatcaccatctgccttttaggatatctactcagtgctgaatgtacaggtt
tgtttccttttttaaaatacattgagtatgcttgcctttagatatagaaatatctgatgctgtcttcttcactaaat
tttgattacatgattttgacagcaatattgaagagtctaacagccagcacgcaggttggtaagtactgtgggaacatca
cagatttggctccatgccctaaagagaaattggctttcagattatttggattaaaaacaaagactttcttaagagat
gtaaattttcatgatgttttcttttttgctaaaactaaagaattattcttttacatttcagttttttcttgatcatga
aaacgccaacaaaattctgaatcggccaaagaggtataattcaggtaaattggaagagtttgttcaaggaatctaga
gagagaatgtatggaagaaaagtgtagttttgaagaagcacgagaagttttgaaaacactgaaagaacaactgaatt
ttggaagcagtatgttgatggagatcagtgtgagtccaatccatgtttaaatggcggcagttgcaaggatgacattaa
ttcctatgaatgttggtgtccctttgattgaaggaaagaaactgtgaattagatgtaacatgtaacattaagaatgg
cagatgcgagcagttttgtaaaaatagtgctgataacaaggtggtttgctcctgtactgagggatatcgacttgcaga
aaaccagaagtcctgtgaaccagcagtgccatttccatgtggaagagtttctgtttcacaaacttctaagctcacccg
tgctgagactgttttcctgatgtggactatgtaaattctactgagctgaaaccattttggataacatcactcaaag
cacccaatcatttaatgacttcactcgggttgttggtggagaagatgccaaaccaggtcaattcccttggcaggttgt
tttgaatggtaaagttgatgcattctgtggaggctctatcgttaatgaaaaatggattgtaactgctgcccactgtgt
tgaaactggtgttaaaattacagttgtcgcaggtgaacataatattgaggagacagaacatacagagcaaaagcgaaa
tgtgattcgaattattcctcaccacaactacaatgcagctattaataagtacaaccatgacattgcccttctggaact
ggacgaacccttagtgctaaacagctacgttacacctatttgcattgctgacaaggaatacacgaacatcttcctcaa
atttggatctggctatgtaagtggctggggaagagtcttccacaaagggagatcagctttagttcttcagtaccttag
agttccacttgttgaccgagccacatgtcttcgatctacaaagttccaccatctataacaacatgttctgtgctggctt
ccatgaaggaggtagagattcatgtcaaggagatagtgggggaccccatgttactgaagtggaagggaccagtttctt
aactggaattattagctggggtgaagagtgtgcaatgaaaggcaaatatggaatatataccaaggtgtcccggtatgt
caactggattaaggaaaaaacaaagctcactgacaaaactcacacatgcccaccgtgcccagctccggaactcctggg
cggaccgtcagtcttcctcttccccccaaaacccaaggacaccctcatgatctcccggacccctgaggtcacatgcgt
ggtggtggacgtgagccacgaagaccctgaggtcaagttcaactggtacgtggacggcgtggaggtgcataatgccaa
gacaaagccgcgggaggagcagtacaacagcacgtaccgtgtggtcagcgtcctcaccgtcctgcaccaggactggct
gaatggcaaggagtacaagtgcaaggtctccaacaaagccctcccagccccatcgagaaaaccatctccaaagccaa
agggcagccccgagaaccacaggtgtacaccctgcccccatcccgggatgagctgaccaagaaccaggtcagcctgac
ctgcctggtcaaaggcttctatcccagcgacatcgccgtggagtgggagagcaatgggcagccggagaacaactacaa
gaccacgcctcccgtgttggactccgacggctccttcttcctctacagcaagctcaccgtggacaagagcaggtggca
gcaggggaacgtcttctcatgctccgtgatgcatgaggctctgcacaaccactacacgcagaagagcctctccctgtc
tccgggtaaatgagaattcagacatgataagatacattgatgagtttggacaaaccacaactagaatgcagtgaaaaa
aatgctttatttgtgaaatttgtgatgctattgctttatttgtaaccattataagctgcaataaacaagttggggtgg
gcgaagaactccagcatgagatccccgctggaggatcatccagccggcgtcccggaaagggattccgaagccccaac
ctttcatagaaggcggcggtggaatcgaaatctcgtagcacgtgtcagtcctgctcctcggccacgaagtgcacgcag
ttgccggccgggtcgcgcagggcgaactcccgcccccacggctgctcgccgatctcggtcatggccggcccggaggcg
tcccggaagttcgtggacacgacctccgaccactcggcgtacagctcgtccaggccgcgcacccacacccaggccagg
gtgttgtccggcaccacctggtcctggaccgcgctgatgaacagggtcacgtcgtccccgaccacacccggcgaagtg
tcctccacgaagtcccgggagaacccgagccggtcggtccagaactcgaccgctccggcgacgtcgcgcgcggtgagc
accggaacggcactggtcaacttggccatggtttagttcctcaccttgtcgtattatactatgccgatatactatgcc
gatgattaattgtcaacacgtgctgatcagatccgaaaatggatatacaagctcccgggagcttttgcaaaagccta
ggcctccaaaaaagcctcctcactacttctggaatagctcagaggcagaggcggcctcggcctctgcataaataaaa
aaattagtcagccatggggcggagaatgggcggaactgggcggagttaggggcgggatgggcggagttaggggcggga
ctatggttgctgactaattgagatgcatgctttgcatacttctgcctgctggggagcctggggactttccacacctgg
ttgctgactaattgagatgcatgctttgcatacttctgcctgctggggagcctgggactttccacaccctcgtcgag
ctagctcgtgaggctccggtgcccgtcagtgggcagagcgcacatcgcccacagtccccgagaagttggggggaggg
gtcggcaattgaaccggtgcctagagaaggtggcgcggggtaaactgggaaagtgatgtcgtgtactggctccgcctt
tttcccgagggtgggggagaaccgtatataagtgcagtagtcgccgtgaacgttctttttcgcaacgggtttgccgcc
agaacacaggtaagtgccgtgtgtggttcccgcgggcctggcctctttacgggttatggccttgcgtgccttgaatt
acttccacctggctccagtacgtgattcttgatcccgagcttcgggttggaagtgggtgggagagttcgaggccttgcgcttaaggagcc
cgcctcgtgcttgagttgaggcctggcctgggcgctggggccgccgcgtgcgaatctggtggcaccttcgcgcctgtc
tcgctgctttcgataagtctctagccatttaaaatttttgatgacctgctgcgacgctttttttctggcaagatagtc
ttgtaaatgcgggccaggatctgcacactggtatttcggtttttggggccgcgggcggcgacggggcccgtgcgtccc
agcgcacatgttcggcgaggcggggcctgcgagcgcggccaccgagaatcggacgggggtagtctcaagctggccggc
ctgctctggtgcctggcctcgcgccgccgtgtatcgccccgccctgggcggcaaggctggcccggtcggcaccagttg

SEQUENCE TABLE 1-continued

Polynucleotide Sequences: FIX-Fc

```
cgtgagcggaaagatggccgcttcccggccctgctccagggggctcaaaatggaggacgcggcgctcgggagagcggg
cgggtgagtcacccacacaaaggaaagggccctttccgtcctcagccgtcgcttcatgtgactccacggagtaccggg
cgccgtccaggcacctcgattagttctggagcttttggagtacgtcgtctttaggttgggggagggggttttatgcga
tggagtttccccacactgagtgggtggagactgaagttaggccagcttggcacttgatgtaattctccttggaatttg
ccctttttgagtttggatcttggttcattctcaagcctcagacagtggttcaaagtttttttcttccatttcaggtgt
cgtgaacacgtggtcgcggccgcgccgccaccatggagacagacacactcctgctatgggtactgctgctctgggttc
caggttccactggtgacaaaactcacacatgccaccgtgcccagcacctgaactcctggaggaccgtcagtcttcc
tcttcccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggagg
agcagtacaacagcacgtaccgtgtggtcagcgtcctcaccgtcctgcaccaggactggctgaatggcaaggagtaca
agtgcaaggtctccaacaaagccctcccagcccccatcgagaaaaccatctccaaagccaaaggggcagccccgagaac
cacaggtgtacaccctgcccccatcccgcgatgagctgaccaagaaccaggtcagcctgacctgcctggtcaaaggct
tctatcccagcgacatcgccgtggagtgggagagcaatgggcagccggagaacaactacaagaccacgcctcccgtgt
tggactccgacggctccttcttcctctacagcaagctcaccgtggacaagagcaggtggcagcaggggaacgtcttct
catgctccgtgatgcatgaggctctgcacaaccactacacgcagaagacctctccctgtctccgggtaaatgactcg
agagatctggccggctgggcccgtttcgaaggtaagcctatccctaaccctctcctcggtctcgattctacgcgtacc
ggtcatcatcaccatcaccattgagtttaaacccgctgatcagcctcgactgtgccttctagttgccagccatctgtt
gtttgcccctcccccgtgccttccttgaccctggaaggtgccactcccactgtcctttcctaataaaatgaggaaatt
gcatcgcattgtctgagtaggtgtcattctattctggggggtggggtggggcaggacacaaggggaggatttggaa
gacaatagcaggcatgctggggatgcggtgggctctatggcttctgaggcggaaagaaccagtggcggtaatacggtt
atccacagaatcaggggataacgcaggaaagaacatgtgagcaaaaggccagcaaaaggccaggaaccgtaaaaaggc
cgcgttgctggcgtttttccataggctccgcccccctgacgagcatcacaaaaatcgacgctcaagtcagaggtggcg
aaacccgacaggactataaagataccaggcgtttccccctggaagctccctcgtgcgctctcctgttccgaccctgcc
gcttaccggatacctgtccgcctttctcccttcgggaagcgtggcgctttctcatagctcacgctgtaggtatctcag
ttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcag
agcgaggtatgtaggcggtgctacagagttcttgaagtggtggcctaactacggctacactagaagaacagtatttgg
tatctgcgctctgctgaagccagttaccttcggaaaaagagttggtagctcttgatccggcaaacaaaccaccgctgg
tagcggtggtttttttgtttgcaagcagcagattacgcgcagaaaaaaaggatctcaagaagatcctttgatcttttc
tacggggtctgacgctcagtggaacgaaaactcacgttaagggattttggtcatgacattaacctataaaaataggcg
tatcacgaggccctttcgtctcgcgcgtttcggtgatgacggtgaaaacctctgacacatgcagctcccggagacggt
cacagcttgtctgtaagcggatgccgggagcagacaagcccgtcagggcgcgtcagcgggtgttggcgggtgtcgggg
ctggcttaactatgcggcatcagagcagattgtactgagagtgcaccatatgcggtgtgaaataccgcacagatgc
gtaaggagaaaataccgcatcaggcgccattcgccattcaggctgcgcaactgttgggaagggcgatcggtgcgggcc
tcttcgctattacgcca
```

E. Fc DNA sequence (mouse Igκ signal peptide underlined) (SEQ ID NO: 3, which encodes SEQ ID NO: 4) This is the Fc cassette from pSYN-FIX-030. In addition, there is a separate Fc expression cassette that was transfected into the cell line in plasmid pSYN-Fc-015 that encodes the same amino acid sequence, but contains a few noncoding changes. The second copy of Fc encoding sequence enables a better monomer: dimer ratio.

<u>atggagacagacacactcctgctatgggtactgctgctctgggttccaggttccactggt</u>gacaaaactcacacatgc
ccaccgtgcccagcacctgaactcctgggaggaccgtcagtcttcctcttccccccaaaacccaaggacaccctcatg
atctcccggacccctgaggtcacatgcgtggtggtggacgtgagccacgaagaccctgaggtcaagttcaactggtac
gtggacggcgtggaggtgcataatgccaagacaaagccgcgggaggagcagtacaacagcacgtaccgtgtggtcagc
gtcctcaccgtcctgcaccaggactggctgaatggcaaggagtacaagtgcaaggtctccaacaaagccctcccagcc
cccatcgagaaaaccatctccaaagccaaagggcagccccgagaaccacaggtgtacaccctgcccccatcccgcgat
gagctgaccaagaaccaggtcagcctgacctgcctggtcaaaggcttctatcccagcgacatcgccgtggagtgggag
agcaatgggcagccggagaacaactacaagaccacgcctcccgtgttggactccgacggctccttcttcctctacagc
aagctcaccgtggacaagagcaggtggcagcaggggaacgtcttctcatgctccgtgatgcatgaggctctgcacaac
cactacacgcagaagagcctctccctgtctccgggtaaa

SEQUENCE TABLE 2

Polypeptide Sequences

A. B-Domain Deleted FVIII-Fc Monomer Hybrid (BDD FVIIIFc monomer dimer): created by coexpressing BDD FVIIIFc and Fc chains.
Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.
A(i). B domain deleted FVIII-Fc chain (19 amino acid signal sequence underlined) (SEQ ID NO: 2)

<u>MQIELSTCFFLCLLRFCFSATRRYYLGAVELSWDYMQSDLGELPVDARFPPRVPKSFPFNTSVVYKKTLFVEFTDHLF
NIAKPRPPWMGLLGPTIQAEVYDTVVITLKNMASHPVSLHAVGVSYWKASEGAEYDDQTSQREKEDDKVFPGGSHTYV
WQVLKENGPMASDPLCLTYSYLSHVDLVKDLNSGLIGALLVCREGSLAKEKTQTLHKFILLFAVFDEGKSWHSETKNS
LMQDRDAASARAWPKMHTVNGYVNRSLPGLIGCHRKSVYWHVIGMGTTPEVHSIFLEGHTFLVRNHRQASLEISPITF
LTAQTLLMDLGQFLLFCHISSHQHDGMEAYVKVDSCPEEPQLRMKNNEEAEDYDDDLTDSEMDVVRFDDDNSPSFIQI
RSVAKKHPKTWVHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVTVEDGPTKSDPR
CLTRYYSSFVNMERDLASGLIGPLLICYKESVDQRGNQIMSDKRNVILFSVFDENRSWYLTENIQRFLPNPAGVQLED
PEFQASNIMHSINGYVFDSLQLSVCLHEVAYWYILSIGAQTDFLSVFFSGYTFKHKMVYEDTLTLFPFSGETVFMSME
NPGLWILGCHNSDFRNRGMTALLKVSSCDKNTGDYYEDSYEDISAYLLSKNNAIEPR</u>*SFSQNPPVLKRHQR*EITRTTL
QSDQEEIDYDDTISVEMKKEDFDIYDEDENQSPRSFQKKTRHYFIAAVERLWDYGMSSSPHVLRNRAQSGSVPQFKKV

SEQUENCE TABLE 2-continued

Polypeptide Sequences

```
VFQEFTDGSFTQPLYRGELNEHLGLLGPYIRAEVEDNIMVTFRNQASRPYSFYSSLISYEEDQRQGAEPRKNFVKPNE
TKTYFWKVQHHMAPTKDEFDCKAWAYFSDVDLEKDVHSGLIGPLLVCHTNTLNPAHGRQVTVQEFALFFTIFDETKSW
YFTENMERNCRAPCNIQMEDPTFKENYRFHAINGYIMDTLPGLVMAQDQRIRWYLLSMGSNENIHSIHFSGHVFTVRK
KEEYKMALYNLYPGVFETVEMLPSKAGIWRVECLIGEHLHAGMSTLFLVYSNKCQTPLGMASGHIRDFQITASGQYGQ
WAPKLARLHYSGSINAWSTKEPFSWIKVDLLAPMIIHGIKTQGARQKFSSLYISQFIIMYSLDGKKWQTYRGNSTGTL
MVFFGNVDSSGIKHNIFNPPIIARYIRLHPTHYSIRSTLRMELMGCDLNSCSMPLGMESKAISDAQITASSYFTNMFA
TWSPSKARLHLQGRSNAWRPQVNNPKEWLQVDFQKTMKVTGVTTQGVKSLLTSMYVKEFLISSSQDGHQWTLFFQNGK
VKVFQGNQDSFTPVVNSLDPPLLTRYLRIHPQSWVHQIALRMEVLGCEAQDLYDKTHTCPPCPAPELLGGPSVFLFPP
KPKDTLMISRTPEVTCVVVDVSHEDPEVKFNWYVDGVEVHNAKTKPREEQYNSTYRVVSVLTVLHQDWLNGKEYKCKV
SNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK
```

A(ii). Fc chain (20 amino acid heterologous signal peptide from mouse Igκ chain underlined) (SEQ ID NO: 4)
```
METDTLLLWVLLLWVPGSTGDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPGK
```

B. Full length FVIIIFc monomer hybrid (Full length FVIIIFc monomer dimer): created by coexpressing FVIIIFc and Fc chains.
Construct = HC-B-LC-Fc fusion. An Fc expression cassette is cotransfected with full length FVIII-Fcto generate the full length FVIIIFc monomer. For the FVIIIFc chain, the Fc sequence is shown in bold; HC sequence is shown in double underline; B domain sequence is shown in italics. Signal peptides are underlined.
B(i). Full length FVIIIFc chain (FVIII signal peptide underlined (SEQ ID NO: 6)
```
MQIELSTCFFLCLLRFCFSATRRYYLGAVELSWDYMQSDLGELPVDARFPPRVPKSPPFNTSVVYKKTLFVEFTDHLF
NIAKPRPPWMGLLGPTIQAEVYDTVVITLKNMASHPVSLHAVGVSYWKASEGAEYDDQTSQREKEDDKVFPGGSHTYV
WQVLKENGPMASDPLCLTYSYLSHVDLVKDLNSGLIGALLVCREGSLAKEKTQTLHKFILLFAVFDEGKSWHSETKNS
LMQDRDAASARAWPKMHTVNGYVNRSLPGLIGCHRKSVYWHVIGMGTTPEVHSIFLEGHTFLVRNHRQASLEISPITF
LTAQTLLMDLGQFLLFCHISSSHQHDGMEAYVKVDSCPEEPQLRMKNNEEAEDYDDDLTDSEMDVVRFDDDNSPSFIQI
RSVAKKHPKTWVHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVTVEDGPTKSDPR
CLTRYYSSFVNMERDLASGLIGPLLICYKESVDQRGNQIMSDKRNVILFSVFDENRSWYLTENIQRFLPNPAGVQLED
PEFQASNIMHSINGYVFDSLQLSVCLHEVAYWYILSIGAQTDFLSVFFSGYTFKHKMVYEDTLTLFPFSGETVFMSME
NPGLWILGCHNSDFRNRGMTALLKVSSCDKNTGDYYEDSYEDISAYLLSKNNAIEPRSFSQNSRHPSTRQKQFNATTI
PENDIEKTDPWFAHRTPMPKIQNVSSSDLLMLLRQSPTPHGLSLSDLQEAKYETFSDDPSPGAIDSNNSLSEMTHFRP
QLHHSGDMVFTPESGLQLRLNEKLGTTAATELKKLDFKVSSTSNNLISTIPSDNLAAGTDNTSSLGPPSMPVHYDSQL
DTTLFGKKSSPLTESGGPLSLSEENNDSKLLESGLMNSQESSWGKNVSSTESGRLFKGKRAHGPALLTKDNALFKVSI
SLLKTNKTSNNSATNRKTHIDGPSLLIENSPSVWQNILESDTEFKKVTPLIHDRMLMDKNATALRLNHMSNKTTSSKN
MEMVQQKKEGPIPPDAQNPDMSFFKMLFLPESARWIQRTHGKNSLNSGQGPSPKQLVSLGPEKSVEGQNFLSEKNKVV
VGKGEFTKDVGLKEMVFPSSRNLFLTNLDNLHENNTHNQEKKIQEEIEKKETLIQENVVLPQIHTVTGTKNFMKNLFL
LSTRQNVEGSYDGAYAPVLQDFRSLNDSTNRTKKHTAHFSKKGEEENLEGLGNQTKQIVEKYACTTRISPNTSQQNFV
TQRSKRALKQFRLPLEETELEKRIIVDDTSTQWSKNMKHLTPSTLTQIDYNEKEKGAITQSPLSDCLTRSHSIPQANR
SPLPIAKVSSFPSIRPIYLTRVLFQDNSSHLPAASYRKKDSGVQESSHFLQGAKKNNLSLAILTLEMTGDQREVGSLG
TSATNSVTYKKVENTVLPKPDLPKTSGKVELLPKVHIYQKDLFPTETSNGSPGHLDLVEGSLLQGTEGAIKWNEANRP
GKVPFLRVATESSAKTPSKLLDPLAWDNHYGTQIPKEEWKSQEKSPEKTAFKKKDTILSLNACESNHAIAAINEGQNK
PEIEVTWAKQGRTERLCSQNPPVLKRHQREITRTTLQSDQEEIDYDDTISVEMKKEDFDIYDEDENQSPRSFQKKTRH
YFIAAVERLWDYGMSSSPHVLRNRAQSGSVPQFKKVVFQEFTDGSFTQPLYRGELNEHLGLLGPYIRAEVEDNIMVTF
RNQASRPYSFYSSLISYEEDQRQGAEPRKNFVKPNETKTYFWKVQHHMAPTKDEFDCKAWAYFSDVDLEKDVHSGLIG
PLLVCHTNTLNPAHGRQVTVQEFALFFTIFDETKSWYFTENMERNCRAPCNIQMEDPTFKENYRFHAINGYIMDTLPG
LVMAQDQRIRWYLLSMGSNENIHSIHFSGHVFTVRKKEEYKMALYNLYPGVFETVEMLPSKAGIWRVECLIGEHLHAG
MSTLFLVYSNKCQTPLGMASGHIRDFQITASGQYGQWAPKLARLHYSGSINAWSTKEPFSWIKVDLLAPMIIHGIKTQ
GARQKFSSLYISQFIIMYSLDGKKWQTYRGNSTGTLMVFFGNVDSSGIKHNIFNPPIIARYIRLHPTHYSIRSTLRME
LMGCDLNSCSMPLGMESKAISDAQITASSYFTNMFATWSPSKARLHLQGRSNAWRPQVNNPKEWLQVDFQKTMKVTGV
TTQGVKSLLTSMYVKEFLISSSQDGHQWTLFFQNGKVKVFQGNQDSFTPVVNSLDPPLLTRYLRIHPQSWVHQIALRM
EVLGCEAQDLYDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSVMHEALHNHYTQKSLSL
SPGK
```

B(ii). Fc chain (20 amino acid heterologous signal peptide from mouse Igκ chain underlined) (SEQ ID NO: 4)
```
METDTLLLWVLLLWVPGSTGDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKAKGQPREPQVYTLPPSRD
ELTKNQVSLTCLVKGFYPSDIAVEWESNGQPENNYKTTPPVLDSDGSFFLYSKLTVDKSRWQQGNVFSCSVMHEALHN
HYTQKSLSLSPGK
```

C. FVIII-Fc Heterodimer Hybrid
This is made by cotransfecting HC-Fc and LC-Fc constructs. Two HC-Fc constructs have been made. One has no linker between HC and Fc (HC-Fc) while the other has a 5 amino acid linker between HC and Fc (HC+5-Fc). The FVIII signal peptide was used for the HC-Fc constructs, while the mouse Igκ signal sequence was used for the LC-Fc construct.
C(i). HC-Fc (Fc sequence is shown in bold, signal peptide underlined) (SEQ ID NO: 8)
```
MQIELSTCFFLCLLRFCFSATRRYYLGAVELSWDYMQSDLGELPVDARFPPRVPKSPPFNTSVVYKKTLFVEFTDHLF
NIAKPRPPWMGLLGPTIQAEVYDTVVITLKNMASHPVSLHAVGVSYWKASEGAEYDDQTSQREKEDDKVFPGGSHTYV
WQVLKENGPMASDPLCLTYSYLSHVDLVKDLNSGLIGALLVCREGSLAKEKTQTLHKFILLFAVFDEGKSWHSETKNS
LMQDRDAASARAWPKMHTVNGYVNRSLPGLIGCHRKSVYWHVIGMGTTPEVHSIFLEGHTFLVRNHRQASLEISPITF
```

SEQUENCE TABLE 2-continued

Polypeptide Sequences

LTAQTLLMDLGQFLLFCHISSHQHDGMEAYVKVDSCPEEPQLRMKNNEEAEDYDDDLTDSEMDVVRFDDDNSPSFIQI
RSVAKKHPKTWVHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVTVEDGPTKSDPR
CLTRYYSSFVNMERDLASGLIGPLLICYKESVDQRGNQIMSDKRNVILFSVFDENRSWYLTENIQRFLPNPAGVQLED
PEFQASNIMHSINGYVFDSLQLSVCLHEVAYWYILSIGAQTDFLSVFFSGYTFKHKMVYEDTLTLFPFSGETVFMSME
NPGLWILGCHNSDFRNRGMTALLKVSSCDKNTGDYYEDSYEDISAYLLSKNNAIEPRDKTHTCPPCPAPELLGGPSVF
LFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK

C(ii). HC+5-Fc (Fc sequence is shown in bold, 5 amino acid linker sequence(from the
B domain of FVIII) is shown in italics (boxed), signal peptide underlined.) (SEQ ID NO: 10)
<u>MQIELSTCFFLCLLRFCFS</u>ATRRYYLGAVELSWDYMQSDLGELPVDARFPPRVPKSFPFNTSVVYKKTLFVEFTDHLF
NIAKPRPPWMGLLGPTIQAEVYDTVVITLKNMASHPVSLHAVGVSYWKASEGAEYDDQTSQREKEDDKVFPGGSHTYV
WQVLKENGPMASDPLCLTYSYLSHVDLVKDLNSGLIGALLVCREGSLAKEKTQTLHKFILLFAVFDEGKSWHSETKNS
LMQDRDAASARAWPKMHTVNGYVNRSLPGLIGCHRKSVYWHVIGMGTTPEVHSIFLEGHTFLVRNHRQASLEISPITF
LTAQTLLMDLGQFLLFCHISSHQHDGMEAYVKVDSCPEEPQLRMKNNEEAEDYDDDLTDSEMDVVRFDDDNSPSFIQI
RSVAKKHPKTWVHYIAAEEEDWDYAPLVLAPDDRSYKSQYLNNGPQRIGRKYKKVRFMAYTDETFKTREAIQHESGIL
GPLLYGEVGDTLLIIFKNQASRPYNIYPHGITDVRPLYSRRLPKGVKHLKDFPILPGEIFKYKWTVTVEDGPTKSDPR
CLTRYYSSFVNMERDLASGLIGPLLICYKESVDQRGNQIMSDKRNVILFSVFDENRSWYLTENIQRFLPNPAGVQLED
PEFQASNIMHSINGYVFDSLQLSVCLHEVAYWYILSIGAQTDFLSVFFSGYTFKHKMVYEDTLTLFPFSGETVFMSME
NPGLWILGCHNSDFRNRGMTALLKVSSCDKNTGDYYEDSYEDISAYLLSKNNAIEPR*SFSQN* DKTHTCPPCPAPELLG
GPSVFLFPPKPKDTLMISRTPEVTCVVVDVSHEDPEVKFNWYVDGVEVHNAKTKPREEQYNSTYRVVSVLTVLHQDWL
NGKEYKCKVSNKALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK

C(iii). LC-Fc6His (Fc sequence is shown in bold, signal peptide underlined.)
(SEQ ID NO: 12)
<u>METDTLLLWVLLLWVPGSTG</u>EITRTTLQSDQEEIDYDDTISVEMKKEDFDIYDEDENQSPRSFQKKTRHYFIAAVERL
WDYGMSSSPHVLRNRAQSGSVPQFKKVVFQEFTDGSFTQPLYRGELNEHLGLLGPYIRAEVEDNIMVTFRNQASRPYS
FYSSLISYEEDQRQGAEPRKNFVKPNETKTYFWKVQHHMAPTKDEFDCKAWAYFSDVDLEKDVHSGLIGPLLVCHTNT
LNPAHGRQVTVQEFALFFTIFDETKSWYFTENMERNCRAPCNIQMEDPTFKENYRFHAINGYIMDTLPGLVMAQDQRI
RWYLLSMGSNENIHSIHFGHVFTVRKKEEYKMALYNLYPGVFETVEMLPSKAGIWRVECLIGEHLHAGMSTLFLVYS
NKCQTPLGMASGHIRDFQITASGQYGQWAPKLARLHYSGSINAWSTKEPFSWIKVDLLAPMIIHGIKTQGARQKFSSL
YISQFIIMYSLDGKKWQTYRGNSTGTLMVFFGNVDSSGIKHNIFNPPIIARYIRLHPTHYSIRSTLRMELMGCDLNSC
SMPLGMESKAISDAQITASSYFTNMFATWSPSKARLHLQGRSNAWRPQVNNPKEWLQNPFTMKVTGVTTQGVKSLL
TSMYVKEFLISSSQDGHQWTLFFQNGKVKVFQGNQDSFTPVVNSLDPPLLTRYLRIHPQSWVHQIALRMEVLGCEAQD
LYDKTHTCPPCPAPELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVMHEALHNHYTQKSLSLSPGK

D. FIX-Fc chain (SEQ ID NO: 14):
(28 amino acid signal sequence underlined, 18 amino acid propeptide double underlined, Fc
portion in italics.) The C-terminal lysine is not present in either subunit; this
processing is often observed in recombinant proteins produced in mammalian cell culture, as
well as with plasma derived proteins.

E. FIXFc-SC subunit:
FIX SignalPeptide:
-46 MQRVNMIMAESPGLITICLLGYLLSAEC

FIXPropeptide: -18 TVFLDHENAN KILNRPKR
YNSGKLEEFVQGNLERECMEEKCSFEEAREVFENTERTTEFWKQYVDGDQCESNPCLNGGSCKDDINSYECWCPFGFE
GKNCELDVTCNIKNGRCEQFCKNSADNKVVCSCTEGYRLAENQKSCEPAVPFPCGRVSVSQTSKLTRAETVFPDVDYV
NSTEAETILDNITQSTQSFNDFTRVVGGEDAKPGQFPWQVVLNGKVDAFCGGSIVNEKWIVTAAHCVETGVKITVVAG
EHNIEETEHTEQKRNVIRIIPHHNYNAAINKYNHDIALLELDEPLVLNSYVTPICIADKEYTNIFLKFGSGYVSGWGR
VFHKGRSALVLQYLRVPLVDRATCLRSTKFTIYNNMFCAGFHEGGRDSCQGDSGGPHVTEVEGTSFLTGIISWGEECA
MKGKYGIYTKVSRYVNWIKEKTKLT*DKTHTCPPCPAPELLGGPSVFLFPPKPKDTLMISRTPEVTCVVVDVSHEDPEV*
*KFNWYVDGVEVHNAKTKPREEQYNSTYRVVSVLTVLHQDWLNGKEYKCKVSNKALPAPIEKTISKAKGQPREPQVYTL*
*PPSRDELTKNQVSLTCLVKGFYPSDIAVEWESNGQPENNYKTTPPVLDSDGSFFLYSKLTVDKSRWQQGNVFSCSVMH*
*EALHNHYTQKSLSLSPGK*

Mature Fc sequence (corresponding to human IgG1 amino acids 221 to 447, EU numbering)
DKTHTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHYTQKSLSLSPGK

What is claimed is:

1. A method of modifying a hemophilia B treatment in a subject who has hemophilia B, comprising:
   (a) measuring the time between
      (i) contacting of a sample obtained from the subject with an activation mixture consisting essentially of an activated Factor XI (FXIa) and a phospholipid mixture, and
      (ii) onset of clotting, thereby calculating a clotting time (Ct);
   wherein the Ct is used to determine a pharmacokinetic (PK) parameter of Factor IX,
   wherein the PK parameter is terminal half-life (HL) or time to trough (T),
   wherein HL is calculated according to the formula:

$$HL = -0.693 \times (T_2 - T_1) \times A / (Ct_1 - Ct_2)$$ [Formula II]

and wherein T is calculated according to the formula:

$$T = -1.44 \times HL / (A \times (Ct_{measured} - Ct_{trough}))$$ [Formula III]

wherein, for Factor IX, A is a constant value corresponding to the slope of a Ct versus Factor IX concentration dose-response, $T_1$ and $T_2$ are times at which Ct is measured, and $Ct_1$ and $Ct_2$ are Ct values measured at $T_1$ and $T_2$, respectively, $Ct_{measured}$ is Ct measured at certain time point, and $Ct_{trough}$ is patient-specific clotting time at trough; and
   (b) modifying the hemophilia B treatment for the subject based on the PK parameter, wherein the PK parameter correlates with a therapeutically efficacious treatment, thereby administering an optimized hemophilia B treatment to the subject, wherein the treatment is adjusted;
   wherein the measurement is carried out in a point of care test system, and
   wherein the phospholipid mixture comprises 75 mole-% of phosphatidylcholine, 20 mole-% of phosphatidylserine, and 5 mole-% of phosphatidylglycerol.

2. The method of claim 1, wherein the sample is selected from the group consisting of whole blood, citrated or equivalently stabilized blood, plasma, and other fluid sample containing or suspected of containing Factor IX.

3. The method of claim 1, wherein the sample is decalcified.

4. The method of claim 1, wherein the subject has received prior Factor IX treatment, but the treatment has been discontinued for a time period sufficient to deplete the Factor IX from the subject's blood.

5. The method of claim 1, wherein the Factor IX is rFIXFc.

6. The method of claim 1, wherein the activation mixture consists essentially of 80% of Factor XIa suspension and 20% of the phospholipid mixture.

7. The method of claim 6, wherein the activation mixture is dried onto a solid substrate.

8. The method of claim 1, wherein the activation mixture does not contain an additional coagulation factor activator or inhibitor.

9. A method of modifying a hemophilia B treatment in a subject who has hemophilia B, comprising:
   (a) measuring the time between
      (i) contacting of a sample obtained from the subject with an activation mixture consisting essentially of 80% of activated Factor XI (FXIa) and 20% of a phospholipid mixture comprising 75 mole-% of phosphatidylcholine, 20 mole-% of phosphatidylserine, and 5 mole-% of phosphatidylglycerol, and
      (ii) onset of clotting, thereby calculating a clotting time (Ct);
   wherein the Ct is used to determine a pharmacokinetic (PK) parameter of Factor IX,
   wherein the PK parameter is terminal half-life (HL) or time to trough (T),
   wherein HL is calculated according to the formula:

$$HL = -0.693 \times (T_2 - T_1) \times A / (Ct_1 - Ct_2)$$ [Formula II]

and wherein T is calculated according to the formula:

$$T = -1.44 \times HL / (A \times (Ct_{measured} - Ct_{trough}))$$ [Formula III]

wherein, for Factor IX, A is a constant value corresponding to the slope of a Ct versus Factor IX concentration dose-response, $T_1$ and $T_2$ are times at which Ct is measured, and $Ct_1$ and $Ct_2$ are Ct values measured at $T_1$ and $T_2$, respectively, $Ct_{measured}$ is Ct measured at certain time point, and $Ct_{trough}$ is patient-specific clotting time at trough; and (b) modifying the hemophilia B treatment for the subject based on the PK parameter, wherein the PK parameter correlates with a therapeutically efficacious treatment, thereby administering an optimized hemophilia B treatment to the subject, wherein the treatment is adjusted;

wherein the measurement is carried out in a point of care test system, and wherein the Factor IX is rFIXFc, wherein the activation mixture is dried onto a solid substrate, and wherein the activation mixture does not contain an additional coagulation factor activator or inhibitor.

* * * * *

SEQUENCE LISTING

<160> NUMBER OF SEQ ID NOS: 14

<210> SEQ ID NO 1
<211> LENGTH: 5052

```
<212> TYPE: DNA
<213> ORGANISM: Artificial Sequence
<220> FEATURE:
<223> OTHER INFORMATION: B-Domain Deleted FVIIIFc Chain
<220> FEATURE:
<221> NAME/KEY: sig_peptide
<222> LOCATION: (1)..(57)
<220> FEATURE:
<221> NAME/KEY: misc_feature
<222> LOCATION: (4371)..(5052)
<223> OTHER INFORMATION: Fc region

<400> SEQUENCE: 1
```

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | aagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggataggggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agttctctact | gttttgtcat | atctcttccc | accaacatga | tggcatggaa | 1020 |
| gcttatgtca | aagtagacag | ctgtccagag | gaaccccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctcccct | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | ggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaacatttt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |

```
attggagcac agactgactt cctttctgtc ttcttctctg gatatacctt caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctctcaaa acccaccagt cttgaaacgc atcaacggg aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag ccottatacc gtggagaact aaatgaacat    2640
ttgggactcc tggggccata tataagagca gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctggaaaaa gatgtgcact caggcctgat tggacccctt    2940
ctggtctgcc acactaacac actgaaccct gctcatggga gacaagtgac agtacaggaa    3000
tttgctctgt tttcaccat ctttgatgag accaaaagct ggtacttcac tgaaaatatg    3060
gaaagaaact gcagggctcc ctgcaatatc cagatggaag atcccacttt taagagaat    3120 tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac acttttctg    3420 gtgtacagca ataagtgtca gactcccctg ggaatggctt ctggacacat tagagatttt    3480
cagattacag cttcaggaca atatggacag tgggcccaa agctggccag acttcattat    3540
tccggatcaa tcaatgcctg gagcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg ggaagaagtg gcagacttat    3720
cgaggaaatt ccactggaac cttaatggtc ttctttggca atgtggattc atctgggata    3780
aaacacaata ttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagacctca ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctcttttt    4200 cagaatggca aagtaaaggt ttttcaggga aatcaagact ccttcacacc tgtggtgaac    4260
tctctagacc caccgttact gactcgctac cttcgaattc accccagag ttgggtgcac    4320
```

```
cagattgccc tgaggatgga ggttctgggc tgcgaggcac aggacctcta cgacaaaact    4380
cacacatgcc accgtgccc agctccagaa ctcctgggcg gaccgtcagt cttcctcttc     4440
cccccaaaac ccaaggacac cctcatgatc tcccggaccc ctgaggtcac atgcgtggtg    4500
gtggacgtga gccacgaaga ccctgaggtc aagttcaact ggtacgtgga cggcgtggag    4560
gtgcataatg ccaagacaaa gccgcgggag gagcagtaca acagcacgta ccgtgtggtc    4620
agcgtcctca ccgtcctgca ccaggactgg ctgaatggca aggagtacaa gtgcaaggtc    4680
tccaacaaag ccctcccagc ccccatcgag aaaaccatct ccaaagccaa agggcagccc    4740
cgagaaccac aggtgtacac cctgccccca tcccgggatg agctgaccaa gaaccaggtc    4800
agcctgacct gcctggtcaa aggcttctat cccagcgaca tcgccgtgga gtgggagagc    4860
aatgggcagc cggagaacaa ctacaagacc acgcctcccg tgttggactc cgacggctcc    4920
ttcttcctct acagcaagct caccgtggac aagagcaggt ggcagcaggg gaacgtcttc    4980
tcatgctccg tgatgcatga ggctctgcac aaccactaca cgcagaagag cctctccctg    5040
tctccgggta aa                                                        5052

<210> SEQ ID NO 2
<211> LENGTH: 1684
<212> TYPE: PRT
<213> ORGANISM: Artificial Sequence
<220> FEATURE:
<223> OTHER INFORMATION: B-Domain Deleted FVIIIFc Chain
<220> FEATURE:
<221> NAME/KEY: SIGNAL
<222> LOCATION: (1)..(19)
<220> FEATURE:
<221> NAME/KEY: MISC_FEATURE
<222> LOCATION: (1457)..(1684)
<223> OTHER INFORMATION: Fc region

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190
```

```
Gly Ala Leu Leu Val Cys Arg Glu Gly Ser Leu Ala Lys Glu Lys Thr
            195                 200                 205
Gln Thr Leu His Lys Phe Ile Leu Leu Phe Ala Val Phe Asp Glu Gly
        210                 215                 220
Lys Ser Trp His Ser Glu Thr Lys Asn Ser Leu Met Gln Asp Arg Asp
225                 230                 235                 240
Ala Ala Ser Ala Arg Ala Trp Pro Lys Met His Thr Val Asn Gly Tyr
                245                 250                 255
Val Asn Arg Ser Leu Pro Gly Leu Ile Gly Cys His Arg Lys Ser Val
            260                 265                 270
Tyr Trp His Val Ile Gly Met Gly Thr Thr Pro Glu Val His Ser Ile
        275                 280                 285
Phe Leu Glu Gly His Thr Phe Leu Val Arg Asn His Arg Gln Ala Ser
    290                 295                 300
Leu Glu Ile Ser Pro Ile Thr Phe Leu Thr Ala Gln Thr Leu Leu Met
305                 310                 315                 320
Asp Leu Gly Gln Phe Leu Leu Phe Cys His Ile Ser Ser His Gln His
                325                 330                 335
Asp Gly Met Glu Ala Tyr Val Lys Val Asp Ser Cys Pro Glu Glu Pro
            340                 345                 350
Gln Leu Arg Met Lys Asn Asn Glu Glu Ala Glu Asp Tyr Asp Asp Asp
        355                 360                 365
Leu Thr Asp Ser Glu Met Asp Val Val Arg Phe Asp Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
```

```
            610                 615                 620
Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Pro Pro Val Leu
                755                 760                 765

Lys Arg His Gln Arg Glu Ile Thr Arg Thr Thr Leu Gln Ser Asp Gln
770                 775                 780

Glu Glu Ile Asp Tyr Asp Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                805                 810                 815

Gln Lys Lys Thr Arg His Tyr Phe Ile Ala Ala Val Glu Arg Leu Trp
                820                 825                 830

Asp Tyr Gly Met Ser Ser Ser Pro His Val Leu Arg Asn Arg Ala Gln
                835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
                915                 920                 925

Lys Asn Phe Val Lys Pro Asn Glu Thr Lys Thr Tyr Phe Trp Lys Val
930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
                995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035
```

Glu Asn Tyr Arg Phe His Ala Ile Asn Gly Tyr Ile Met Asp Thr
    1040            1045            1050

Leu Pro Gly Leu Val Met Ala Gln Asp Gln Arg Ile Arg Trp Tyr
    1055            1060            1065

Leu Leu Ser Met Gly Ser Asn Glu Asn Ile His Ser Ile His Phe
    1070            1075            1080

Ser Gly His Val Phe Thr Val Arg Lys Lys Glu Glu Tyr Lys Met
    1085            1090            1095

Ala Leu Tyr Asn Leu Tyr Pro Gly Val Phe Glu Thr Val Glu Met
    1100            1105            1110

Leu Pro Ser Lys Ala Gly Ile Trp Arg Val Glu Cys Leu Ile Gly
    1115            1120            1125

Glu His Leu His Ala Gly Met Ser Thr Leu Phe Leu Val Tyr Ser
    1130            1135            1140

Asn Lys Cys Gln Thr Pro Leu Gly Met Ala Ser Gly His Ile Arg
    1145            1150            1155

Asp Phe Gln Ile Thr Ala Ser Gly Gln Tyr Gly Gln Trp Ala Pro
    1160            1165            1170

Lys Leu Ala Arg Leu His Tyr Ser Gly Ser Ile Asn Ala Trp Ser
    1175            1180            1185

Thr Lys Glu Pro Phe Ser Trp Ile Lys Val Asp Leu Leu Ala Pro
    1190            1195            1200

Met Ile Ile His Gly Ile Lys Thr Gln Gly Ala Arg Gln Lys Phe
    1205            1210            1215

Ser Ser Leu Tyr Ile Ser Gln Phe Ile Ile Met Tyr Ser Leu Asp
    1220            1225            1230

Gly Lys Lys Trp Gln Thr Tyr Arg Gly Asn Ser Thr Gly Thr Leu
    1235            1240            1245

Met Val Phe Phe Gly Asn Val Asp Ser Ser Gly Ile Lys His Asn
    1250            1255            1260

Ile Phe Asn Pro Pro Ile Ile Ala Arg Tyr Ile Arg Leu His Pro
    1265            1270            1275

Thr His Tyr Ser Ile Arg Ser Thr Leu Arg Met Glu Leu Met Gly
    1280            1285            1290

Cys Asp Leu Asn Ser Cys Ser Met Pro Leu Gly Met Glu Ser Lys
    1295            1300            1305

Ala Ile Ser Asp Ala Gln Ile Thr Ala Ser Ser Tyr Phe Thr Asn
    1310            1315            1320

Met Phe Ala Thr Trp Ser Pro Ser Lys Ala Arg Leu His Leu Gln
    1325            1330            1335

Gly Arg Ser Asn Ala Trp Arg Pro Gln Val Asn Asn Pro Lys Glu
    1340            1345            1350

Trp Leu Gln Val Asp Phe Gln Lys Thr Met Lys Val Thr Gly Val
    1355            1360            1365

Thr Thr Gln Gly Val Lys Ser Leu Leu Thr Ser Met Tyr Val Lys
    1370            1375            1380

Glu Phe Leu Ile Ser Ser Ser Gln Asp Gly His Gln Trp Thr Leu
    1385            1390            1395

Phe Phe Gln Asn Gly Lys Val Lys Val Phe Gln Gly Asn Gln Asp
    1400            1405            1410

Ser Phe Thr Pro Val Val Asn Ser Leu Asp Pro Pro Leu Leu Thr
    1415            1420            1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr Asp
1445                1450                1455

Lys Thr His Thr Cys Pro Pro Cys Pro Ala Pro Glu Leu Leu Gly
1460                1465                1470

Gly Pro Ser Val Phe Leu Phe Pro Pro Lys Pro Lys Asp Thr Leu
1475                1480                1485

Met Ile Ser Arg Thr Pro Glu Val Thr Cys Val Val Val Asp Val
1490                1495                1500

Ser His Glu Asp Pro Glu Val Lys Phe Asn Trp Tyr Val Asp Gly
1505                1510                1515

Val Glu Val His Asn Ala Lys Thr Lys Pro Arg Glu Glu Gln Tyr
1520                1525                1530

Asn Ser Thr Tyr Arg Val Val Ser Val Leu Thr Val Leu His Gln
1535                1540                1545

Asp Trp Leu Asn Gly Lys Glu Tyr Lys Cys Lys Val Ser Asn Lys
1550                1555                1560

Ala Leu Pro Ala Pro Ile Glu Lys Thr Ile Ser Lys Ala Lys Gly
1565                1570                1575

Gln Pro Arg Glu Pro Gln Val Tyr Thr Leu Pro Pro Ser Arg Asp
1580                1585                1590

Glu Leu Thr Lys Asn Gln Val Ser Leu Thr Cys Leu Val Lys Gly
1595                1600                1605

Phe Tyr Pro Ser Asp Ile Ala Val Glu Trp Glu Ser Asn Gly Gln
1610                1615                1620

Pro Glu Asn Asn Tyr Lys Thr Thr Pro Pro Val Leu Asp Ser Asp
1625                1630                1635

Gly Ser Phe Phe Leu Tyr Ser Lys Leu Thr Val Asp Lys Ser Arg
1640                1645                1650

Trp Gln Gln Gly Asn Val Phe Ser Cys Ser Val Met His Glu Ala
1655                1660                1665

Leu His Asn His Tyr Thr Gln Lys Ser Leu Ser Leu Ser Pro Gly
1670                1675                1680

Lys

<210> SEQ ID NO 3
<211> LENGTH: 762
<212> TYPE: DNA
<213> ORGANISM: Artificial Sequence
<220> FEATURE:
<223> OTHER INFORMATION: Fc sequence
<220> FEATURE:
<221> NAME/KEY: sig_peptide
<222> LOCATION: (1)..(30)
<223> OTHER INFORMATION: Ig-Kappa signal peptide

<400> SEQUENCE: 3
atggagacag acacactcct gctatgggta ctgctgctct gggttccagg ttccactggt      60
gacaaaactc acatgcccc accgtgccca gcacctgaac tcctgggagg accgtcagtc     120
ttcctcttcc cccaaaaacc caaggacacc ctcatgatct cccggacccc tgaggtcaca     180
tgcgtggtgg tggacgtgag ccacgaagac cctgaggtca agttcaactg gtacgtggac     240
ggcgtggagg tgcataatgc caagacaaag ccgcgggagg agcagtacaa cagcacgtac     300
cgtgtggtca gcgtcctcac cgtcctgcac caggactggc tgaatggcaa ggagtacaag     360

```
tgcaaggtct ccaacaaagc cctcccagcc cccatcgaga aaaccatctc caaagccaaa        420
gggcagcccc gagaaccaca ggtgtacacc ctgcccccat cccgcgatga gctgaccaag        480
aaccaggtca gcctgacctg cctggtcaaa ggcttctatc ccagcgacat cgccgtggag        540
tgggagagca tgggcagcc ggagaacaac tacaagacca cgcctcccgt gttggactcc         600
gacggctcct tcttcctcta cagcaagctc accgtggaca agagcaggtg gcagcagggg        660
aacgtcttct catgctccgt gatgcatgag gctctgcaca accactacac gcagaagagc        720
ctctccctgt ctccgggtaa actctccctg tctccgggta aa                          762
```

<210> SEQ ID NO 4
<211> LENGTH: 247
<212> TYPE: PRT
<213> ORGANISM: Artificial Sequence
<220> FEATURE:
<223> OTHER INFORMATION: Fc sequence
<220> FEATURE:
<221> NAME/KEY: SIGNAL
<222> LOCATION: (1)..(10)
<223> OTHER INFORMATION: Ig-Kappa signal peptide

<400> SEQUENCE: 4

```
Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val
50                  55                  60

Asp Val Ser His Glu Asp Pro Glu Val Lys Phe Asn Trp Tyr Val Asp
65                  70                  75                  80

Gly Val Glu Val His Asn Ala Lys Thr Lys Pro Arg Glu Glu Gln Tyr
                85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
        210                 215                 220

Cys Ser Val Met His Glu Ala Leu His Asn His Tyr Thr Gln Lys Ser
225                 230                 235                 240

Leu Ser Leu Ser Pro Gly Lys
                245
```

<210> SEQ ID NO 5
<211> LENGTH: 7674

```
<212> TYPE: DNA
<213> ORGANISM: Artificial Sequence
<220> FEATURE:
<223> OTHER INFORMATION: Full Length FVIIIFc
<220> FEATURE:
<221> NAME/KEY: sig_peptide
<222> LOCATION: (1)..(57)
<220> FEATURE:
<221> NAME/KEY: misc_feature
<222> LOCATION: (6993)..(7674)
<223> OTHER INFORMATION: Fc Region

<400> SEQUENCE: 5
```

| | | | | | |
|---|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaaagactt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggatagggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaacccccaa | ctacgaatga | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | ccctcagcgg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | ttactttatg | ggaagttgg | agacacactg | 1440 |
| ttgattatat | ttaagaatca | agcaagcaga | ccatataaca | tctaccctca | cggaatcact | 1500 |
| gatgtccgtc | ctttgtattc | aaggagatta | ccaaaaggtg | taaaacattt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccattgtttg | catgaggtgg | catactggta | cattctaagc | 1920 |
| attggagcac | agactgactt | cctttctgtc | ttcttctctg | gatataccct | caaacacaaa | 1980 |

```
atggtctatg aagacacact caccctattc ccattctcag gagaaactgt cttcatgtcg    2040
atggaaaacc caggtctatg gattctgggg tgccacaact cagactttcg gaacagaggc    2100
atgaccgcct tactgaaggt ttctagttgt gacaagaaca ctggtgatta ttacgaggac    2160
agttatgaag atatttcagc atacttgctg agtaaaaaca atgccattga accaagaagc    2220
ttctcccaga attcaagaca ccctagcact aggcaaaagc aatttaatgc caccacaatt    2280
ccagaaaatg acatagagaa gactgaccct tggtttgcac acagaacacc tatgcctaaa    2340
atacaaaatg tctcctctag tgatttgttg atgctcttgc gacagagtcc tactccacat    2400
gggctatcct tatctgatct ccaagaagcc aaatatgaga ctttttctga tgatccatca    2460
cctggagcaa tagacagtaa taacagcctg tctgaaatga cacacttcag gccacagctc    2520
catcacagtg gggacatggt atttacccct gagtcaggcc tccaattaag attaaatgag    2580
aaactgggga caactgcagc aacagagttg aagaaacttg atttcaaagt ttctagtaca    2640
tcaaataatc tgatttcaac aattccatca gacaatttgg cagcaggtac tgataataca    2700
agttccttag acccccaag tatgccagtt cattatgata gtcaattaga taccactcta    2760
tttggcaaaa agtcatctcc ccttactgag tctggtggac ctctgagctt gagtgaagaa    2820
aataatgatt caaagttgtt agaatcaggt ttaatgaata gccaagaaag ttcatgggga    2880
aaaaatgtat cgtcaacaga gagtggtagg ttatttaaag ggaaaagagc tcatggacct    2940
gctttgttga ctaaagataa tgccttattc aaagttagca tctctttgtt aaagacaaac    3000
aaaacttcca ataattcagc aactaataga aagactcaca ttgatggccc atcattatta    3060
attgagaata gtccatcagt ctggcaaaat atattagaaa gtgacactga gtttaaaaaa    3120
gtgacacctt tgattcatga cagaatgctt atggacaaaa atgctacagc tttgaggcta    3180
aatcatatgt caaataaaac tacttcatca aaaaacatgg aaatggtcca acagaaaaaa    3240
gagggcccca ttccaccaga tgcacaaaat ccagatatgt cgttctttaa gatgctattc    3300
ttgccagaat cagcaaggtg gatacaaagg actcatggaa agaactctct gaactctggg    3360
caaggcccca gtccaaagca attagtatcc ttaggaccag aaaaatctgt ggaaggtcag    3420
aatttcttgt ctgagaaaaa caaagtggta gtaggaaagg gtgaatttac aaaggacgta    3480
ggactcaaag agatggtttt tccaagcagc agaaacctat ttcttactaa cttggataat    3540
ttacatgaaa ataatacaca caatcaagaa aaaaaaattc aggaagaaat agaaaagaag    3600
gaaacattaa tccaagagaa tgtagttttg cctcagatac atacagtgac tggcactaag    3660
aatttcatga gaaccttttt cttactgagc actaggcaaa atgtagaagg ttcatatgac    3720
ggggcatatg ctccagtact tcaagatttt aggtcattaa atgattcaac aaatagaaca    3780
aagaaacaca cagctcattt ctcaaaaaaa ggggaggaag aaaacttgga aggcttggga    3840
aatcaaacca agcaaattgt agagaaatat gcatgcacca caaggatatc tcctaataca    3900
agccagcaga ttttgtcac gcaacgtagt aagagagctt tgaaacaatt cagactccca    3960
ctagaagaaa cagaacttga aaaaggata attgtggatg acacctcaac ccagtggtcc    4020
aaaaacatga acatttgac cccgagcacc ctcacacaga tagactacaa tgagaaggag    4080
aaaggggcca ttactcagtc tcccttatca gattgcctta cgaggagtca tagcatccct    4140
caagcaaata gatctccatt acccattgca aaggtatcat catttccatc tattagacct    4200
atatatctga ccagggtcct attccaagac aactcttctc atcttccagc agcatcttat    4260
agaaagaaag attctggggt ccaagaaagc agtcatttct tacaaggagc caaaaaaaat    4320
```

```
aacctttctt tagccattct aaccttggag atgactggtg atcaaagaga ggttggctcc    4380
ctggggacaa gtgccacaaa ttcagtcaca tacaagaaag ttgagaacac tgttctcccg    4440
aaaccagact tgcccaaaac atctggcaaa gttgaattgc ttccaaaagt tcacatttat    4500
cagaaggacc tattccctac ggaaactagc aatgggtctc ctggccatct ggatctcgtg    4560
gaagggagcc ttcttcaggg aacagaggga gcgattaagt ggaatgaagc aaacagacct    4620
ggaaaagttc cctttctgag agtagcaaca gaaagctctg caaagactcc ctccaagcta    4680
ttggatcctc ttgcttggga taaccactat ggtactcaga taccaaaaga agagtggaaa    4740
tcccaagaga agtcaccaga aaaaacagct tttaagaaaa aggataccat tttgtccctg    4800
aacgcttgtg aaagcaatca tgcaatagca gcaataaatg agggacaaaa taagcccgaa    4860
atagaagtca cctgggcaaa gcaaggtagg actgaaaggc tgtgctctca aaacccacca    4920
gtcttgaaac gccatcaacg ggaataact cgtactactc ttcagtcaga tcaagaggaa    4980
attgactatg atgataccat atcagttgaa atgaagaagg aagattttga catttatgat    5040
gaggatgaaa atcagagccc ccgcagcttt caaaagaaaa cacgacacta ttttattgct    5100
gcagtggaga ggctctggga ttatgggatg agtagctccc cacatgttct aagaaacagg    5160
gctcagagtg gcagtgtccc tcagttcaag aaagttgttt tccaggaatt tactgatggc    5220
tcctttactc agcccttata ccgtggagaa ctaaatgaac atttgggact cctggggcca    5280
tatataagag cagaagttga agataatatc atggtaactt tcagaaatca ggcctctcgt    5340
ccctattcct tctattctag ccttatttct tatgaggaag atcagaggca aggagcagaa    5400
cctagaaaaa actttgtcaa gcctaatgaa accaaaactt acttttggaa agtgcaacat    5460
catatggcac ccactaaaga tgagtttgac tgcaaagcct gggcttattt ctctgatgtt    5520
gacctggaaa aagatgtgca ctcaggcctg attggacccc ttctggtctg ccacactaac    5580
acactgaacc ctgctcatgg gagacaagtg acagtacagg aatttgctct gttttttcacc    5640 atctttgatg agaccaaaag ctggtacttc actgaaaata tggaaagaaa ctgcagggct    5700
ccctgcaata tccagatgga agatcccact tttaaagaga attatcgctt ccatgcaatc    5760
aatggctaca taatggatac actacctggc ttagtaatgg ctcaggatca aaggattcga    5820
tggtatctgc tcagcatggg cagcaatgaa acatccatt ctattcattt cagtggacat    5880
gtgttcactg tacgaaaaaa agaggagtat aaaatggcac tgtacaatct ctatccaggt    5940
gtttttgaga cagtggaaat gttaccatcc aaagctggaa tttggcgggt ggaatgcctt    6000
attggcgagc atctacatgc tgggatgagc acacttttc tggtgtacag caataagtgt    6060
cagactcccc tgggaatggc ttctggacac attagagatt ttcagattac agcttcagga    6120
caatatggac agtgggcccc aaagctggcc agacttcatt attccggatc aatcaatgcc    6180
tggagcacca aggagccctt tcttggatc aaggtggatc tgttggcacc aatgattatt    6240
cacggcatca gacccagggg tgcccgtcag aagttctcca gcctctacat ctctcagttt    6300
atcatcatgt atagtcttga tgggaagaag tggcagactt atcgaggaaa ttccactgga    6360
accttaatgg tcttctttgg caatgtggat tcatctggga taaaacacaa tattttaac    6420 cctccaatta ttgctcgata catccgtttg cacccaactc attatagcat cgcagcact    6480 cttcgcatgg agttgatggg ctgtgattta aatagttgca gcatgccatt gggaatggag    6540
agtaaagcaa tatcagatgc acagattact gcttcatcct actttaccaa tatgtttgcc    6600
acctggtctc cttcaaaagc tcgacttcac ctccaaggga ggagtaatgc ctggagacct    6660
caggtgaata atccaaaaga gtggctgcaa gtggacttcc agaagacaat gaaagtcaca    6720
```

```
ggagtaacta ctcagggagt aaaatctctg cttaccagca tgtatgtgaa ggagttcctc    6780
atctccagca gtcaagatgg ccatcagtgg actctctttt ttcagaatgg caaagtaaag    6840
gttttccagg gaaatcaaga ctccttcaca cctgtggtga actctctaga cccaccgtta    6900
ctgactcgct accttcgaat tcaccccag agttgggtgc accagattgc ctgaggatg    6960 gaggttctgg gctgcgaggc acaggacctc tacgacaaaa ctcacacatg cccaccgtgc    7020
ccagctccag aactcctggg cggaccgtca gtcttcctct tccccccaaa acccaaggac    7080
accctcatga tctcccggac ccctgaggtc acatgcgtgg tggtggacgt gagccacgaa    7140
gaccctgagg tcaagttcaa ctggtacgtg gacggcgtgg aggtgcataa tgccaagaca    7200
aagccgcggg aggagcagta caacagcacg taccgtgtgg tcagcgtcct caccgtcctg    7260
caccaggact ggctgaatgg caaggagtac aagtgcaagg tctccaacaa agccctccca    7320
gcccccatcg agaaaaccat ctccaaagcc aaagggcagc cccgagaacc acaggtgtac    7380
accctgcccc catcccggga tgagctgacc aagaaccagg tcagcctgac ctgcctggtc    7440
aaaggcttct atcccagcga catcgccgtg gagtgggaga gcaatgggca gccggagaac    7500
aactacaaga ccacgcctcc cgtgttggac tccgacggct ccttcttcct ctacagcaag    7560
ctcaccgtgg acaagagcag gtggcagcag gggaacgtct tctcatgctc cgtgatgcat    7620
gaggctctgc acaaccacta cacgcagaag agcctctccc tgtctccggg taaa         7674
```

<210> SEQ ID NO 6
<211> LENGTH: 2578
<212> TYPE: PRT
<213> ORGANISM: Artificial Sequence
<220> FEATURE:
<223> OTHER INFORMATION: Full Length FVIIIFc
<220> FEATURE:
<221> NAME/KEY: SIGNAL
<222> LOCATION: (1)..(19)
<220> FEATURE:
<221> NAME/KEY: MISC_FEATURE
<222> LOCATION: (2331)..(2578)
<223> OTHER INFORMATION: Fc region

<400> SEQUENCE: 6

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160
```

```
Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575
```

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
            610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
            645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
            675                 680                 685

Leu Phe Pro Phe Ser Gly Glu Thr Val Phe Met Ser Met Glu Asn Pro
            690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
            725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
            805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
            885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
            915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
            965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala

-continued

```
            995                 1000                1005
Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395
```

```
Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785
```

```
Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160

Ile Ala Arg Tyr Ile Arg Leu His Pro Thr His Tyr Ser Ile Arg
2165                2170                2175

Ser Thr Leu Arg Met Glu Leu Met Gly Cys Asp Leu Asn Ser Cys
```

```
            2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr Asp Lys Thr His Thr Cys Pro
    2345                2350                2355

Pro Cys Pro Ala Pro Glu Leu Leu Gly Gly Pro Ser Val Phe Leu
    2360                2365                2370

Phe Pro Pro Lys Pro Lys Asp Thr Leu Met Ile Ser Arg Thr Pro
    2375                2380                2385

Glu Val Thr Cys Val Val Val Asp Val Ser His Glu Asp Pro Glu
    2390                2395                2400

Val Lys Phe Asn Trp Tyr Val Asp Gly Val Glu Val His Asn Ala
    2405                2410                2415

Lys Thr Lys Pro Arg Glu Glu Gln Tyr Asn Ser Thr Tyr Arg Val
    2420                2425                2430

Val Ser Val Leu Thr Val Leu His Gln Asp Trp Leu Asn Gly Lys
    2435                2440                2445

Glu Tyr Lys Cys Lys Val Ser Asn Lys Ala Leu Pro Ala Pro Ile
    2450                2455                2460

Glu Lys Thr Ile Ser Lys Ala Lys Gly Gln Pro Arg Glu Pro Gln
    2465                2470                2475

Val Tyr Thr Leu Pro Pro Ser Arg Asp Glu Leu Thr Lys Asn Gln
    2480                2485                2490

Val Ser Leu Thr Cys Leu Val Lys Gly Phe Tyr Pro Ser Asp Ile
    2495                2500                2505

Ala Val Glu Trp Glu Ser Asn Gly Gln Pro Glu Asn Asn Tyr Lys
    2510                2515                2520

Thr Thr Pro Pro Val Leu Asp Ser Asp Gly Ser Phe Phe Leu Tyr
    2525                2530                2535

Ser Lys Leu Thr Val Asp Lys Ser Arg Trp Gln Gln Gly Asn Val
    2540                2545                2550

Phe Ser Cys Ser Val Met His Glu Ala Leu His Asn His Tyr Thr
    2555                2560                2565

Gln Lys Ser Leu Ser Leu Ser Pro Gly Lys
    2570                2575
```

<210> SEQ ID NO 7
<211> LENGTH: 2957
<212> TYPE: DNA
<213> ORGANISM: Artificial Sequence
<220> FEATURE:
<223> OTHER INFORMATION: Heavy Chain (HC)-Fc
<220> FEATURE:
<221> NAME/KEY: sig_peptide
<222> LOCATION: (1)..(57)

<400> SEQUENCE: 7

```
atgcaaatag agctctccac ctgcttcttt ctgtgccttt tgcgattctg ctttagtgcc    60
accagaagat actacctggg tgcagtggaa ctgtcatggg actatatgca aagtgatctc   120
ggtgagctgc ctgtggacgc aagatttcct cctagagtgc aaaatctttt ccattcaac    180
acctcagtcg tgtacaaaaa gactctgttt gtagaattca cggatcacct tttcaacatc   240
gctaagccaa ggccaccctg gatgggtctg ctaggtccta ccatccaggc tgaggtttat   300
gatacagtgg tcattacact aagaacatg gcttcccatc ctgtcagtct tcatgctgtt   360
ggtgtatcct actggaaagc ttctgaggga gctgaatatg atgatcagac cagtcaaagg   420
gagaaagaag atgataaagt cttccctggt ggaagccata catatgtctg gcaggtcctg   480
aaagagaatg gtccaatggc ctctgaccca ctgtgcctta cctactcata tctttctcat   540
gtggacctgg taaagacttt gaattcaggc ctcattggag ccctactagt atgtagagag   600
ggagtctggc aaggaaaag acacagacct tgcacaaatt tatactactt tttgctgtat   660
ttgatgaagg gaaagttgg cactcagaaa caagaactc cttgatgcag atagggatg    720
ctgcatctgc tcgggcctgg cctaaaatgc acacagtcaa tggttatgta aacaggtctc   780
tgccaggtct gattggatgc acaggaaat cagtctattg gcatgtgatt ggaatgggca   840
ccactcctga agtgcactca atattcctcg aaggtcacac atttcttgtg aggaaccatc   900
gccaggcgtc cttggaaatc tcgccaataa ctttccttac tgctcaaaca ctcttgatgg   960
accttggaca gtttctactg ttttgtcata tctcttccca ccaacatgat ggcatggaag  1020
cttatgtcaa agtagacagc tgtccagagg aacccaact acgaatgaaa ataatgaag   1080
aagcggaaga ctatgatgat gatcttactg attctgaaat ggatgtggtc aggtttgatg  1140
atgcaactc tccttccttt atccaaattc gctcagttgc caagaagcat cctaaaactt  1200
gggtacatta cattgctgct gaagaggagg actgggacta tgctccctta gtcctcgccc  1260
ccgatgacag aagttataaa agtcaatatt gaacaatgg ccctcagcgg attggtagga  1320
agtacaaaaa agtccgattt atggcataca cagatgaaac ctttaagact cgtgaagcta  1380
ttcagcatga atcaggaatc ttgggaccctt tactttatgg ggaagttgga gacacactgt  1440
tgattatatt taagaatcaa gcaagcagac catataacat ctaccctcac ggaatcactg  1500
atgtccgtcc tttgtattca aggagattac caaaaggtgt aaaacatttg aaggattttc  1560
caattctgcc aggagaaata ttcaaatata atggacagt gactgtagaa gatgggccaa  1620
ctaaatcaga tcctcggtgc ctgacccgct attactctag tttcgttaat atggagagag  1680
atctagcttc aggactcatt ggccctctcc tcatctgcta caagaatct gtagatcaaa  1740
gaggaaacca gataatgtca gacaagagga atgtcatcct gtttctgta tttgatgaga  1800
accgaagctg gtacctcaca gagaatatac aacgcttct ccccaatcca gctggagtgc  1860
agcttgagga tccagagttc caagcctcca acatcatgca cagcatcaat ggctatgttt  1920
tgatagtttt gcagttgtca gttgtttgc atgaggtggc atactggtac attctaagca  1980
```

-continued

```
ttggagcaca gactgacttc ctttctgtct tcttctctgg atataccttc aaacacaaaa    2040
tggtctatga agacacactc accctattcc cattctcagg agaaactgtc ttcatgtcga    2100
tggaaaaccc aggtctatgg attctggggt gccacaactc agactttcgg aacagaggca    2160
tgaccgcctt actgaaggtt tctagttgtg acaagaacac tggtgattat tacgaggaca    2220
gttatgaaga tatttcagca tacttgctga gtaaaaacaa tgccattgaa ccaagagaca    2280
aaactcacac atgccaccg tgcccagctc cagaactcct gggcggaccg tcagtcttcc     2340
tcttcccccc aaaacccaag gacaccctca tgatctcccg gaccctgag gtcacatgcg     2400 tggtggtgga cgtgagccac gaagaccctg aggtcaagtt caactggtac gtggacggcg   2460
tggaggtgca taatgccaag acaaagccgc gggaggagca gtacaacagc acgtaccgtg   2520
tggtcagcgt cctcaccgtc ctgcaccagg actggctgaa tggcaaggag tacaagtgca   2580
aggtctccaa caaagccctc ccagccccca tcgagaaaac catctccaaa gccaagggc    2640 agccccgaga accacaggtg tacaccctgc cccatcccg ggatgagctg accaagaacc    2700
aggtcagcct gacctgcctg gtcaaaggct tctatcccag cgacatcgcc gtggagtggg   2760
agagcaatgg gcagccggag aacaactaca agaccacgcc tcccgtgttg gactccgacg   2820
gctccttctt cctctacagc aagctcaccg tggacaagag caggtggcag caggggaacg    2880
tcttctcatg ctccgtgatg catgaggctc tgcacaacca ctacacgcag aagagcctct    2940
ccctgtctcc gggtaaa                                                   2957
```

<210> SEQ ID NO 8
<211> LENGTH: 986
<212> TYPE: PRT
<213> ORGANISM: Artificial Sequence
<220> FEATURE:
<223> OTHER INFORMATION: Heavy Chain (HC)-Fc
<220> FEATURE:
<221> NAME/KEY: SIGNAL
<222> LOCATION: (1)..(19)

<400> SEQUENCE: 8

```
Met Gln Ile Glu Leu Ser Thr Cys Phe Phe Leu Cys Leu Leu Arg Phe
1               5                  10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
```

```
                165                 170                 175
Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
            530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590
```

```
Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Asp Lys Thr His Thr Cys Pro Pro Cys
        755                 760                 765

Pro Ala Pro Glu Leu Leu Gly Gly Pro Ser Val Phe Leu Phe Pro Pro
770                 775                 780

Lys Pro Lys Asp Thr Leu Met Ile Ser Arg Thr Pro Glu Val Thr Cys
785                 790                 795                 800

Val Val Val Asp Val Ser His Glu Asp Pro Glu Val Lys Phe Asn Trp
                805                 810                 815

Tyr Val Asp Gly Val Glu Val His Asn Ala Lys Thr Lys Pro Arg Glu
            820                 825                 830

Glu Gln Tyr Asn Ser Thr Tyr Arg Val Val Ser Val Leu Thr Val Leu
        835                 840                 845

His Gln Asp Trp Leu Asn Gly Lys Glu Tyr Lys Cys Lys Val Ser Asn
    850                 855                 860

Lys Ala Leu Pro Ala Pro Ile Glu Lys Thr Ile Ser Lys Ala Lys Gly
865                 870                 875                 880

Gln Pro Arg Glu Pro Gln Val Tyr Thr Leu Pro Pro Ser Arg Asp Glu
                885                 890                 895

Leu Thr Lys Asn Gln Val Ser Leu Thr Cys Leu Val Lys Gly Phe Tyr
            900                 905                 910

Pro Ser Asp Ile Ala Val Glu Trp Glu Ser Asn Gly Gln Pro Glu Asn
        915                 920                 925

Asn Tyr Lys Thr Thr Pro Pro Val Leu Asp Ser Asp Gly Ser Phe Phe
    930                 935                 940

Leu Tyr Ser Lys Leu Thr Val Asp Lys Ser Arg Trp Gln Gln Gly Asn
945                 950                 955                 960

Val Phe Ser Cys Ser Val Met His Glu Ala Leu His Asn His Tyr Thr
                965                 970                 975

Gln Lys Ser Leu Ser Leu Ser Pro Gly Lys
            980                 985

<210> SEQ ID NO 9
<211> LENGTH: 2973
```

```
<212> TYPE: DNA
<213> ORGANISM: Artificial Sequence
<220> FEATURE:
<223> OTHER INFORMATION: Heavy Chain (HC)-Fc
<220> FEATURE:
<221> NAME/KEY: sig_peptide
<222> LOCATION: (1)..(57)
<220> FEATURE:
<221> NAME/KEY: misc_feature
<222> LOCATION: (2277)..(2292)
<223> OTHER INFORMATION: amino acid linker

<400> SEQUENCE: 9
```

| | | | | |
|---|---|---|---|---|
| atgcaaatag | agctctccac | ctgcttcttt | ctgtgccttt | tgcgattctg | ctttagtgcc | 60 |
| accagaagat | actacctggg | tgcagtggaa | ctgtcatggg | actatatgca | aagtgatctc | 120 |
| ggtgagctgc | ctgtggacgc | aagatttcct | cctagagtgc | caaaatcttt | tccattcaac | 180 |
| acctcagtcg | tgtacaaaaa | gactctgttt | gtagaattca | cggatcacct | tttcaacatc | 240 |
| gctaagccaa | ggccaccctg | gatgggtctg | ctaggtccta | ccatccaggc | tgaggtttat | 300 |
| gatacagtgg | tcattacact | taagaacatg | gcttcccatc | ctgtcagtct | tcatgctgtt | 360 |
| ggtgtatcct | actggaaagc | ttctgaggga | gctgaatatg | atgatcagac | cagtcaaagg | 420 |
| gagaaagaag | atgataaagt | cttccctggt | ggaagccata | catatgtctg | gcaggtcctg | 480 |
| aaagagaatg | gtccaatggc | ctctgaccca | ctgtgcctta | cctactcata | tctttctcat | 540 |
| gtggacctgg | taaagacttt | gaattcaggc | ctcattggag | ccctactagt | atgtagagaa | 600 |
| gggagtctgg | ccaaggaaaa | gacacagacc | ttgcacaaat | ttatactact | ttttgctgta | 660 |
| tttgatgaag | ggaaaagttg | gcactcagaa | acaaagaact | ccttgatgca | ggatagggat | 720 |
| gctgcatctg | ctcgggcctg | gcctaaaatg | cacacagtca | atggttatgt | aaacaggtct | 780 |
| ctgccaggtc | tgattggatg | ccacaggaaa | tcagtctatt | ggcatgtgat | tggaatgggc | 840 |
| accactcctg | aagtgcactc | aatattcctc | gaaggtcaca | catttcttgt | gaggaaccat | 900 |
| cgccaggcgt | ccttggaaat | ctcgccaata | actttcctta | ctgctcaaac | actcttgatg | 960 |
| gaccttggac | agtttctact | gttttgtcat | atctcttccc | accaacatga | tggcatggaa | 1020 |
| gcttatgtca | aagtagacag | ctgtccagag | gaacccaac | tacgaatgaa | aaataatgaa | 1080 |
| gaagcggaag | actatgatga | tgatcttact | gattctgaaa | tggatgtggt | caggtttgat | 1140 |
| gatgacaact | ctccttcctt | tatccaaatt | cgctcagttg | ccaagaagca | tcctaaaact | 1200 |
| tgggtacatt | acattgctgc | tgaagaggag | gactgggact | atgctccctt | agtcctcgcc | 1260 |
| cccgatgaca | gaagttataa | aagtcaatat | ttgaacaatg | gccctcagcg | gattggtagg | 1320 |
| aagtacaaaa | aagtccgatt | tatggcatac | acagatgaaa | cctttaagac | tcgtgaagct | 1380 |
| attcagcatg | aatcaggaat | cttgggacct | tactttatg | ggaagttgg | agacacactg | 1440 |
| ttgattatat | taagaatca | agcaagcaga | ccatataaca | tctaccctca | cggaatcact | 1500 |
| gatgtccgtc | ctttgtattc | aaggagatta | ccaaaaggtg | taaacatttt | gaaggatttt | 1560 |
| ccaattctgc | caggagaaat | attcaaatat | aaatggacag | tgactgtaga | agatgggcca | 1620 |
| actaaatcag | atcctcggtg | cctgacccgc | tattactcta | gtttcgttaa | tatggagaga | 1680 |
| gatctagctt | caggactcat | tggccctctc | ctcatctgct | acaaagaatc | tgtagatcaa | 1740 |
| agaggaaacc | agataatgtc | agacaagagg | aatgtcatcc | tgttttctgt | atttgatgag | 1800 |
| aaccgaagct | ggtacctcac | agagaatata | caacgctttc | tccccaatcc | agctggagtg | 1860 |
| cagcttgagg | atccagagtt | ccaagcctcc | aacatcatgc | acagcatcaa | tggctatgtt | 1920 |
| tttgatagtt | tgcagttgtc | agtttgtttg | catgaggtgg | catactggta | cattctaagc | 1980 |

-continued

```
attggagcac agactgactt cctttctgtc ttcttctctg gatataccctt caaacacaaa    2040 atggtctatg aagacacact cacccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga atgacaaaac tcacacatgc ccaccgtgcc cagctccaga actcctgggc    2340
ggaccgtcag tcttcctctt ccccccaaaa cccaaggaca ccctcatgat ctcccggacc    2400
cctgaggtca catgcgtggt ggtggacgtg agccacgaag accctgaggt caagttcaac    2460
tggtacgtgg acggcgtgga ggtgcataat gccaagacaa agccgcggga ggagcagtac    2520
aacagcacgt accgtgtggt cagcgtcctc accgtcctgc accaggactg gctgaatggc    2580
aaggagtaca agtgcaaggt ctccaacaaa gccctcccag cccccatcga gaaaaccatc    2640
tccaaagcca aagggcagcc ccgagaacca caggtgtaca ccctgccccc atcccgggat    2700
gagctgacca agaaccaggt cagcctgacc tgcctggtca aaggcttcta tcccagcgac    2760
atcgccgtgg agtgggagag caatgggcag ccggagaaca actacaagac cacgcctccc    2820
gtgttggact ccgacggctc cttcttcctc tacagcaagc tcaccgtgga caagagcagg    2880
tggcagcagg ggaacgtctt ctcatgctcc gtgatgcatg aggctctgca caaccactac    2940
acgcagaaga gcctctccct gtctccgggt aaa                                 2973
```

<210> SEQ ID NO 10
<211> LENGTH: 991
<212> TYPE: PRT
<213> ORGANISM: Artificial Sequence
<220> FEATURE:
<223> OTHER INFORMATION: Heavy Chain (HC)-Fc
<220> FEATURE:
<221> NAME/KEY: SIGNAL
<222> LOCATION: (1)..(19)
<220> FEATURE:
<221> NAME/KEY: MISC_FEATURE
<222> LOCATION: (759)..(764)
<223> OTHER INFORMATION: Linker

<400> SEQUENCE: 10

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140
```

```
Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
```

```
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
        610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
        690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gln Asn Asp Lys Thr His
        755                 760                 765
Thr Cys Pro Pro Cys Pro Ala Pro Glu Leu Leu Gly Gly Pro Ser Val
770                 775                 780
Phe Leu Phe Pro Pro Lys Pro Lys Asp Thr Leu Met Ile Ser Arg Thr
785                 790                 795                 800
Pro Glu Val Thr Cys Val Val Val Asp Val Ser His Glu Asp Pro Glu
                805                 810                 815
Val Lys Phe Asn Trp Tyr Val Asp Gly Val Glu Val His Asn Ala Lys
                820                 825                 830
Thr Lys Pro Arg Glu Glu Gln Tyr Asn Ser Thr Tyr Arg Val Val Ser
        835                 840                 845
Val Leu Thr Val Leu His Gln Asp Trp Leu Asn Gly Lys Glu Tyr Lys
        850                 855                 860
Cys Lys Val Ser Asn Lys Ala Leu Pro Ala Pro Ile Glu Lys Thr Ile
865                 870                 875                 880
Ser Lys Ala Lys Gly Gln Pro Arg Glu Pro Gln Val Tyr Thr Leu Pro
                885                 890                 895
Pro Ser Arg Asp Glu Leu Thr Lys Asn Gln Val Ser Leu Thr Cys Leu
                900                 905                 910
Val Lys Gly Phe Tyr Pro Ser Asp Ile Ala Val Glu Trp Glu Ser Asn
                915                 920                 925
Gly Gln Pro Glu Asn Asn Tyr Lys Thr Thr Pro Pro Val Leu Asp Ser
        930                 935                 940
Asp Gly Ser Phe Phe Leu Tyr Ser Lys Leu Thr Val Asp Lys Ser Arg
945                 950                 955                 960
Trp Gln Gln Gly Asn Val Phe Ser Cys Ser Val Met His Glu Ala Leu
                965                 970                 975
His Asn His Tyr Thr Gln Lys Ser Leu Ser Leu Ser Pro Gly Lys
                980                 985                 990
```

<210> SEQ ID NO 11
<211> LENGTH: 2793
<212> TYPE: DNA
<213> ORGANISM: Artificial Sequence
<220> FEATURE:
<223> OTHER INFORMATION: Light Chain (LC)-Fc
<220> FEATURE:
<221> NAME/KEY: sig_peptide
<222> LOCATION: (1)..(60)

<400> SEQUENCE: 11

| | | | | | |
|---|---|---|---|---|---|
| atggagacag | acacactcct | gctatgggta | ctgctgctct | gggttccagg | ttccactggt | 60 |
| gaaataactc | gtactactct | tcagtcagat | caagaggaaa | ttgactatga | tgataccata | 120 |
| tcagttgaaa | tgaagaagga | agattttgac | atttatgatg | aggatgaaaa | tcagagcccc | 180 |
| cgcagctttc | aaaagaaaac | acgacactat | tttattgctg | cagtggagag | gctctgggat | 240 |
| tatgggatga | gtagctcccc | acatgttcta | agaaacaggg | ctcagagtgg | cagtgtccct | 300 |
| cagttcaaga | aagttgtttt | ccaggaattt | actgatggcc | cctttactca | gcccttatac | 360 |
| cgtggagaac | taatgaaca | tttgggactc | ctggggccat | atataagagc | agaagttgaa | 420 |
| gataatatca | tggtaacttt | cagaaatcag | gcctctcgtc | cctattcctt | ctattctagc | 480 |
| cttatttctt | atgaggaaga | tcagaggcaa | ggagcagaac | tagaaaaaa | ctttgtcaag | 540 |
| cctaatgaaa | ccaaaactta | cttttggaaa | gtgcaacatc | atatggcacc | cactaaagat | 600 |
| gagtttgact | gcaaagcctg | ggcttatttc | tctgatgttg | acctggaaaa | agatgtgcac | 660 |
| tcaggcctga | ttggaccct | tctggtctgc | cacactaaca | cactgaaccc | tgctcatggg | 720 |
| agacaagtga | cagtacagga | atttgctctg | tttttcacca | tctttgatga | gaccaaaagc | 780 |
| tggtacttca | ctgaaaatat | ggaaagaaac | tgcagggctc | cctgcaatat | ccagatggaa | 840 |
| gatcccactt | ttaaagagaa | ttatcgcttc | catgcaatca | atggctacat | aatggataca | 900 |
| ctacctggct | tagtaatggc | tcaggatcaa | aggattcgat | ggtatctgct | cagcatgggc | 960 |
| agcaatgaaa | acatccattc | tattcatttc | agtggacatg | tgttcactgt | acgaaaaaaa | 1020 |
| gaggagtata | aaatggcact | gtacaatctc | tatccaggtg | tttttgagac | agtggaaatg | 1080 |
| ttaccatcca | agctggaat | tggcgggtg | gaatgcctta | ttggcgagca | tctacatgct | 1140 |
| gggatgagca | cacttttct | ggtgtacagc | aataagtgtc | agactcccct | gggaatggct | 1200 |
| tctggacaca | ttagagattt | tcagattaca | gcttcaggac | aatatggaca | gtgggcccca | 1260 |
| aagctggcca | gacttcatta | ttccggatca | atcaatgcct | ggagcaccaa | ggagcccttt | 1320 |
| tcttggatca | aggtggatct | gttggcacca | atgattattc | acggcatcaa | gacccagggt | 1380 |
| gcccgtcaga | agttctccag | cctctacatc | tctcagttta | tcatcatgta | tagtcttgat | 1440 |
| gggaagaagt | ggcagactta | tcgaggaaat | tccactggaa | ccttaatggt | cttctttggc | 1500 |
| aatgtggatt | catctgggat | aaaacacaat | attttaacc | ctccaattat | tgctcgatac | 1560 |
| atccgtttgc | acccaactca | ttatagcatt | cgcagcactc | ttcgcatgga | gttgatgggc | 1620 |
| tgtgatttaa | atagttgcag | catgccattg | ggaatggaga | gtaaagcaat | atcagatgca | 1680 |
| cagattactg | cttcatccta | ctttaccaat | atgtttgcca | cctggtctcc | ttcaaaagct | 1740 |
| cgacttcacc | tccaagggag | gagtaatgcc | tggagacctc | aggtgaataa | tccaaaagag | 1800 |
| tggctgcaag | tggacttcca | gaagacaatg | aaagtcacag | gagtaactac | tcagggagta | 1860 |
| aaatctctgc | ttaccagcat | gtatgtgaag | gagttcctca | tctccagcag | tcaagatggc | 1920 |
| catcagtgga | ctctcttttt | tcagaatggc | aaagtaaagg | ttttttcaggg | aaatcaagac | 1980 |

```
tccttcacac ctgtggtgaa ctctctagac ccaccgttac tgactcgcta ccttcgaatt    2040
cacccccaga gttgggtgca ccagattgcc ctgaggatgg aggttctggg ctgcgaggca    2100
caggacctct acgacaaaac tcacacatgc ccaccgtgcc cagctccaga actcctgggc    2160
ggaccgtcag tcttcctctt ccccccaaaa cccaaggaca ccctcatgat ctcccggacc    2220
cctgaggtca catgcgtggt ggtggacgtg agccacgaag accctgaggt caagttcaac    2280
tggtacgtgg acggcgtgga ggtgcataat gccaagacaa agccgcggga ggagcagtac    2340
aacagcacgt accgtgtggt cagcgtcctc accgtcctgc accaggactg gctgaatggc    2400
aaggagtaca agtgcaaggt ctccaacaaa gccctcccag cccccatcga gaaaaccatc    2460
tccaaagcca agggcagccc cgagaaccac aggtgtaca ccctgccccc atcccgggat    2520
gagctgacca gaaccaggt cagcctgacc tgcctggtca aaggcttcta tcccagcgac    2580
atcgccgtgg agtgggagag caatgggcag ccggagaaca actacaagac cacgcctccc    2640
gtgttggact ccgacggctc cttcttcctc tacagcaagc tcaccgtgga caagagcagg    2700
tggcagcagg ggaacgtctt ctcatgctcc gtgatgcatg aggctctgca caaccactac    2760
acgcagaaga gcctctccct gtctccgggt aaa    2793
```

<210> SEQ ID NO 12
<211> LENGTH: 931
<212> TYPE: PRT
<213> ORGANISM: Artificial Sequence
<220> FEATURE:
<223> OTHER INFORMATION: Light Chain (LC)-Fc
<220> FEATURE:
<221> NAME/KEY: SIGNAL
<222> LOCATION: (1)..(20)

<400> SEQUENCE: 12

```
Met Glu Thr Asp Thr Leu Leu Leu Trp Val Leu Leu Leu Trp Val Pro
1               5                   10                  15

Gly Ser Thr Gly Glu Ile Thr Arg Thr Thr Leu Gln Ser Asp Gln Glu
            20                  25                  30

Glu Ile Asp Tyr Asp Asp Thr Ile Ser Val Glu Met Lys Lys Glu Asp
        35                  40                  45

Phe Asp Ile Tyr Asp Glu Asp Glu Asn Gln Ser Pro Arg Ser Phe Gln
    50                  55                  60

Lys Lys Thr Arg His Tyr Phe Ile Ala Ala Val Glu Arg Leu Trp Asp
65                  70                  75                  80

Tyr Gly Met Ser Ser Ser Pro His Val Leu Arg Asn Arg Ala Gln Ser
                85                  90                  95

Gly Ser Val Pro Gln Phe Lys Lys Val Val Phe Gln Glu Phe Thr Asp
            100                 105                 110

Gly Ser Phe Thr Gln Pro Leu Tyr Arg Gly Glu Leu Asn Glu His Leu
        115                 120                 125

Gly Leu Leu Gly Pro Tyr Ile Arg Ala Glu Val Glu Asp Asn Ile Met
    130                 135                 140

Val Thr Phe Arg Asn Gln Ala Ser Arg Pro Tyr Ser Phe Tyr Ser Ser
145                 150                 155                 160

Leu Ile Ser Tyr Glu Glu Asp Gln Arg Gln Gly Ala Glu Pro Arg Lys
                165                 170                 175

Asn Phe Val Lys Pro Asn Glu Thr Lys Thr Tyr Phe Trp Lys Val Gln
            180                 185                 190

His His Met Ala Pro Thr Lys Asp Glu Phe Asp Cys Lys Ala Trp Ala
```

```
            195                 200                 205
Tyr Phe Ser Asp Val Asp Leu Glu Lys Asp Val His Ser Gly Leu Ile
    210                 215                 220

Gly Pro Leu Leu Val Cys His Thr Asn Thr Leu Asn Pro Ala His Gly
225                 230                 235                 240

Arg Gln Val Thr Val Gln Glu Phe Ala Leu Phe Phe Thr Ile Phe Asp
                245                 250                 255

Glu Thr Lys Ser Trp Tyr Phe Thr Glu Asn Met Glu Arg Asn Cys Arg
            260                 265                 270

Ala Pro Cys Asn Ile Gln Met Glu Asp Pro Thr Phe Lys Glu Asn Tyr
        275                 280                 285

Arg Phe His Ala Ile Asn Gly Tyr Ile Met Asp Thr Leu Pro Gly Leu
    290                 295                 300

Val Met Ala Gln Asp Gln Arg Ile Arg Trp Tyr Leu Leu Ser Met Gly
305                 310                 315                 320

Ser Asn Glu Asn Ile His Ser Ile His Phe Ser Gly His Val Phe Thr
                325                 330                 335

Val Arg Lys Lys Glu Glu Tyr Lys Met Ala Leu Tyr Asn Leu Tyr Pro
            340                 345                 350

Gly Val Phe Glu Thr Val Glu Met Leu Pro Ser Lys Ala Gly Ile Trp
        355                 360                 365

Arg Val Glu Cys Leu Ile Gly Glu His Leu His Ala Gly Met Ser Thr
    370                 375                 380

Leu Phe Leu Val Tyr Ser Asn Lys Cys Gln Thr Pro Leu Gly Met Ala
385                 390                 395                 400

Ser Gly His Ile Arg Asp Phe Gln Ile Thr Ala Ser Gly Gln Tyr Gly
                405                 410                 415

Gln Trp Ala Pro Lys Leu Ala Arg Leu His Tyr Ser Gly Ser Ile Asn
            420                 425                 430

Ala Trp Ser Thr Lys Glu Pro Phe Ser Trp Ile Lys Val Asp Leu Leu
        435                 440                 445

Ala Pro Met Ile Ile His Gly Ile Lys Thr Gln Gly Ala Arg Gln Lys
    450                 455                 460

Phe Ser Ser Leu Tyr Ile Ser Gln Phe Ile Ile Met Tyr Ser Leu Asp
465                 470                 475                 480

Gly Lys Lys Trp Gln Thr Tyr Arg Gly Asn Ser Thr Gly Thr Leu Met
                485                 490                 495

Val Phe Phe Gly Asn Val Asp Ser Ser Gly Ile Lys His Asn Ile Phe
            500                 505                 510

Asn Pro Pro Ile Ile Ala Arg Tyr Ile Arg Leu His Pro Thr His Tyr
        515                 520                 525

Ser Ile Arg Ser Thr Leu Arg Met Glu Leu Met Gly Cys Asp Leu Asn
    530                 535                 540

Ser Cys Ser Met Pro Leu Gly Met Glu Ser Lys Ala Ile Ser Asp Ala
545                 550                 555                 560

Gln Ile Thr Ala Ser Ser Tyr Phe Thr Asn Met Phe Ala Thr Trp Ser
                565                 570                 575

Pro Ser Lys Ala Arg Leu His Leu Gln Gly Arg Ser Asn Ala Trp Arg
            580                 585                 590

Pro Gln Val Asn Asn Pro Lys Glu Trp Leu Gln Val Asp Phe Gln Lys
        595                 600                 605

Thr Met Lys Val Thr Gly Val Thr Thr Gln Gly Val Lys Ser Leu Leu
    610                 615                 620
```

-continued

```
Thr Ser Met Tyr Val Lys Glu Phe Leu Ile Ser Ser Gln Asp Gly
625                 630                 635                 640

His Gln Trp Thr Leu Phe Phe Gln Asn Gly Lys Val Lys Val Phe Gln
            645                 650                 655

Gly Asn Gln Asp Ser Phe Thr Pro Val Val Asn Ser Leu Asp Pro Pro
            660                 665                 670

Leu Leu Thr Arg Tyr Leu Arg Ile His Pro Gln Ser Trp Val His Gln
        675                 680                 685

Ile Ala Leu Arg Met Glu Val Leu Gly Cys Glu Ala Gln Asp Leu Tyr
690                 695                 700

Asp Lys Thr His Thr Cys Pro Pro Cys Pro Ala Pro Glu Leu Leu Gly
705                 710                 715                 720

Gly Pro Ser Val Phe Leu Phe Pro Pro Lys Pro Lys Asp Thr Leu Met
            725                 730                 735

Ile Ser Arg Thr Pro Glu Val Thr Cys Val Val Val Asp Val Ser His
            740                 745                 750

Glu Asp Pro Glu Val Lys Phe Asn Trp Tyr Val Asp Gly Val Glu Val
        755                 760                 765

His Asn Ala Lys Thr Lys Pro Arg Glu Glu Gln Tyr Asn Ser Thr Tyr
770                 775                 780

Arg Val Val Ser Val Leu Thr Val Leu His Gln Asp Trp Leu Asn Gly
785                 790                 795                 800

Lys Glu Tyr Lys Cys Lys Val Ser Asn Lys Ala Leu Pro Ala Pro Ile
            805                 810                 815

Glu Lys Thr Ile Ser Lys Ala Lys Gly Gln Pro Arg Glu Pro Gln Val
            820                 825                 830

Tyr Thr Leu Pro Pro Ser Arg Asp Glu Leu Thr Lys Asn Gln Val Ser
        835                 840                 845

Leu Thr Cys Leu Val Lys Gly Phe Tyr Pro Ser Asp Ile Ala Val Glu
850                 855                 860

Trp Glu Ser Asn Gly Gln Pro Glu Asn Asn Tyr Lys Thr Thr Pro Pro
865                 870                 875                 880

Val Leu Asp Ser Asp Gly Ser Phe Phe Leu Tyr Ser Lys Leu Thr Val
            885                 890                 895

Asp Lys Ser Arg Trp Gln Gln Gly Asn Val Phe Ser Cys Ser Val Met
            900                 905                 910

His Glu Ala Leu His Asn His Tyr Thr Gln Lys Ser Leu Ser Leu Ser
        915                 920                 925

Pro Gly Lys
    930

<210> SEQ ID NO 13
<211> LENGTH: 7583
<212> TYPE: DNA
<213> ORGANISM: Artificial Sequence
<220> FEATURE:
<223> OTHER INFORMATION: FIX-Fc Chain
<220> FEATURE:
<221> NAME/KEY: exon
<222> LOCATION: (690)..(777)
<223> OTHER INFORMATION: FIX exon 1
<220> FEATURE:
<221> NAME/KEY: Intron
<222> LOCATION: (778)..(1076)
<223> OTHER INFORMATION: FIX mini intron
<220> FEATURE:
<221> NAME/KEY: misc_feature
<222> LOCATION: (1077)..(1126)
```

<223> OTHER INFORMATION: FIX propeptide
<220> FEATURE:
<221> NAME/KEY: misc_feature
<222> LOCATION: (1127)..(2371)
<223> OTHER INFORMATION: Mature FIX
<220> FEATURE:
<221> NAME/KEY: misc_feature
<222> LOCATION: (2372)..(3052)
<223> OTHER INFORMATION: Fc region

<400> SEQUENCE: 13

| | |
|---|---:|
| gcgcgcgttg acattgatta ttgactagtt attaatagta atcaattacg gggtcattag | 60 |
| ttcatagccc atatatggag ttccgcgtta cataacttac ggtaaatggc ccgcctggct | 120 |
| gaccgcccaa cgaccccgc ccattgacgt caataatgac gtatgttccc atagtaacgc | 180 |
| caatagggac tttccattga cgtcaatggg tggagtattt acggtaaact gcccacttgg | 240 |
| cagtacatca agtgtatcat atgccaagta cgccccctat tgacgtcaat gacggtaaat | 300 |
| ggcccgcctg gcattatgcc cagtacatga ccttatggga ctttcctact tggcagtaca | 360 |
| tctacgtatt agtcatcgct attaccatgg tgatgcggtt ttggcagtac atcaatgggc | 420 |
| gtggatagcg gtttgactca cggggatttc caagtctcca ccccattgac gtcaatggga | 480 |
| gtttgttttg gcaccaaaat caacgggact ttccaaaatg tcgtaacaac tccgccccat | 540 |
| tgacgcaaat gggcggtagg cgtgtacggt gggaggtcta taagcaga gctctctggc | 600 |
| taactagaga acccactgct tactggctta tcgaaattaa tacgactcac tatagggaga | 660 |
| cccaagcttc gcgacgtacg gccgccacc atg cag cgc gtg aac atg atc atg | 713 |
|                                                       Met Gln Arg Val Asn Met Ile Met | |
|                                                        1               5 | |
| gca gaa tca cca ggc ctc atc acc atc tgc ctt tta gga tat cta ctc | 761 |
| Ala Glu Ser Pro Gly Leu Ile Thr Ile Cys Leu Leu Gly Tyr Leu Leu | |
|  10                         15                       20 | |
| agt gct gaa tgt aca g gtttgtttcc ttttttaaaa tacattgagt atgcttgcct | 817 |
| Ser Ala Glu Cys Thr | |
| 25 | |
| tttagatata gaaatatctg atgctgtctt cttcactaaa ttttgattac atgatttgac | 877 |
| agcaatattg aagagtctaa cagccagcac gcaggttggt aagtactgtg gaacatcac | 937 |
| agattttggc tccatgccct aaagagaaat tggctttcag attatttgga ttaaaaacaa | 997 |
| agactttctt aagagatgta aaattttcat gatgttttct tttttgctaa actaaagaa | 1057 |
| ttattctttt acatttcagt ttttcttgat catgaaaacg ccaacaaaat tctgaatcgg | 1117 |
| ccaaagaggt ataattcagg taaattggaa gagtttgttc aagggaatct agagagagaa | 1177 |
| tgtatggaag aaaagtgtag ttttgaagaa gcacgagaag ttttttgaaaa cactgaaaga | 1237 |
| acaactgaat tttggaagca gtatgttgat ggagatcagt gtgagtccaa tccatgttta | 1297 |
| aatggcggca gttgcaagga tgacattaat tcctatgaat gttggtgtcc ctttggattt | 1357 |
| gaaggaaaga actgtgaatt agatgtaaca tgtaacatta gaatggcag atgcgagcag | 1417 |
| ttttgtaaaa atagtgctga taacaaggtg gtttgctcct gtactgaggg atatcgactt | 1477 |
| gcagaaaacc agaagtcctg tgaaccagca gtgccatttc catgtggaag agtttctgtt | 1537 |
| tcacaaactt ctaagctcac ccgtgctgag actgtttttc ctgatgtgga ctatgtaaat | 1597 |
| tctactgaag ctgaaaccat tttggataac atcactcaaa gcacccaatc atttaatgac | 1657 |
| ttcactcggg ttgttggtgg agaagatgcc aaaccaggtc aattcccttg gcaggttgtt | 1717 |
| ttgaatggta agttgatgc attctgtgga ggctctatcg ttaatgaaaa atggattgta | 1777 |
| actgctgccc actgtgttga aactggtgtt aaaattacag ttgtcgcagg tgaacataat | 1837 |

```
attgaggaga cagaacatac agagcaaaag cgaaatgtga ttcgaattat tcctcaccac   1897
aactacaatg cagctattaa taagtacaac catgacattg cccttctgga actggacgaa   1957
cccttagtgc taaacagcta cgttacacct atttgcattg ctgacaagga atacacgaac   2017
atcttcctca aatttggatc tggctatgta agtggctggg aagagtctt ccacaaaggg    2077
agatcagctt tagttcttca gtaccttaga gttccacttg ttgaccgagc cacatgtctt   2137
cgatctacaa agttcaccat ctataacaac atgttctgtg ctggcttcca tgaaggaggt   2197
agagattcat gtcaaggaga tagtggggga ccccatgtta ctgaagtgga agggaccagt   2257
ttcttaactg gaattattag ctggggtgaa gagtgtgcaa tgaaaggcaa atatggaata   2317
tataccaagg tgtcccggta tgtcaactgg attaaggaaa aaacaaagct cactgacaaa   2377
actcacacat gcccaccgtg cccagctccg gaactcctgg gcggaccgtc agtcttcctc   2437
ttccccccaa aacccaagga caccctcatg atctcccgga cccctgaggt cacatgcgtg   2497
gtggtggacg tgagccacga agaccctgag gtcaagttca actggtacgt ggacggcgtg   2557
gaggtgcata atgccaagac aaagccgcgg gaggagcagt acaacagcac gtaccgtgtg   2617
gtcagcgtcc tcaccgtcct gcaccaggac tggctgaatg gcaaggagta caagtgcaag   2677
gtctccaaca aagccctccc agcccccatc gagaaaacca tctccaaagc caagggcag   2737
ccccgagaac cacaggtgta caccctgccc ccatcccggg atgagctgac caagaaccag   2797
gtcagcctga cctgcctggt caaaggcttc tatcccagcg acatcgccgt ggagtgggag   2857
agcaatgggc agccggagaa caactacaag accacgcctc ccgtgttgga ctccgacggc   2917
tccttcttcc tctacagcaa gctcaccgtg gacaagagca ggtggcagca ggggaacgtc   2977
ttctcatgct ccgtgatgca tgaggctctg cacaaccact acacgcagaa gagcctctcc   3037
ctgtctccgg gtaaatgaga attcagacat gataagatac attgatgagt ttggacaaac   3097
cacaactaga atgcagtgaa aaaaatgctt tatttgtgaa atttgtgatg ctattgcttt   3157
atttgtaacc attataagct gcaataaaca agttggggtg gcgaagaac tccagcatga    3217
gatcccgcg ctggaggatc atccagccgg cgtcccggaa aacgattccg aagcccaacc    3277
tttcatagaa ggcggcggtg gaatcgaaat ctcgtagcac gtgtcagtcc tgctcctcgg   3337
ccacgaagtg cacgcagttg ccggccgggt cgcgcagggc gaactcccgc ccccacggct   3397
gctcgccgat ctcggtcatg gccggcccgg aggcgtcccg gaagttcgtg gacacgacct   3457
ccgaccactc ggcgtacagc tcgtccaggc cgcgcaccca cacccaggcc aggtgttgt    3517
ccggcaccac ctggtcctgg accgcgctga tgaacagggt cacgtcgtcc ggaccacac    3577
cggcgaagtc gtcctccacg aagtcccggg agaacccgag ccggtcggtc agaactcga    3637
ccgctccggc gacgtcgcgc gcggtgagca ccggaacggc actggtcaac ttggccatgg   3697
tttagttcct caccttgtcg tattatacta tgccgatata ctatgccgat gattaattgt   3757
caacacgtgc tgatcagatc cgaaaatgga tatacaagct cccgggagct ttttgcaaaa   3817
gcctaggcct ccaaaaaagc ctcctcacta cttctggaat agctcagagg cagaggcggc   3877
ctcggcctct gcataaataa aaaaaattag tcagccatgg ggcggagaat gggcggaact   3937
gggcggagtt aggggcggga tgggcggagt taggggcggg actatggttg ctgactaatt   3997
gagatgcatg ctttgcatac ttctgcctgc tggggagcct ggggactttc cacacctggt   4057
tgctgactaa ttgagatgca tgcttttgcat acttctgcct gctggggagc tggggactt    4117
tccacaccct cgtcgagcta gcttcgtgag gctccggtgc ccgtcagtgg gcagagcgca   4177
```

```
catcgcccac agtccccgag aagttggggg gaggggtcgg caattgaacc ggtgcctaga    4237
gaaggtggcg cggggtaaac tgggaaagtg atgtcgtgta ctggctccgc ctttttcccg    4297
agggtggggg agaaccgtat ataagtgcag tagtcgccgt gaacgttctt tttcgcaacg    4357
ggtttgccgc cagaacacag gtaagtgccg tgtgtggttc ccgcgggcct ggcctcttta    4417
cgggttatgg cccttgcgtg ccttgaatta cttccacctg gctccagtac gtgattcttg    4477
atcccgagct ggagccaggg gcgggccttg cgctttagga gccccttcgc ctcgtgcttg    4537
agttgaggcc tggcctgggc gctggggccg ccgcgtgcga atctggtggc accttcgcgc    4597
ctgtctcgct gctttcgata agtctctagc catttaaaat ttttgatgac ctgctgcgac    4657
gctttttttc tggcaagata gtcttgtaaa tgcgggccag gatctgcaca ctggtatttc    4717 ggttttggg gccgcgggcg gcgacgggc ccgtgcgtcc cagcgcacat gttcggcgag    4777
gcggggcctg cgagcgcggc caccgagaat cggacggggg tagtctcaag ctggccggcc    4837
tgctctggtg cctggcctcg cgccgccgtg tatcgccccg ccctgggcgg caaggctggc    4897
ccggtcggca ccagttgcgt gagcgaaaag atggccgctt cccggccctg ctccaggggg    4957
ctcaaaatgg aggacgcggc gctcgggaga gcggcgggt gagtcaccca cacaaaggaa    5017
aggggccttt ccgtcctcag ccgtcgcttc atgtgactcc acgagtacc gggcgccgtc    5077 caggcacctc gattagttct ggagcttttg gagtacgtcg tctttaggtt ggggggaggg    5137
gttttatgcg atggagtttc cccacactga gtgggtggag actgaagtta ggccagcttg    5197
gcacttgatg taattctcct tggaatttgc cctttttgag tttggatctt ggttcattct    5257
caagcctcag acagtggttc aaagttttt tcttccattt caggtgtcgt gaacacgtgg    5317
tcgcggccgc gccgccacca tggagacaga cacactcctg ctatgggtac tgctgctctg    5377
ggttccaggt tccactggtg acaaaactca cacatgccca ccgtgcccag cacctgaact    5437
cctgggagga ccgtcagtct tcctcttccc cccaaaaccc aaggacaccc tcatgatctc    5497
ccggacccct gaggtcacat gcgtggtggt ggacgtgagc cacgaagacc ctgaggtcaa    5557
gttcaactgg tacgtggacg gcgtggaggt gcataatgcc aagacaaagc cgcgggagga    5617
gcagtacaac agcacgtacc gtgtggtcag cgtcctcacc gtcctgcacc aggactggct    5677
gaatggcaag gagtacaagt gcaaggtctc caacaaagcc ctcccagccc ccatcgagaa    5737
aaccatctcc aaagccaaag gcagccccg agaaccacag gtgtacaccc tgcccccatc    5797
ccgcgatgag ctgaccaaga accaggtcag cctgacctgc ctggtcaaag gcttctatcc    5857
cagcgacatc gccgtggagt gggagagcaa tgggcagccg gagaacaact acaagaccac    5917
gcctcccgtg ttggactccg acggctcctt cttcctctac agcaagctca ccgtggacaa    5977
gagcaggtgg cagcaggga acgtcttctc atgctccgtg atgcatgagg ctctgcacaa    6037
ccactacacg cagaagagcc tctccctgtc tccgggtaaa tgactcgaga atctggccg    6097 gctgggcccg tttcgaaggt aagcctatcc ctaaccctct cctcggtctc gattctacgc    6157
gtaccggtca tcatcaccat caccattgag tttaaacccg ctgatcagcc tcgactgtgc    6217
cttctagttg ccagccatct gttgtttgcc cctcccccgt gccttccttg accctggaag    6277
gtgccactcc cactgtcctt tcctaataaa atgaggaaat tgcatcgcat tgtctgagta    6337
ggtgtcattc tattctgggg gtgggtgg ggcaggacag caaggggag gattgggaag    6397 acaatagcag gcatgctggg gatgcggtgg gctctatggc ttctgaggcg gaaagaacca    6457
gtggcggtaa tacggttatc cacagaatca ggggataacg caggaaagaa catgtgagca    6517
aaaggccagc aaaaggccag gaaccgtaaa aaggccgcgt tgctggcgtt tttccatagg    6577
```

```
ctccgccccc ctgacgagca tcacaaaaat cgacgctcaa gtcagaggtg gcgaaacccg    6637
acaggactat aaagatacca ggcgtttccc cctagaagct ccctcgtgcg ctctcctgtt    6697
ccgaccctgc cgcttaccgg atacctgtcc gcctttctcc cttcgggaag cgtggcgctt    6757
tctcatagct cacgctgtag gtatctcagt tcggtgtagg tcgttcgctc caagctgggc    6817
tgtgtgcacg aaccccccgt tcagcccgac cgctgcgcct tatccggtaa ctatcgtctt    6877
gagtccaacc cggtaagaca cgacttatcg ccactggcag cagccactgg taacaggatt    6937
agcagagcga ggtatgtagg cggtgctaca gagttcttga agtggtggcc taactacggc    6997
tacactagaa gaacagtatt tggtatctgc gctctgctga agccagttac cttcggaaaa    7057
agagttggta gctcttgatc cggcaaacaa accaccgctg gtagcggtgg ttttttgtt     7117 tgcaagcagc agattacgcg cagaaaaaaa ggatctcaag aagatccttt gatcttttct    7177
acggggtctg acgctcagtg gaacgaaaac tcacgttaag ggattttggt catgacatta    7237
acctataaaa ataggcgtat cacgaggccc tttcgtctcg cgcgtttcgg tgatgacggt    7297
gaaaacctct gacacatgca gctcccggag acggtcacag cttgtctgta agcggatgcc    7357
gggagcagac aagcccgtca gggcgcgtca gcgggtgttg gcgggtgtcg gggctggctt    7417
aactatgcgg catcagagca gattgtactg agagtgcacc atatatgcgg tgtgaaatac    7477
cgcacagatg cgtaaggaga aaataccgca tcaggcgcca ttcgccattc aggctgcgca    7537
actgttggga agggcgatcg gtgcgggcct cttcgctatt acgcca               7583
```

<210> SEQ ID NO 14
<211> LENGTH: 688
<212> TYPE: PRT
<213> ORGANISM: Artificial Sequence
<220> FEATURE:
<223> OTHER INFORMATION: FIX-Fc Chain
<220> FEATURE:
<221> NAME/KEY: SIGNAL
<222> LOCATION: (1)..(28)
<220> FEATURE:
<221> NAME/KEY: MISC_FEATURE
<222> LOCATION: (29)..(48)
<223> OTHER INFORMATION: FIX Propeptide
<220> FEATURE:
<221> NAME/KEY: MISC_FEATURE
<222> LOCATION: (402)..(688)
<223> OTHER INFORMATION: Mature Fc

<400> SEQUENCE: 14

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125
```

```
Glu Leu Asp Val Thr Cys Asn Ile Lys Asn Gly Arg Cys Glu Gln Phe
        130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
        290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Asp Lys Thr
450                 455                 460
His Thr Cys Pro Pro Cys Pro Ala Pro Glu Leu Leu Gly Gly Pro Ser
465                 470                 475                 480
Val Phe Leu Phe Pro Pro Lys Pro Lys Asp Thr Leu Met Ile Ser Arg
                485                 490                 495
Thr Pro Glu Val Thr Cys Val Val Val Asp Val Ser His Glu Asp Pro
            500                 505                 510
Glu Val Lys Phe Asn Trp Tyr Val Asp Gly Val Glu Val His Asn Ala
        515                 520                 525
Lys Thr Lys Pro Arg Glu Glu Gln Tyr Asn Ser Thr Tyr Arg Val Val
        530                 535                 540
```

```
Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
                580                 585                 590

Pro Pro Ser Arg Asp Glu Leu Thr Lys Asn Gln Val Ser Leu Thr Cys
            595                 600                 605

Leu Val Lys Gly Phe Tyr Pro Ser Asp Ile Ala Val Glu Trp Glu Ser
        610                 615                 620

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
                660                 665                 670

Leu His Asn His Tyr Thr Gln Lys Ser Leu Ser Leu Ser Pro Gly Lys
            675                 680                 685
```